US011884915B2

(12) United States Patent
Ryan et al.

(10) Patent No.: US 11,884,915 B2
(45) Date of Patent: Jan. 30, 2024

(54) GUIDE RNAS WITH CHEMICAL MODIFICATION FOR PRIME EDITING

(71) Applicant: Agilent Technologies, Inc., Santa Clara, CA (US)

(72) Inventors: Daniel E. Ryan, San Francisco, CA (US); Robert Kaiser, Santa Clara, CA (US); Douglas J. Dellinger, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 17/931,535

(22) Filed: Sep. 12, 2022

(65) Prior Publication Data

US 2023/0092393 A1 Mar. 23, 2023

Related U.S. Application Data

(60) Provisional application No. 63/243,055, filed on Sep. 10, 2021.

(51) Int. Cl.

| | |
|---|---|
| ***C12N 9/22*** | (2006.01) |
| ***C12N 15/10*** | (2006.01) |
| ***C12N 15/62*** | (2006.01) |

(52) U.S. Cl.

CPC ............. *C12N 15/102* (2013.01); *C12N 9/22* (2013.01); *C12N 15/62* (2013.01); *C12N 2310/20* (2017.05); *C12N 2310/315* (2013.01); *C12N 2310/321* (2013.01)

(58) Field of Classification Search

CPC ........ C12N 15/102; C12N 15/62; C12N 9/22; C12N 2310/20; C12N 2310/315; C12N 2310/321

See application file for complete search history.

(56) References Cited

U.S. PATENT DOCUMENTS

| | | | |
|---|---|---|---|
| 4,373,071 | A | 2/1983 | Itakura |
| 4,458,066 | A | 7/1984 | Caruthers et al. |
| 4,500,707 | A | 2/1985 | Caruthers et al. |
| 4,668,777 | A | 5/1987 | Caruthers et al. |
| 4,973,679 | A | 11/1990 | Caruthers et al. |
| 5,032,401 | A | 7/1991 | Jamas et al. |
| 5,047,524 | A | 9/1991 | Andrus et al. |
| 5,132,418 | A | 7/1992 | Caruthers et al. |
| 5,153,319 | A | 10/1992 | Caruthers et al. |
| 5,262,530 | A | 11/1993 | Andrus et al. |
| 5,607,677 | A | 3/1997 | Jamas et al. |
| 5,700,642 | A | 12/1997 | Monforte et al. |
| 7,371,580 | B2 | 5/2008 | Yakhini et al. |
| 7,682,828 | B2 | 3/2010 | Jaenisch et al. |
| 8,058,065 | B2 | 11/2011 | Yamanaka et al. |
| 8,202,983 | B2 | 6/2012 | Dellinger et al. |
| 8,530,238 | B2 | 9/2013 | Yamanaka et al. |
| 8,791,248 | B2 | 7/2014 | Yamanaka et al. |
| 8,865,406 | B2 | 10/2014 | Zhang et al. |
| 8,871,504 | B2 | 10/2014 | Yamanaka et al. |
| 8,889,418 | B2 | 11/2014 | Zhang et al. |
| 8,895,308 | B1 | 11/2014 | Zhang et al. |
| 8,900,871 | B2 | 12/2014 | Okita et al. |
| 8,906,616 | B2 | 12/2014 | Zhang et al. |
| 9,267,135 | B2 | 2/2016 | Church et al. |
| 9,738,908 | B2 | 8/2017 | Wu |
| 9,745,610 | B2 | 8/2017 | Doudna et al. |
| 9,822,407 | B2 | 11/2017 | Joung et al. |
| 9,885,003 | B2 | 2/2018 | Edwards et al. |
| 9,885,033 | B2 | 2/2018 | Joung et al. |
| 10,266,850 | B2 | 4/2019 | Doudna et al. |
| 10,337,001 | B2 | 7/2019 | Ryan et al. |
| 10,767,175 | B2 | 9/2020 | Dellinger et al. |
| 10,900,034 | B2 | 1/2021 | Ryan et al. |
| 11,306,309 | B2 * | 4/2022 | Porteus .................. A61P 37/02 |
| 11,535,846 | B2 * | 12/2022 | Porteus .................... A61P 3/00 |
| 2005/0281781 | A1 | 12/2005 | Ostroff |
| 2010/0076183 | A1 | 3/2010 | Dellinger et al. |
| 2014/0090113 | A1 | 3/2014 | Cogan et al. |

(Continued)

FOREIGN PATENT DOCUMENTS

| | | | |
|---|---|---|---|
| CA | 2872241 | A1 | 11/2013 |
| CA | 2922090 | C | 5/2021 |

(Continued)

OTHER PUBLICATIONS

Chen, Qiubing, Ying Zhang, and Hao Yin. "Recent advances in chemical modifications of guide RNA, mRNA and donor template for CRISPR-mediated genome editing." Advanced Drug Delivery Reviews 168 (2021): 246-258. (Year: 2021).*

International Search Report and Written Opinion dated Dec. 6, 2022 in PCT/US2022/076317.

Kim et al., "Genome-wide Analysis Reveals Specificities of Cpf1 Endonucleases in Human Cells," Nature Biotechnology, Aug. 2016, vol. 34, No. 8, pp. 863-868.

Kim et al., "Genome-Wide Target Specificities of CRISPR-Cas9 Nucleases Revealed by Multiplex Digenome-seq," Genome Research, 2016, vol. 26, pp. 406-415.

Kim et al., "Highly Efficient RNA-Guided Genome Editing in Human Cells via Delivery of Purified Cas9 Ribonucleoproteins," Genome Research, 2014, vol. 24, pp. 1012-1019.

(Continued)

*Primary Examiner* — Nancy J Leith
*Assistant Examiner* — Khaleda B Hasan
(74) *Attorney, Agent, or Firm* — K&L Gates LLP

(57) ABSTRACT

Provided herein are compositions and methods for inducing CRISPR/Cas-based editing of a target nucleic acid (e.g., target DNA or target RNA) in vitro or in a cell, using modified prime editing guide RNAs (pegRNAs) that incorporate one or more chemically-modified nucleotides. The modified pegRNAs disclosed herein may be used to induce Cas-mediated incorporation of one or more nucleotide changes and/or targeted mutagenesis of a target nucleic acid. The nucleotide change can include, e.g., one or more nucleotide changes, an insertion of one or more nucleotides, or a deletion of one or more nucleotides.

23 Claims, 16 Drawing Sheets

Specification includes a Sequence Listing.

(56) References Cited

U.S. PATENT DOCUMENTS

2014/0090116 A1 3/2014 Ainley et al.
2014/0170753 A1 6/2014 Zhang
2014/0186919 A1 7/2014 Zhang et al.
2014/0242664 A1 8/2014 Zhang et al.
2014/0273037 A1 9/2014 Wu
2014/0273226 A1 9/2014 Wu
2014/0273232 A1 9/2014 Zhang et al.
2014/0273233 A1 9/2014 Chen et al.
2014/0273235 A1 9/2014 Voytas et al.
2014/0294773 A1 10/2014 Brouns et al.
2014/0295555 A1 10/2014 Mishra
2014/0295557 A1 10/2014 Joung et al.
2014/0309487 A1 10/2014 Lee et al.
2014/0310828 A1 10/2014 Lee et al.
2014/0349400 A1 11/2014 Jakimo et al.
2014/0357523 A1 12/2014 Zeiner et al.
2014/0364333 A1 12/2014 Wu et al.
2015/0044191 A1 2/2015 Liu et al.
2015/0044192 A1 2/2015 Liu et al.
2015/0044772 A1 2/2015 Zhao
2015/0064149 A1 3/2015 West et al.
2015/0064708 A1 3/2015 Sastry-Dent et al.
2015/0067921 A1 3/2015 Cogan et al.
2015/0071889 A1 3/2015 Musunuru et al.
2015/0071906 A1 3/2015 Liu et al.
2015/0071946 A1 3/2015 Solyom et al.
2015/0079680 A1 3/2015 Bradley et al.
2015/0098954 A1 4/2015 Hyde et al.
2015/0118216 A1 4/2015 Liu et al.
2015/0128307 A1 5/2015 Sastry-Dent et al.
2015/0128308 A1 5/2015 Sastry-Dent et al.
2015/0128309 A1 5/2015 Sastry-Dent et al.
2015/0133315 A1 5/2015 Jacobson et al.
2015/0140664 A1 5/2015 Byrne et al.
2015/0156996 A1 6/2015 Fahrenkrug et al.
2015/0232881 A1 8/2015 Glucksmann et al.
2015/0315252 A1 11/2015 Haugwitz et al.
2015/0315576 A1 11/2015 Caliando et al.
2015/0322432 A1 11/2015 Anderson et al.
2015/0344836 A1 12/2015 Finer et al.
2016/0030477 A1 2/2016 Conway et al.
2016/0046959 A1 2/2016 Landel et al.
2016/0090622 A1 3/2016 Liu et al.
2016/0138027 A1 5/2016 Gan et al.
2016/0168592 A1 6/2016 Church et al.
2016/0206566 A1 7/2016 Lu et al.
2016/0257974 A1 9/2016 Bradley et al.
2016/0289675 A1 10/2016 Ryan et al.
2016/0298097 A1 10/2016 Chavez et al.
2016/0339064 A1 11/2016 Kovarik et al.
2017/0051296 A1 2/2017 Beetham et al.
2017/0166893 A1 6/2017 Doudna et al.
2017/0298383 A1 10/2017 Albertsen et al.
2020/0339980 A1 10/2020 Dellinger et al.
2021/0079389 A1 3/2021 Ryan et al.
2022/0195426 A1* 6/2022 Porteus .................. A61P 25/00

FOREIGN PATENT DOCUMENTS

CN 104854241 A 8/2015
EP 2800811 A1 11/2014
EP 2892321 A2 7/2015
EP 2893006 A1 7/2015
EP 3241902 B1 2/2018
EP 3835419 A1 6/2021
NO 2014093655 A2 6/2014
WO 2008091703 A2 7/2008
WO 2013126794 A1 8/2013
WO 2013141680 A1 9/2013
WO 2013142578 A1 9/2013
WO 2013176772 A1 11/2013
WO 2013176844 A1 11/2013
WO 2014039684 A1 3/2014
WO 2014039702 A2 3/2014
WO 2014039970 A9 3/2014
WO 2014065596 A1 5/2014
WO 2014071219 A1 5/2014
WO 2014089290 A1 6/2014
WO 2014089513 A1 6/2014
WO 2014089533 A2 6/2014
WO 2014093595 A1 6/2014
WO 2014093622 A2 6/2014
WO 2014093635 A1 6/2014
WO 2014093661 A2 6/2014
WO 2014093688 A1 6/2014
WO 2014093694 A1 6/2014
WO 2014093701 A1 6/2014
WO 2014093709 A1 6/2014
WO 2014093712 A1 6/2014
WO 2014093718 A1 6/2014
WO 2014099744 A1 6/2014
WO 2014099750 A2 6/2014
WO 2014144288 A1 9/2014
WO 2014144592 A2 9/2014
WO 2014144761 A2 9/2014
WO 2014145599 A2 9/2014
WO 2014150624 A1 9/2014
WO 2014152432 A2 9/2014
WO 2014153118 A1 9/2014
WO 2014159719 A1 10/2014
WO 2014165349 A1 10/2014
WO 2014165825 A2 10/2014
WO 2014172458 A1 10/2014
WO 2014172470 A2 10/2014
WO 2014186585 A2 11/2014
WO 2014191128 A1 12/2014
WO 2014191518 A1 12/2014
WO 2014191521 A2 12/2014
WO 2014197568 A2 12/2014
WO 2014201015 A2 12/2014
WO 2014204723 A9 12/2014
WO 2014204724 A9 12/2014
WO 2014204725 A1 12/2014
WO 2014204726 A1 12/2014
WO 2014204728 A1 12/2014
WO 2015006294 A2 1/2015
WO 2015006437 A1 1/2015
WO 2015006498 A2 1/2015
WO 2015013583 A2 1/2015
WO 2015026883 A1 2/2015
WO 2015026885 A1 2/2015
WO 2015026886 A1 2/2015
WO 2015030881 A1 3/2015
WO 2015033293 A1 3/2015
WO 2015035136 A2 3/2015
WO 2015035139 A2 3/2015
WO 2015035162 A2 3/2015
WO 2015040075 A1 3/2015
WO 2015052133 A1 4/2015
WO 2015052231 A2 4/2015
WO 2015053995 A1 4/2015
WO 2015054253 A1 4/2015
WO 2015054375 A2 4/2015
WO 2015066636 A2 5/2015
WO 2015066637 A1 5/2015
WO 2015070083 A1 5/2015
WO 2015075056 A1 5/2015
WO 2015089277 A1 6/2015
WO 2015089351 A1 6/2015
WO 2015089354 A1 6/2015
WO 2015089406 A1 6/2015
WO 2015089419 A2 6/2015
WO 2015089427 A1 6/2015
WO 2015089462 A1 6/2015
WO 2015089465 A1 6/2015
WO 2015089473 A1 6/2015
WO 2015089486 A2 6/2015
WO 2015184259 A1 12/2015
WO 2015184262 A1 12/2015
WO 2015184268 A1 12/2015
WO 2015200334 A1 12/2015
WO 2015200378 A1 12/2015
WO 2015200555 A2 12/2015
WO 2015200725 A1 12/2015

(56) References Cited

FOREIGN PATENT DOCUMENTS

| | | | |
|---|---|---|---|
| WO | 2016022363 A2 | 2/2016 | |
| WO | 2016033246 A1 | 3/2016 | |
| WO | 2016033315 A2 | 3/2016 | |
| WO | 2016046288 A1 | 3/2016 | |
| WO | 2016049024 A2 | 3/2016 | |
| WO | 2016049163 A2 | 3/2016 | |
| WO | 2016049251 A1 | 3/2016 | |
| WO | 2016049657 A1 | 3/2016 | |
| WO | 2016057755 A1 | 4/2016 | |
| WO | 2016057800 A1 | 4/2016 | |
| WO | 2016057821 A2 | 4/2016 | |
| WO | 2016057835 A2 | 4/2016 | |
| WO | 2016057951 A2 | 4/2016 | |
| WO | 2016069282 A1 | 5/2016 | |
| WO | 2016069283 A1 | 5/2016 | |
| WO | 2016070037 A2 | 5/2016 | |
| WO | 2016073079 A2 | 5/2016 | |
| WO | 2016089433 A1 | 6/2016 | |
| WO | 2017053729 A1 | 3/2017 | |
| WO | 2017104404 A1 | 6/2017 | |
| WO | 2017105991 A1 | 6/2017 | |
| WO | 2017106414 A1 | 6/2017 | |
| WO | 2017106569 A1 | 6/2017 | |
| WO | 2017106657 A1 | 6/2017 | |
| WO | 2017106767 A1 | 6/2017 | |
| WO | 2019084664 A1 | 5/2019 | |
| WO | 2019126037 A1 | 6/2019 | |
| WO | 2019183000 A1 | 9/2019 | |
| WO | 2020191242 A1 | 9/2020 | |
| WO | WO-2020191248 A1 * | 9/2020 | ........... C12N 15/102 |

OTHER PUBLICATIONS

Kleinstiver et al., "Genome-wide Specificities of CRISPR-Cas Cpf1 Nucleases in Human Cells," Nature Biotechnology, Aug. 2016, vol. 34, No. 8, pp. 869-874.

Kleinstiver et al., "High-fidelity CRISPR-Cas9 Nucleases with no Detectable Genome-wide off-target Effects," Nature, Jan. 28, 2016, vol. 529, pp. 490-495.

Knight et al., "Dynamics of CRISPR-Cas9 Genome Interrogation in Living Cells," Science, Nov. 13, 2015, vol. 350, Issue. 6262, pp. 823-826.

Koike-Yusa et al., "Genome-Wide Recessive Genetic Screening in Mammalian Cells With a Lentiviral CRISPR-Guide RNA Library," Nature Biotechnology, 2014, vol. 32, No. 3, pp. 267-273.

Komor et al., "Programmable Editing of a Target Base in Genomic DNA without Double-stranded DNA Cleavage," Nature, May 19, 2016, vol. 533, pp. 420-424.

Koo et al., "Measuring and Reducing Off-Target Activities of Programmable Nucleases Including CRISPR-Cas9," Mol. Cells, 2015, vol. 38, No. 6, pp. 475-481.

Krueger et al., "Synthesis and Properties of Size-expanded DNAs: Toward Designed, Functional Genetic Systems," Acc. Chem. Res., Feb. 2007, vol. 40, No. 2, pp. 141-150.

Krutzfeldt et al., "Silencing of MicroRNAs in Vivo with 'Antagomirs'," Nature, Letters, 2005, 5 pages.

Krutzfeldt et al., "Specificity, Duplex Degradation and Subcellular Localization of Antagomirs," Nucleic Acids Research, 2007, vol. 35, No. 9, pp. 2885-2892.

Kumar et al., "Template-Directed Oligonucleotide Strand Ligation, Covalent Intramolecular DNA Circularization and Catenation Using Click Chemistry," J. Am. Chem. Soc., 2007, vol. 129, No. 21, pp. 6859-6864.

Kuscu et al., "Genome-wide Analysis Reveals Characteristics of Off-target Sites Bound by the Cas9 Endonuclease," Nature Biotechnology, Jul. 2014, vol. 32, No. 7, pp. 677-683.

Kuznetsova et al., "Synthesis and Properties of DNA Duplexes Containing Hydrocarbon Bridges Instead of a Nucleoside Residue," Bioorganicheskaia Khimiia/Akademiia Nauk SSSR, Dec. 1988, vol. 14, No. 12, pp. 1656-1662.

Lahoud et al., "Enzymatic Synthesis of Structure-Free DNA with Pseudo-Complementary Properties," Nucleic Acids Research, 2008, vol. 36, No. 10, pp. 3409-3419.

Lange et al., "Classical Nuclear Localization Signals: Definition, Function, and Interaction with Importin α*," Journal of Biological Chemistry, Feb. 23, 2007, vol. 282, No. 8, pp. 5101-5105.

Larson et al., "Real-Time Observation of Transcription Initiation and Elongation on an Endogenous Yeast Gene," Science, Apr. 22, 2011, vol. 332, No. 6028, pp. 475-478.

Ledford, H., "CRISPR, The Disruptor," Nature, Jun. 4, 2015, vol. 522, pp. 20-24.

Lee et al., "Nuclease Target Site Selection for Maximizing On-target Activity and Minimizing off-target Effects in Genome Editing," Molecular Therapy, Mar. 2016, vol. 24, No. 3, pp. 475-487.

Lennox et al., "A Direct Comparison of Anti-microRNA Oligonucleotide Potency," Pharmaceutical Research, Apr. 28, 2010, vol. 27, pp. 1788-1799.

Lim et al., "Structural Roles of Guide RNAs in the Nuclease Activity of Cas9 Endonuclease," Nature Communications, 2016, vol. 7, No. 13350, pp. 1-8.

Limbach et al., "Summary: the Modified Nucleosides of RNA," Nucleic Acids Research, 1994 vol. 22, No. 12, pp. 2183-2196.

Lin et al., "CRISPR/Cas9 Systems have off-target Activity with Insertions or Deletions Between Target DNA and Guide RNA Sequences," Nucleic Acids Research, 2014, vol. 42, No. 11, pp. 7473-7485.

Lujambio et al., "Genetic Unmasking of an Epigenetically Silenced MicroRNA in Human Cancer Cells," (Spanish National Cancer Centre) Cancer Res., Feb. 15, 2007, vol. 67, No. 4, pp. 1424-1429.

Ma et al., "CRISPR-Cas9 Nuclear Dynamics and Target Recognition in Living Cells," J. Cell Biol, 2016, vol. 214, No. 5, pp. 529-537.

Mali et al., "CAS9 Transcriptional Activators Ffor Target Specificity Screening and Paired Nickases for Cooperative Genome Engineering," Nature Biotechnology, Aug. 1, 2013, vol. 31, No. 9, pp. 833-838.

Mali et al., "RNA-Guided Human Genome Engineering via Cas9," Science, 2013, vol. 339, No. 6121, pp. 823-826.

Miller et al., "An Improved Zinc-finger Nuclease Architecture for Highly Specific Genome Editing," Nature Biotechnology, Jul. 2007, vol. 25, No. 7, pp. 778-785.

Mojibul et al., "DNA-associated click chemistry," Sci. China Chem, The Frontiers of Chemical Biology and Synthesis, Feb. 2014, vol. 57, No. 2, pp. 215-231.

Monia et al., "Evaluation of 2'-Modified Oligonucleotides Containing 2'-Deoxy Gaps as Antisense Inhibitors of Gene Expression," The Journal of Biological Chemistry, 1993, vol. 268, No. 19, pp. 14514-14522.

New England Biolabs Inc., "Restriction Endonucleases," New England Biolabs Catalog, 1996, pp. 1-23.

Nishimasu et al., "Crystal Structure of Cas9 in Complex with Guide RNA and Target DNA," Cell, Feb. 27, 2014, vol. 156, pp. 935-949.

Notification of Transmittal of the International Search Report & Written Opinion in PCT/US2022/043553, dated Dec. 27, 2022, 12 pages.

O'Connell et al., "Programmable RNA Recognition and Cleavage by CRISPR/Cas9," Nature, Dec. 11, 2014, vol. 516, pp. 263-277.

Pattanayak et al., "High-Throughput Profiling of Off-target DNA Cleavage Reveals RNA-programmed Cas9 Nuclease Specificity," Nature Biotechnology, Sep. 2013, vol. 31, No. 9, pp. 839-843.

Peterson et al., "Genome-Wide Assessment of Efficiency and Specificity in CRISPR/Cas9 Mediated Multiple Site Targeting in *Arabidopsis*," Plos One 11, Sep. 13, 2016, e0162169 (Cas9 Specificity in *Arabidopsis*), pp. 1-11.

Piccirilli et al., "Enzymatic Incorporation of a New Base Pair into DNA and RNA Extends the Genetic Alphabet," Nature, Jan. 4, 1990, vol. 343, pp. 33-37.

Polstein et al., "Genome-wide Specificity of DNA Binding, Gene Regulation, and Chromatin Remodeling by TALE- and CRISPR/Cas9-based Transcriptional Activators," Genome Research, 2015, vol. 25, pp. 1158-1169.

Qiu et al., "Mutation Detection Using Surveyor™ Nuclease," Biotechniques, Apr. 2004, vol. 36, No. 4, pp. 702-707.

(56) References Cited

OTHER PUBLICATIONS

Rahdar et al., "Synthetic CRISPR RNA-Cas9-Guided Genome Editing in Human Cells," Proceedings of the National Academy of Sciences (PNAS), Nov. 16, 2015, vol. 112, No. 51, pp. E7110-E7117.
Ran et al., "Double Nicking by RNA-Guided Crispr Cas9 For Enhanced Genome Editing Specificity," Cell, Sep. 12, 2013, vol. 154, No. 6, pp. 1380-1389.
Ran et al., "In Vivo Genome Editing Using *Staphylococcus aureus* Cas9," Nature, Apr. 9, 2015, vol. 520, No. 7546, pp. 186-191.
Rappaport, H., "Replication of the Base Pair 6-Thioguanine/ 5-Methyl-2-pyrimidinone with the Large Klenow Fragment of *Escherichia coli* DNA Polymerase I," Biochemistry, 1993, vol. 32, No. 12, pp. 3047-3057.
Ren, et al., "Enhanced Specificity and Efficiency of the CRISPR/Cas9 System with Optimized sgRNA Parameters in *Drosophila*," Cell Rep, Nov. 6, 2014, vol. 9, No. 3, pp. 1151-1162.
Rgenome.net, "Cas-OFFinder," CRISPR RGEN Tools, Apr. 18, 2017, Retrieved from Internet: < http://www.rgenome.net/Cas-OFFinder>, 4 pages.
Ryan et al., "Phosphonoacetate Modifications Enhance the Stability and Editing Yields of Guide RNAS for Cas9 Editors," Biochemistry, Apr. 18, 2022, 9 pages.
Sanjana et al., "Improved Vectors and Genome-Wide Libraries for CRISPR Screening," Nature Methods, 2014, vol. 11, No. 8, pp. 783-784.
Schechner et al., "CRISPR Display: A Modular Method for Locus-specific Targeting of Long Noncoding RNAs and Synthetic RNA Devices in Vivo," Nat. Methods, Jul. 2015, vol. 12, No. 7, pp. 664-670.
Schneider et al., "Information Content of Binding Sites on Nucleotide Sequences," J. Mol. Biol., 1986, vol. 188, pp. 415-431.
Semenova et al., "Interference by Clustered Regularly Interspaced Short Palindromic Repeat (CRISPR) RNA is Governed by a Seed Sequence," Proc. Natl. Acad. Sci, Jun. 21, 2011, vol. 108, No. 25, pp. 10098-10103.
Shalem et al., "Genome-Scale CRISPR-Cas9 Knockout Screening in Human Cells," Science, Jan. 3, 2014, vol. 343, pp. 84-87.
Shen et al., "Efficient Genome Modification by CRISPR-Cas9 Nickase with Minimal Off-target Effects," Nature Methods, Apr. 2014, vol. 11, No. 4, pp. 399-402.
Singh et al., "Cas9-chromatin Binding Information Enables More Accurate CRISPR Off-target Prediction," Nucleic Acids Research, 2015, vol. 43, No. 18, pp. 1-8.
Singh et al., "Real-Time Observation of DNA Recognition and Rejection by the RNA-Guided Endonuclease Cas9," Nature Communications, 2016, vol. 7, No. 12778, pp. 1-8.
Slaymaker et al., "Rationally Engineered Cas9 Nucleases with Improved Specificity," Science, Dec. 1, 2015, vol. 351, pp. 84-88.
Smith et al., "Whole-Genome Sequencing Analysis Reveals High Specificity of CRISPR/Cas9 and TALEN-Based Genome Editing in Human iPSCs," Cell Stem Cell, Jul. 3, 2014, vol. 15, No. 1, pp. 12-13.
Soutschek et al., "Therapeutic Silencing of an Endogenous Gene by Systemic Administration of Modified SiRNAs," Nature Publishing Group, Nov. 11, 2004, vol. 432, pp. 173-178.
Synthego Corporation, "Curriculum Vitae of Henry Morrice Furneaux," May 20, 2022, 15 pages.
Synthego Corporation, "DharmaconTM Edit-RTM Gene Engineering System," GE Life Sciences, 2014, 2 pages.
Synthego Corporation, "Petition for Inter Partes Review of U.S. Pat. No. 10,337,001," Declaration of Henry Morrice Furneaux, May 29, 2022, 198 pages.
Synthego Corporation, "Petition for Inter Partes Review of U.S. Pat. No. 10,900,034," Declaration of Henry Morrice Furneaux, May 20, 2022, 217 pages.
Synthego Corporation, File Wrapper History filed on Dec. 3, 2015, U.S. Appl. No. 14/757,204, 1660 pages.
Synthego Corporation, File Wrapper History filed on May 25, 2017, U.S. Appl. No. 15/607,295, 1090 pages.
Synthego Corporation, Petition for Inter Partes Review filed on Jan. 4, 2022, U.S. Pat. No. 10,337,001, 103 pages.
Synthego Corporation, Petition for Inter Partes Review filed on Jan. 4, 2022, U.S. Pat. No. 10,900,034, 108 pages.
Synthego Corporation, Petitioner Synthego Corporation's Power of Attorney filed Dec. 17, 2021, U.S. Pat. No. 10,337,001, 3 pages.
Synthego Corporation, Petitioner Synthego Corporation's Power of Attorney filed on Dec. 17, 2021, U.S. Pat. No. 10,900,034, 3 pages.
Szczepek et al., "Structure-based Redesign of the Dimerization Interface Reduces the Toxicity of Zinc-finger Nucleases," Nature Biotechnology, Jul. 2007, vol. 25, No. 7, pp. 786-793.
Third Party Observations pursuant to Article 115 EPC in EP15866342.7, dated Jul. 1, 2021, 13 pages.
Thomas Jefferson University, "Off- Spotter," 2017, Retrieved from Internet: <https://cm.jefferson.edu/Off-Spotter>, 1 page.
Threlfall et al., "Synthesis and Biological Activity of Phosphonoacetate- and Thiophosphonoacetate-Modified 2'-O-Methyl Oligoribonucleotides," Organic & Biomolecular Chemistry, Jan. 28, 2012, vol. 10, No. 4, pp. 746-754.
Tietze et al., "Squaric Acid Diethyl Ester: A New Coupling Reagent for the Formation of Drug Biopolymer Conjugates. Synthesis of Squaric Acid Ester Amides and Diamides," Chem. Ber., 1991, vol. 124, pp. 1215-1221.
Timmer J., "Bacterial "Immune System" Used to Engineer Human DNA in Human Cells," Jan. 3, 2013, Retrieved from Internet: < URL: https://arstechnica.com/science/2013/01/bacterial-immune-system-used-to-engineerhuman-dna-in-human-cells/>, pp. 1-7.
Trafton, A., "New Method for Turning Genes on and off Could Enable More Complex Synthetic Biology Circuits," MIT News, Sep. 3, 2013, Retrieved from Internet: < URL:https://www.forbes.com/sites/matthewherper/2013/03/19/the-protein-that-could-change-biotechforever/?sh=15f215a32063>, 4 pages.
Tsai et al., "Defining and Improving the Genome-wide Specificities of CRISPR-Cas9 Nucleases," Nat. Rev. Genetics, May 2016, vol. 17, pp. 300-312.
Tsai et al., "Dimeric CRISPR RNA-Guided Fokl Nucleases for Highly Specific Genome Editing," Nat. Biotechnol, Jun. 2014, vol. 32, No. 6, pp. 569-576.
Tsai et al., "GUIDE-seq Enables Genome-wide Profiling of off-target Cleavage by CRISPR-Cas Nucleases," Nature Biotechnology, Feb. 2015, vol. 33, No. 2, pp. 187-197.
Tycko et al., "Methods for Optimizing CRISPR-Cas9 Genome Editing Specificity," Molecular Cell, Aug. 4, 2016, vol. 63, pp. 355-370.
Wang et al., "Genetic Screens in Human Cells Using the CRISPR-Cas9 System," Science, Jan. 3, 2014, vol. 343, pp. 80-84.
Wang et al., "Unbiased Detection of off-target Cleavage by CRISPR-Cas9 and TALENs using Integrase-defective Lentiviral Vectors," Nature Biotechnology, Feb. 2015, vol. 33, No. 2, pp. 175-178.
Wu et al., "Genome-wide Binding of the CRISPR Endonuclease Cas9 in Mammalian Cells," Nature Biotechnology, Jul. 2014, vol. 32, No. 7, pp. 670-676.
Wu et al., "Target Specificity of the CRISPR-Cas9 System," Quantitative Biology, Jun. 2014, vol. 2, No. 2, pp. 59-70.
Wyvekens et al., "Dimeric CRISPR RNA-Guided Fokl-dCas9 Nucleases Directed by Truncated gRNAs for Highly Specific Genome Editing," Human Gene Therapy, 2015, vol. 26, No. 7, pp. 425-431.
Yamada et al., "Synthesis and Biochemical Evaluation of Phosphonoformate Oligodeoxyribonucleotides," J. Am. Chem. Soc., 2006, vol. 128, No. 15, pp. 5251-5261.
Yang et al., "Artificially Expanded Genetic Information System: A New Base Pair With An Alternative Hydrogen Bonding Pattern," Nucleic Acids Research, 2006, vol. 34, No. 21, pp. 6095-6101.
Yang et al., "Targeted and Genome-Wide Sequencing Reveal Single Nucleotide Variations Impacting Specificity of Cas9 in Human Stem Cells," Nature Communications, 2014, vol. 5, No. 5507, pp. 1-6.
Yoo et al., "2'-O-Methyl-Modified Phosphorothioate Antisense Oligonucleotides Have Reduced Non-Specific Effects In Vitro," Nucleic Acids Research, Apr. 2, 2004, vol. 32, No. 6, pp. 2008-2016.
Zetsche et al., "Cpf1 is a Single RNA-Guided Endonuclease of a Class 2 CRISPR-Cas System," Cell, Oct. 22, 2015, vol. 163, No. 3, pp. 759-771.

(56) References Cited

OTHER PUBLICATIONS

Zhang et al., "Evolution of Functional Six-Nucleotide DNA," J. Am. Chem. Soc., 2015, vol. 137, No. 21, pp. 6734-6737.
Zheng et al., "Profiling Single-guide RNA Specificity Reveals a Mismatch Sensitive Core Sequence," Scientific Reports, 2017, vol. 7, No. 40638, pp. 1-8.
Zhou et al., "High-Throughput Screening of a CRISPR / Cas9 Library for Functional Genomics in Human Cells," Nature, Letter, May 22, 2014, vol. 509, 487-492.
Zischewski et al., "Detection of on-target and off-target Mutations Generated by CRISPR/Cas9 and Other Sequence-specific Nucleases," Biotechnology Advances, 2017, vol. 35, pp. 95-104.
Belfort et al. "Homing Endonucleases: Keeping the House in Order" Nucleic acids research, 1997, vol. 25, No. 17, pp. 3379-3388.
Bio-Synthesis, Inc., "2' O-Methyl RNA 2' Me Synthesis," Dec. 20, 2021, Retrieved from Internet: <URL:https://www.biosyn.com/oligonucleotideproduct/2-o-methyl-rna-2-ome-rna-synthesis.aspx>, 3 pages.
Bio-Synthesis, Inc., "Phosphorothioate DNA Synthesis," Dec. 20, 2021, Retrieved from Internet: <URL:https://www. biosyn.com/oligonucleotideproduct/phosphorothioate-dna-synthesismodification.aspx#>, 3 pages.
Bisaria et al., "Lessons from Enzyme Kinetics Reveal Specificity Principles for RNA-guided Nucleases in RNA Interference and CRISPR-based Genome Editing," Cell Systems, Jan. 25, 2017, vol. 4, pp. 21-29.
Briner et al., "Guide RNA Functional Modules Direct Cas9 Activity and Orthogonality," Molecular Cell, Oct. 23, 2014, vol. 56, pp. 333-339.
Chen et al., "Dynamic Imaging of Genomic Loci in Living Human Cells by an Optimized CRISPR/Cas System," Cell, Dec. 19, 2013, vol. 155, pp. 1479-1491.
Cho et al., "Analysis of Off-target Effects of CRISPR/Cas-derived RNA-guided Endonucleases and Nickases," Genome Research, 2014, vol. 24, pp. 132-141.
Cho et al., "Targeted Genome Engineering in Human Cells with the Cas9 RNA-guided Endonuclease," Nature Biotechnology, Mar. 2013, vol. 31, No. 3, pp. 230-232.
Cong et al., "Multiplex Genome Engineering Using Crispr/Cas Systems," Science, 2013, vol. 339, No. 6121, pp. 819-823.
Cradick et al., "CRISPR/Cas9 Systems Targeting β-globin and CCR5 Genes have Substantial off-target Activity," Nucleic Acids Research, 2013, vol. 41, No. 20, pp. 9584-9592.
Crispr, "CRISPR Design," 2017, Retrieved from Internet: <http://crispr.mit.edu>, 1 page.
Davis et al., "Improved Targeting of miRNA With Antisense Oligonucleotides," Nucleic Acids Research, May 11, 2006, vol. 34, No. 8, pp. 2294-2304.
Davis et al., "Small Molecule-Triggered Cas9 Protein with Improved Genome-editing Specificity," Nature Chemical Biology, May 2015, vol. 11, pp. 316-318.
Deleavey et al., "Designing Chemically Modified Oligonucleotides for Targeted Gene Silencing," Chemistry & Biology, Aug. 24, 2012, vol. 19, No. 8, pp. 937-954.
Dellinger et al., "Solid-Phase Chemical Synthesis of Phosphonoacetate and Thiophosphonoacetate Oligodeoxynucleotides," J. Am. Chem. Soc., 2003, vol. 125, pp. 940-950.
Dellinger et al., "Streamlined Process for the Chemical Synthesis of RNA Using 2'-O-Thionocarbamate-Protected Nucleoside Phosphoramidites in the Solid Phase," Journal of the American Chemical Society, Aug. 3, 2011, vol. 133, No. 30, pp. 11540-11556.
Deng et al., "CASFISH: CRISPR/Cas9-Mediated In Situ Labeling of Genomic Loci in Fixed Cells," Proceedings of The National Academy of Sciences (PNAS), Sep. 22, 2015, vol. 112, No. 38, pp. 11870-11875.
Doench et al., "Optimized sgRNA Design to Maximize Activity and Minimize Off-target Effects of CRISPR-Cas9," Nature Biotechnology, Feb. 2016, vol. 34, No. 2, pp. 184-191.
Doudna et al., "The New Frontier of Genome Engineering With CRISPR-Cas9," Genome Editing, Nov. 28, 2014, vol. 346, No. 6213, 11 pages.
Doyon et al., "Enhancing Zinc-Finger-Nuclease Activity with Improved Obligate Heterodimeric Architectures," Nature Methods, Jan. 2011, vol. 8, No. 1, pp. 74-81.
Eckstein, F., "Phosphorothioates, Essential Components of Therapeutic Oligonucleotides," Nucleic Acid Therapeutics, 2014, vol. 24, No. 6, pp. 374-387.
El-Sagheer et al., "Click Chemistry with DNA," Chemical Society Reviews, 2010, vol. 39, pp. 1388-1405.
Extended European Search Report in EP15866342.7, dated Jun. 13, 2018, 14 pages.
Frock et al., "Genome-Wide Detection of DNA Double-Stranded Breaks Induced by Engineered Nucleases," Nature Biotechnology, Feb. 2015, vol. 33, No. 2, pp. 179-186.
Fu et al., "Distinct Patterns of Cas9 Mismatch Tolerance in Vitro and in Vivo," Nucleic Acids Research, 2016, vol. 44, No. 11, pp. 5365-5377.
Fu et al., "High-frequency off-target Mutagenesis Induced by CRISPR-Cas Nucleases in Human Cells," Nature Biotechnology, Sep. 2013, vol. 31, No. 9, pp. 822-826.
Fu et al., "Improving CRISPR-Cas Nuclease Specificity Using Truncated Guide RNAs," Nature Biotechnology, Mar. 2014, vol. 32, No. 3, pp. 279-287.
Gao et al., "Single Cas9 Nickase Induced Generation of NRAMP1 Knockin Cattle with Reduced off-target Effects," Genome Biology, 2017, vol. 18, No. 13, pp. 1-15.
Gasiunas et al., "Cas9-crRNA Ribonucleoprotein Complex Mediates Specific DNA Cleavage for Adaptive Immunity in Bacteria," Proc. Natl. Acad. Sci., Sep. 4, 2012, vol. 109, No. 39, pp. E2579-E2586.
Gilbert et al., "Genome-Scale CRISPR-Mediated Control of Gene Repression and Activation," Cell, Oct. 23, 2014, vol. 159, pp. 647-661.
Gori et al., "Delivery and Specificity of CRISPR/Cas9 Genome Editing Technologies for Human Gene Therapy," Human Gene Therapy, 2015, vol. 26, No. 7, pp. 443-451.
Guilinger et al., "Fusion of Catalytically Inactive Cas9 to Fokl Nuclease Improves the Specificity of Genome Modification," Nature Biotechnology, Jun. 2014, vol. 32, No. 6, pp. 577-582.
Haeussler et al., "Evaluation of off-Target and on-Target Scoring Algorithms and Integration Into the Guide RNA Selection Tool CRISPOR," Genome Biology, 2016, vol. 17, No. 148, pp. 1-12.
Havlicek et al., "Re-engineered RNA-Guided Fokl-Nucleases for Improved Genome Editing in Human Cells," Molecular Therapy, Feb. 2017, vol. 25, No. 2, pp. 342-355.
Hendel et al., "Chemically Modified Guide RNAs Enhanced Crispr-cas Genome Editing in Human Primary Cells," Nature Biotechnology, Sep. 2015, vol. 33, No. 9, pp. 985-991.
Hendel et al., "Quantifying Genome-Editing Outcomes at Endogenous Loci using SMRT Sequencing," Cell Rep., Apr. 10, 2014, vol. 7, No. 1, pp. 293-305.
Hierper M., "[CRISPR/Cas9] Is Spreading Like Wildfire from Everyone Who Knows About It and It Certainly is Very Tantalizing," Forbes.com, Mar. 19, 2013, 5 pages.
Hruscha et al., "Efficient CRISPR/Cas9 Genome Editing with Low off-target effects in Zebrafish," Development, 2013, vol. 140, pp. 4982-4987.
Hsu et al., "DNA Targeting Specificity of RNA-guided Cas9 Nucleases," Nature Biotechnology, Sep. 2013, vol. 31, No. 9, pp. 827-834.
Hu et al., "Detecting DNA Double-stranded Breaks in Mammalian Genomes by Linear Amplification-mediated high-throughput Genome-wide Translocation Sequencing," Nature Protocols, 2016, vol. 11, No. 5, pp. 853-871.
Hiwang et al., "Efficient In Vivo Genome Editing Using RNA-Guided Nucleases," Nat Biotechnol., Mar. 2013, vol. 31, No. 3, pp. 227-229.
International Search Report and Written Opinion in PCT/US2015/000143, dated Apr. 19, 2016, 12 pages.
Iyer et al., "Off-target Mutations are Rare in Cas9-modified Mice," Nature Methods, Jun. 2015, vol. 12, No. 6, pp. 479.

(56) References Cited

OTHER PUBLICATIONS

Jiang et al., "A Cas9-guide RNA Complex Preorganized for Target DNA Recognition," Science, Jun. 26, 2015, vol. 348, Issue 6242, pp. 1477-1481.
Jiang et al., "RNA-Guided Editing of Bacterial Genomes Using Crispr-Cas Systems," Nature Biotechnology, 2013, vol. 31, No. 3, pp. 233-241.
Jinek et al., "A Programmable Dual-RNA-Guided DNA Endonuclease in Adaptive Bacterial Immunity," Science, Aug. 17, 2012, vol. 337, Issue 6096, pp. 816-821.
Jinek et al., "RNA-Programmed Genome Editing in Human Cells," eLife Research Article, Genomics and evolutionary biology, Human biology and medicine, Jan. 29, 2013, vol. 2, pp. 1-9.
Jinek et al., "Supplementary Materials for a Programmable Dual-RNA-Guided DNA Endonuclease in Adaptive Bacterial Immunity," Science, 2012, vol. 337, 37 pages.
Karvelis et al., "crRNA and traceRNA guide Cas9-mediated DNA Interference in *Streptococcus thermophilus*," RNA Biology, May 2013, vol. 10, No. 5, pp. 841-851.
Kim et al., "Digenome-seq: Genome-wide Profiling of CRISPR-Cas9 off-target Effects in Human Cells," Nature Methods, Mar. 2015, vol. 12, No. 3, pp. 237-243.

* cited by examiner

**Prime Editing of *EMX1* introduces an SNV that knocks-out the PAM:**

Wild-type 20-bp target plus PAM in *EMX1*: GAGTCCGAGCAGAAGAAGAAGGG (SEQ ID NO: 25)

SNV edit by prime editing (lower case): GAGTCCGAGCAGAAGAAGAAGtG (SEQ ID NO: 26)

**Prime Editing of *RUNX1* introduces a 3-base insertion:**

Wild-type 20-bp target plus PAM in *RUNX1*: GCATTTTCAGGAGGAAGCGATGG (SEQ ID NO: 27

3-base insertion by prime editing (lower case): GCATTTTCAGGAGGAAGCatgGATGG (SEQ ID NO: 28)

FIG. 11

SEQUENCE LISTING

```
Sequence total quantity: 24
SEQ ID NO: 1           moltype = RNA  length = 124
FEATURE                Location/Qualifiers
source                 1..124
                       mol_type = other RNA
                       organism = synthetic construct
SEQUENCE: 1
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggac                                                               124

SEQ ID NO: 2           moltype = RNA  length = 124
FEATURE                Location/Qualifiers
source                 1..124
                       mol_type = other RNA
                       organism = synthetic construct
SEQUENCE: 2
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggac                                                               124

SEQ ID NO: 3           moltype = RNA  length = 126
FEATURE                Location/Qualifiers
source                 1..126
                       mol_type = other RNA
                       organism = synthetic construct
```

```
SEQUENCE: 3
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggactt                                                             126

SEQ ID NO: 4           moltype = RNA  length = 128
FEATURE                Location/Qualifiers
source                 1..128
                       mol_type = other RNA
                       organism = synthetic construct
SEQUENCE: 4
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggactttt                                                           128

SEQ ID NO: 5           moltype = RNA  length = 124
FEATURE                Location/Qualifiers
source                 1..124
                       mol_type = other RNA
                       organism = synthetic construct
SEQUENCE: 5
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggac                                                               124

SEQ ID NO: 6           moltype = RNA  length = 124
FEATURE                Location/Qualifiers
source                 1..124
                       mol_type = other RNA
                       organism = synthetic construct
SEQUENCE: 6
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggac                                                               124

SEQ ID NO: 7           moltype = RNA  length = 124
FEATURE                Location/Qualifiers
source                 1..124
                       mol_type = other RNA
                       organism = synthetic construct
SEQUENCE: 7
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggac                                                               124

SEQ ID NO: 8           moltype = RNA  length = 126
FEATURE                Location/Qualifiers
source                 1..126
                       mol_type = other RNA
                       organism = synthetic construct
SEQUENCE: 8
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggactt                                                             126

SEQ ID NO: 9           moltype = RNA  length = 126
FEATURE                Location/Qualifiers
source                 1..126
                       mol_type = other RNA
                       organism = synthetic construct
SEQUENCE: 9
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggactt                                                             126

SEQ ID NO: 10          moltype = RNA  length = 127
FEATURE                Location/Qualifiers
source                 1..127
                       mol_type = other RNA
                       organism = synthetic construct
SEQUENCE: 10
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggacttt                                                            127
```

```
SEQ ID NO: 11          moltype = RNA  length = 128
FEATURE                Location/Qualifiers
source                 1..128
                       mol_type = other RNA
                       organism = synthetic construct
SEQUENCE: 11
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggactttt                                                           128

SEQ ID NO: 12          moltype = RNA  length = 128
FEATURE                Location/Qualifiers
source                 1..128
                       mol_type = other RNA
                       organism = synthetic construct
SEQUENCE: 12
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggactttt                                                           128

SEQ ID NO: 13          moltype = RNA  length = 128
FEATURE                Location/Qualifiers
source                 1..128
                       mol_type = other RNA
                       organism = synthetic construct
SEQUENCE: 13
gagtccgagc agaagaagaa gttttagagc tagaaatagc aagttaaaat aaggctagtc  60
cgttatcaac ttgaaaaagt ggcaccgagt cggtgcatgg gagcacttct tcttctgctc  120
ggactttt                                                           128

SEQ ID NO: 14          moltype = RNA  length = 129
FEATURE                Location/Qualifiers
source                 1..129
                       mol_type = other RNA
                       organism = synthetic construct
SEQUENCE: 14
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaat                                                          129

SEQ ID NO: 15          moltype = RNA  length = 129
FEATURE                Location/Qualifiers
source                 1..129
                       mol_type = other RNA
                       organism = synthetic construct
SEQUENCE: 15
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaat                                                          129

SEQ ID NO: 16          moltype = RNA  length = 131
FEATURE                Location/Qualifiers
source                 1..131
                       mol_type = other RNA
                       organism = synthetic construct
SEQUENCE: 16
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaatt t                                                       131

SEQ ID NO: 17          moltype = RNA  length = 133
FEATURE                Location/Qualifiers
source                 1..133
                       mol_type = other RNA
                       organism = synthetic construct
SEQUENCE: 17
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaatt ttt                                                     133

SEQ ID NO: 18          moltype = RNA  length = 129
FEATURE                Location/Qualifiers
source                 1..129
                       mol_type = other RNA
                       organism = synthetic construct
```

```
SEQUENCE: 18
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaat                                                          129

SEQ ID NO: 19          moltype = RNA  length = 129
FEATURE                Location/Qualifiers
source                 1..129
                       mol_type = other RNA
                       organism = synthetic construct
SEQUENCE: 19
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaat                                                          129

SEQ ID NO: 20          moltype = RNA  length = 129
FEATURE                Location/Qualifiers
source                 1..129
                       mol_type = other RNA
                       organism = synthetic construct
SEQUENCE: 20
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaat                                                          129

SEQ ID NO: 21          moltype = RNA  length = 131
FEATURE                Location/Qualifiers
source                 1..131
                       mol_type = other RNA
                       organism = synthetic construct
SEQUENCE: 21
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaatt t                                                       131

SEQ ID NO: 22          moltype = RNA  length = 133
FEATURE                Location/Qualifiers
source                 1..133
                       mol_type = other RNA
                       organism = synthetic construct
SEQUENCE: 22
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaatt ttt                                                     133

SEQ ID NO: 23          moltype = RNA  length = 133
FEATURE                Location/Qualifiers
source                 1..133
                       mol_type = other RNA
                       organism = synthetic construct
SEQUENCE: 23
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaatt ttt                                                     133

SEQ ID NO: 24          moltype = RNA  length = 133
FEATURE                Location/Qualifiers
source                 1..133
                       mol_type = other RNA
                       organism = synthetic construct
SEQUENCE: 24
gcattttcag gaggaagcga gttttagagc tagaaatagc aagttaaaat aaggctagtc  60
cgttatcaac ttgaaaaagt ggcaccgagt cggtgctgtc tgaagccatc catgcttcct  120
cctgaaaatt ttt                                                     133
```

GUIDE RNAS WITH CHEMICAL MODIFICATION FOR PRIME EDITING

CROSS-REFERENCE TO RELATED APPLICATION

The present application claims the benefit of priority to U.S. Provisional Application No. 63/243,055, filed Sep. 10, 2021, the entire contents of which is incorporated herein by reference in its entirety.

REFERENCE TO SEQUENCE LISTING SUBMITTED ELECTRONICALLY

The specification further incorporates by reference a concurrently-filed sequence listing submitted electronically via EFS-Web as a file named "SequenceListing.xml", created Sep. 12, 2022, which is 24,767 bytes in size. The sequence listing contained in this document is part of the specification and is herein incorporated by reference in its entirety.

TECHNICAL FIELD

The present disclosure relates to the field of biology. In particular, the present disclosure relates to the clusters of regularly interspaced short palindromic repeats (CRISPR) technology.

BACKGROUND

The native prokaryotic CRISPR-Cas system comprises an array of short DNA sequence repeats with intervening variable sequences of constant length (i.e., clusters of regularly interspaced short palindromic repeats, or "CRISPR"), and one or more sequences that express CRISPR-associated ("Cas") proteins. The RNA of the transcribed CRISPR locus (or "CRISPR array") is processed by a subset of the Cas proteins and cellular RNases into small guide RNAs, which generally have two components as discussed below. There are at least six different types of CRISPR systems: Type I, Type II, Type III, Type IV, Type V, and Type VI. The enzymes involved in the processing of the transcribed RNA into mature crRNA are different in these seven systems. In the native prokaryotic Type II system, the guide RNA ("gRNA") comprises two short, non-coding RNA species referred to as CRISPR RNA ("crRNA") and trans-acting RNA ("tracrRNA"). In an exemplary system, the gRNA forms a complex with a Cas protein. The gRNA:Cas protein complex binds a target polynucleotide sequence having a protospacer adjacent motif ("PAM") and a protospacer, the latter having a sequence complementary to a portion of the gRNA. The recognition and binding of the target polynucleotide by the gRNA:Cas protein complex induces cleavage of the target polynucleotide. The native CRISPR-Cas system functions as an immune system in prokaryotes, where gRNA:Cas protein complexes recognize and silence exogenous genetic elements in a manner analogous to RNAi in eukaryotic organisms, thereby conferring resistance to exogenous genetic elements such as infecting plasmids and phages. It has been demonstrated that the two short RNA species referred to as crRNA and tracrRNA can be connected by a short RNA stem-loop of various lengths into a single-guide RNA ("sgRNA") that functions similarly as the two naturally-occuring species (Jinek et al., *Science* 2012, 337, 816-821; Hsu et al., *Nat. Biotechnol.* 2013, 827-832; Chen et al., *Cell* 2013, 155, 1479-1491).

Prime editing is a CRISPR-based technology for the editing of targeted sequences in DNA, and it allows for various forms of base substitutions, such as transversion and transition mutations. It also allows for precise insertions and deletions, including large deletions of up to about 700 bp long. Notably prime editing does not require an exogenous DNA repair template. The foundational technology for prime editing was described in Anzalone et al. "Search-and-replace genome editing without double-strand breaks or donor DNA." *Nature* 576:7785 (2019) 149-157, and subsequent advances and variations have been reported (Anzalone et al. *Nat. Biotechnol.* 2020, 883-891; Hsu et al. *Nat. Commun.* 2021, 12:1034; Liu et al. *Nat. Commun.* 2021, 12: 2121; Lin et al. *Nat. Biotechnol.* 2021, 923-927; Choi et al. *Nat. Biotechnol.* 2022, 218-226; Nelson et al. *Nat. Biotechnol.* 2022, 402-410; Chen et al., *Cell* 2021, 184, 1-18; Anzalone et al. *Nat. Biotechnol.* 2022, 731-740). In these studies, a Cas9 nickase polypeptide was fused to a reverse transcriptase polypeptide, and this fusion protein employed a prime editing guide RNA (or "pegRNA") having a novel design such that the tracrRNA segment had two additional segments added onto its 3' end: (i) an RNA template segment, which is a sequence comprising the desired edits for the reverse transcriptase portion of the fusion protein to copy onto the 3' end of the nicked strand of the DNA target site (targeted by the Cas9 nickase portion), and (ii) a primer binding segment, which is a sequence complementary to the target sequence bearing the nicked 3' end, such that the nicked 3' end is captured by sequence hybridization to the primer binding sequence to allow primer extension of the nicked 3' end by the reverse transcriptase portion (as illustrated in FIG. 1). Among the recent advances are clever techniques that utilize a pair of pegRNAs to precisely install small to large edits in DNA target sites, comprising large deletions (up to about 1 kb) or insertions (up to about 150 bp) (see Anzalone et al. 2022; Lin et al. 2021; and Choi et al. 2022). Improvements have since been made to the design of fusion proteins for prime editing. For example, it has been reported that introducing various point mutations in the reverse transcriptase ("RT") portion can enhance RT activity (see Anzalone et al. 2019; Arezi & Hogrefe, *Nucl. Acids Res.* 2009, 473-481). Other studies have found that adding nuclear localization sequences (NLSs) to both the N- and C-terminus of a prime editor fusion protein enhances molecular transport of the relatively large protein into the cell nucleus, facilitating the editing of genomic DNA (see Liu et al. 2021).

Despite these advances, there exists a need in the art for further improvements to CRISPR technology and, in particular, for improvements to the efficiency and stability of CRISPR-based systems, e.g., to bolster the adoption of CRISPR-based gene editing as a therapeutic tool. In some aspects, the present disclosure addresses this and other needs. For example, methods described herein may be practiced in combination with methods for enhancing specificities for target sequences of interest.

BRIEF SUMMARY OF THE DISCLOSURE

The present disclosure provides chemically-modified CRISPR gRNAs (in particular prime editing guide RNAs (pegRNAs)) and related methods for editing a sequence of a target nucleic acid.

In a first general aspect, the disclosure provides a prime-editing guide RNA (pegRNA) comprising: a guide sequence that is complementary to a target DNA sequence of a nucleic acid; a sequence capable of interacting with a CRISPR-associated (Cas) protein, wherein the Cas protein is capable of nicking the complementary strand of the target sequence; a reverse transcriptase template sequence (RTT sequence) comprising one or more edits to a sequence of the nucleic acid; a primer-binding site sequence (PBS sequence) capable of hybridizing to the complementary strand of the target sequence (i.e., the nicked strand); wherein the pegRNA comprises a 5' end and a 3' end (one of which is a prime editing end and other is referred to as a "distal end"), and one or more modified nucleotides within 5 nucleotides of the prime editing end, wherein each modified nucleotide is a nucleotide comprising a 2' modification selected from 2'-O-methoxyethyl (2'-MOE), 2'-fluoro, 2'-O-methyl and 2'-deoxy, and an internucleotide linkage modification selected from 3'-phosphorothioate, 3'-phosphonocarboxylate, and 3'-thiophosphonocarboxylate.

In a second general aspect, the disclosure provides a method of editing a sequence of a nucleic acid, the method comprising: a) contacting the nucleic acid with a Cas protein capable of nicking a single strand of the nucleic acid; a reverse transcriptase; and a pegRNA comprising a guide sequence that is complementary to a target sequence of the nucleic acid, a sequence that interacts with the Cas protein, a primer-binding site sequence that can bind to the complementary strand of the target sequence, and a reverse transcriptase template sequence that comprises one or more edits to the sequence of the nucleic acid; wherein the guide RNA comprises a 5' end and a 3' end, and one or more modified nucleotides within 5 nucleotides of a prime editing end; and b) generating an edited nucleic acid by incorporating the one or more edits into the sequence of the nucleic acid, wherein each edit comprises one or more nucleotide substitutions, an insertion of one or more nucleotides, and/or a deletion of one or more nucleotides.

In a third general aspect, the disclosure provides a method of editing at least two different nucleic acid targets. The method employs two different pegRNAs that recognize different target sequences and operates in generally the same manner as described above. A single Cas protein can be used, or alternatively two different Cas proteins, each for one of the pegRNAs, can be used. Similarly, multiplexing with more than two pegRNAs, such as 3, 4, 5, 6, 10, 20 or more, is conceivable in view of the present invention.

In some aspects of the various exemplary embodiments described herein, the one or more modified nucleotides within 5 nucleotides of the 3' and/or 5' end of the pegRNA comprise: 1) 0, 1, 2, 3, 4, or 5 MS nucleotides; 2) 0, 1, 2, 3, 4, or 5 MP or MSP nucleotides; or 3) or any combination of up to 5 MS and MP/MSP nucleotides (e.g., 0×MS, 5×MP; 1×MS, 4×MP; 2×MS, 3×MP; 3×MS, 2×MP; 4×MS, 1×MP; or 5×MS, 0×MP). In some aspects, the one or more modified nucleotides within 5 nucleotides of the 3' or 5' end of the pegRNA comprise: at least 1, 2, 3, 4, or 5 MS nucleotides, and/or at least 1, 2, 3, 4, or 5 MP or MSP nucleotides. The one or more modified nucleotides within 5 nucleotides of the 3' or 5' end of the pegRNA may comprise MS and MP/MSP nucleotides arranged in any order (e.g., MS, MS, MP, MS, MS; MP, MP, MP, MS, MS; MS, MS, MS; or MP, MP). The one or more modified nucleotides within 5 nucleotides of the 3' or 5' end of the pegRNA may be independently selected (e.g., the sequence of modified nucleotides may be different on the 5' and the 3' end of the pegRNA). In some aspects, the pegRNA comprises one or more modified nucleotides within 5 nucleotides of the 3' end (and/or within 5 nucleotides of the 5' end), wherein each modified nucleotide is a nucleotide comprising a 2' modification selected from 2'-O-methoxyethyl (2'-MOE), 2'-fluoro, 2'-O-methyl and 2'-deoxy, and an internucleotide linkage modification selected from 3'-phosphorothioate, 3'-phosphonocarboxylate, and 3'-thiophosphonocarboxylate.

Other objects, features, and advantages of the present disclosure will be apparent to one of skill in the art from the following detailed description and figures.

DESCRIPTION OF THE FIGURES

FIG. 11 illustrates prime editing of EMX1 and RUNX1 using exemplary target sequences.

FIG. 16A shows Cas9 style pegRNA with the editing element at the 3' end; FIG. 16B shows Cas9 style pegRNA with the editing element at the 5' end; FIG. 16C shows Cpf1 style pegRNA with the editing element at the 5' end; and FIG. 16D shows Cpf1 style pegRNA with the editing element at the 3' end.

DETAILED DESCRIPTION

Figure 1:
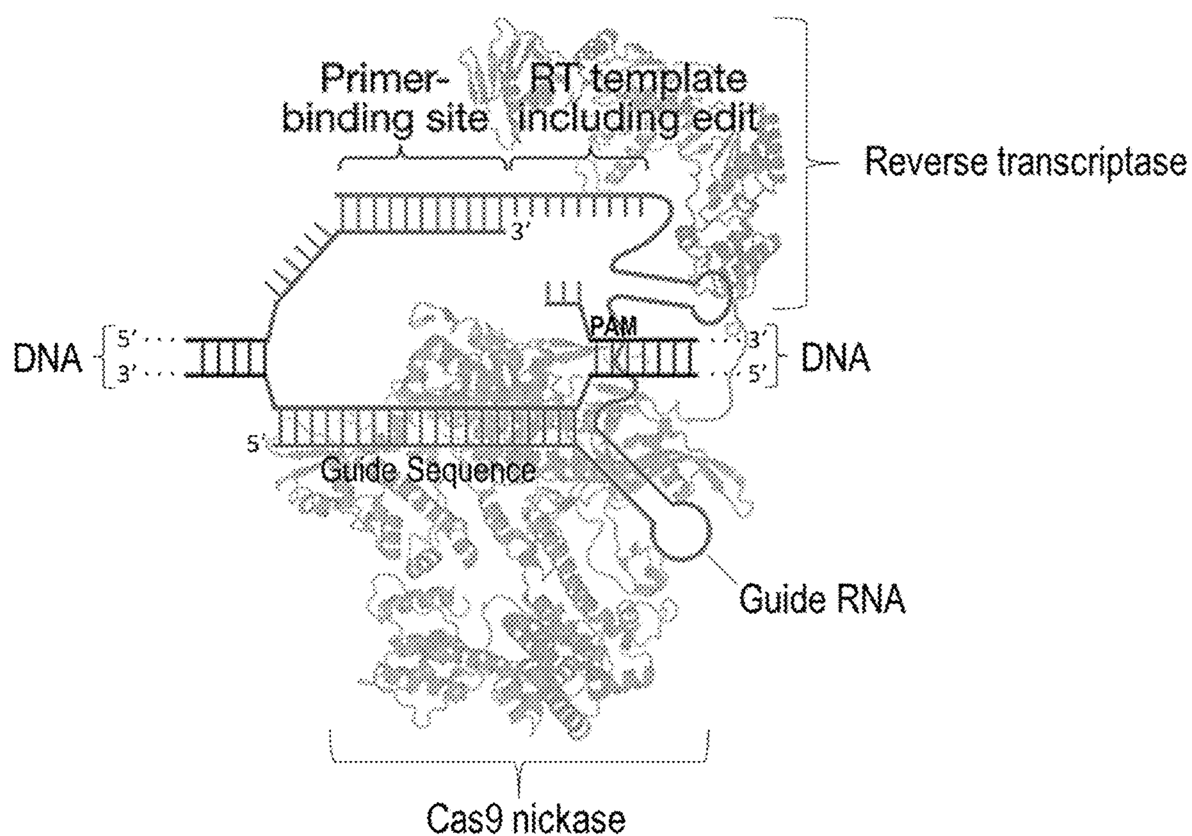
FIG. 1 is an illustration depicting prime editing using an exemplary CRISPR-Cas system.

Provided herein are methods for CRISPR/Cas-based genome editing in vitro (e.g., in a cultured cell; one example is a primary cell for use in ex vivo therapy) or in vivo (e.g., a cell in an organ or tissue of a subject such as a human). In particular, the methods provided herein utilize chemically-modified guide RNAs (gRNAs) for prime editing (pegRNAs) having enhanced activity for prime editing compared to corresponding unmodified pegRNAs. In some aspects, the present disclosure provides methods for editing a sequence of a target nucleic acid by introducing a prime editor and a chemically-modified pegRNA that hybridizes to the target nucleic acid. The prime editor comprises a Cas protein and a reverse transcriptase activity. The Cas protein may be provided as, for example, a Cas protein, an mRNA encoding a Cas protein, or a recombinant expression vector comprising a nucleotide sequence encoding a Cas protein. In some aspects, the Cas protein may be a variant that possesses single-strand nuclease activity (e.g., nickase activity). In some aspects, the Cas protein is provided as a fusion protein that incorporates reverse transcriptase activity. In certain other aspects, the present disclosure provides methods for preventing or treating a genetic disease in a subject by administering a sufficient amount of the chemically modified pegRNA and a prime editor, to correct a genetic mutation associated with the disease (e.g., by editing the genomic DNA of a patient).

Aspects of the present disclosure employ conventional techniques of immunology, biochemistry, chemistry, molecular biology, microbiology, cell biology, genomics and recombinant DNA, which are within the skill of the art. See Sambrook, Fritsch and Maniatis, *Molecular Cloning: A Laboratory Manual,* 2nd edition (1989), *Current Protocols in Molecular Biology* (F. M. Ausubel, et al. eds., (1987)), the series Methods in Enzymology (Academic Press, Inc.): PCR 2*: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)).

Oligonucleotides can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., denaturing polyacrylamide gel electrophoresis or anion-exchange high performance liquid chromatography (HPLC) as described in Pearson and Reanier, *J. Chrom.* 255: 137-149 (1983).

Definitions and Abbreviations

Unless specifically indicated otherwise, all technical and scientific terms used herein have the same meaning as commonly understood by those of ordinary skill in the art. In addition, any method or material similar or equivalent to a method or material described herein can be used in the practice of the methods and preparation of the compositions described herein. For purposes of the present disclosure, the following terms are defined.

The terms “a,” “an,” or “the” as used herein not only include aspects with one member, but also include aspects with more than one member. For instance, the singular forms “a,” “an,” and “the” include plural referents unless the context clearly dictates otherwise. Thus, for example, reference to “a cell” includes a plurality of such cells and reference to “the agent” includes reference to one or more agents known to those skilled in the art, and so forth.

The term “CRISPR-associated protein” or “Cas protein” or “Cas polypeptide” refers to a wild type Cas protein, a fragment thereof, or a mutant or variant thereof. The term “Cas mutant” or “Cas variant” refers to a protein or polypeptide derivative of a wild type Cas protein, e.g., a protein having one or more point mutations, insertions, deletions, truncations, a fusion protein, or a combination thereof. In certain embodiments, the “Cas mutant” or “Cas variant” substantially retains the nuclease activity of the Cas protein. In certain embodiments, the “Cas mutant” or “Cas variant” is mutated such that one or both nuclease domains are inactive (this protein may be referred to as a Cas nickase or dead Cas protein, respectively). In certain embodiments, the “Cas mutant” or “Cas variant” has nuclease activity. In certain embodiments, the “Cas mutant” or “Cas variant” lacks some or all of the nuclease activity of its wild-type counterpart. The term “CRISPR-associated protein” or “Cas protein” also includes a wild type Cpf1 protein, also referred to as Cas12a, of various species of prokaryotes (and named for Clustered Regularly Interspaced Short Palindromic Repeats from *Prevotella* and *Francisella* 1 ribonucleoproteins or CRISPR/Cpf1 ribonucleoproteins), a fragment thereof, or a mutant or variant thereof. Cas protein includes any of the CRISPR-associated proteins, including but not limited to any one in the six different CRISPR systems: Type I, Type II, Type III, Type IV, Type V, and Type VI.

The term “nuclease domain” of a Cas protein refers to the polypeptide sequence or domain within the protein which possesses the catalytic activity for DNA cleavage. Cas9 typically catalyzes a double-stranded break upstream of the PAM sequence. A nuclease domain can be contained in a single polypeptide chain, or cleavage activity can result from the association of two (or more) polypeptides. A single nuclease domain may consist of more than one isolated stretch of amino acids within a given polypeptide. Examples of these domains include RuvC-like motifs (amino acids 7-22, 759-766 and 982-989 in SEQ ID NO: 1) and HNH motifs (amino acids 837-863); see Gasiunas et al. (2012) *Proc. Natl. Acad. Sci.* USA 109:39, E2579-E2586 and WO/2013176772.

A synthetic guide RNA (“gRNA”) that has “gRNA functionality” is one that has one or more of the functions of naturally occurring guide RNA, such as associating with a Cas protein to form a ribonucleoprotein (RNP) complex, or a function performed by the guide RNA in association with a Cas protein (i.e., a function of the RNP complex). In certain embodiments, the functionality includes binding a target polynucleotide. In certain embodiments, the functionality includes targeting a Cas protein or a gRNA:Cas protein complex to a target polynucleotide. In certain embodiments, the functionality includes nicking a target polynucleotide. In certain embodiments, the functionality includes cleaving a target polynucleotide. In certain embodiments, the functionality includes associating with or binding to a Cas protein. For example, the Cas protein may be engineered to be a “dead” Cas protein (dCas) fused to one or more proteins or portions thereof, such as a transcription factor enhancer or repressor, a deaminase protein, a reverse transcriptase, a polymerase, etc., such that the fused protein(s) or portion(s) thereof can exert its functions at the target site. In certain embodiments, the functionality is any other known function of a guide RNA in a CRISPR-Cas system with a Cas protein, including an artificial CRISPR-Cas system with an engineered Cas protein. In certain embodiments, the functionality is any other function of natural guide RNA. The synthetic guide RNA may have gRNA functionality to a greater or lesser extent than a naturally occurring guide RNA. In certain embodiments, a synthetic guide RNA may have greater activities as to one function and lesser activities as to another function in comparison to a similar naturally occurring guide RNA.

A Cas protein having a single-strand "nicking" activity refers to a Cas protein, including a Cas mutant or Cas variant, that has reduced ability to cleave one of two strands of a dsDNA as compared to a wild type Cas protein. For example, in certain embodiments, a Cas protein having a single-strand nicking activity has a mutation (e.g., amino acid substitution) that reduces the function of the RuvC domain (or the HNH domain) and as a result reduces the ability to cleave one strand of the target DNA. Examples of such variants include the D10A, H839A/H840A, and/or N863A substitutions in *S. pyogenes* Cas9, and also include the same or similar substitutions at equivalent sites in Cas9 enzymes of other species.

A Cas protein having "binding" activity or that "binds" a target polynucleotide refers to a Cas protein which forms a complex with a guide RNA and, when in such a complex, the guide RNA hybridizes with another polynucleotide, such as a target polynucleotide sequence, via hydrogen bonding between the bases of the guide RNA and the other polynucleotide to form base pairs. The hydrogen bonding may occur by Watson-Crick base pairing or in any other sequence specific manner. The hybrid may comprise two strands forming a duplex, three or more strands forming a multi-stranded triplex, or any combination of these.

A "CRISPR system" is a system that utilizes at least one Cas protein and at least one gRNA to provide a function or effect, including but not limited to gene editing, DNA cleavage, DNA nicking, DNA binding, regulation of gene expression, CRISPR activation (CRISPRa), CRISPR interference (CRISPRi), and any other function that can be achieved by linking a Cas protein to another effector, thereby achieving the effector function on a target sequence recognized by the Cas protein. For example, a nuclease-free Cas protein can be fused to a transcription factor, a deaminase, a methylase, a reverse transcriptase, etc. The resulting fusion protein, in the presence of a guide RNA for the target, can be used to edit, regulate the transcription of, deaminate, or methylate, the target. As another example, in prime editing, a Cas protein is used with a reverse transcriptase or other polymerases (optionally as a fusion protein) to edit target nucleic acids in the presence of a pegRNA.

A "guide RNA" (or "gRNA") generally refers to an RNA molecule (or a group of RNA molecules collectively) that can bind to a Cas protein and aid in targeting the Cas protein to a specific location within a target polynucleotide (e.g. a DNA). Thus, a guide RNA comprises a guide sequence that can hybridize to a target sequence, and another part of the guide RNA (the "scaffold") functions to bind a Cas protein to form a ribonucleoprotein (RNP) complex of the guide RNA and the Cas protein. There are various styles of guide RNAs, including but not limited to the Cas9 style and the Cpf1 style of guide RNAs. A "Cas9 style" of guide RNA comprises a crRNA segment and a tracrRNA segment. As used herein, the term "crRNA" or "crRNA segment" refers to an RNA molecule or portion thereof that includes a polynucleotide-targeting guide sequence; a scaffold sequence which helps to interact with a Cas protein; and, optionally, a 5'-overhang sequence. As used herein, the term "tracrRNA" or "tracrRNA segment" refers to an RNA molecule or portion thereof that includes a protein-binding segment capable of interacting with a CRISPR-associated protein, such as a Cas9. In addition to Cas9, there are other Cas proteins employing the Cas9 style of guide RNAs, and the word "Cas9" is used in the term "Cas9 style" merely to specify a representative member of the various Cas proteins that employ this style. A "Cpf1 style" is a one-molecule guide RNA comprising a scaffold that is 5' to a guide sequence. In the literature, the Cpf1 guide RNA is often described as having only a crRNA but not a tracrRNA. It should be noted that, regardless of the terminology, all guide RNAs have a guide sequence to bind to the target, and a scaffold region that can interact with a Cas protein.

The term "guide RNA" encompasses a single-guide RNA ("sgRNA") that contains all functional parts in one molecule. For example, in a sgRNA of the Cas9 style, the crRNA segment and the tracrRNA segment are located in the same RNA molecule. As another example, the Cpf1 guide RNA is naturally a single-guide RNA molecule. The term "guide RNA" also encompasses, collectively, a group of two or more RNA molecules; for example, the crRNA segment and the tracrRNA segment may be located in separate RNA molecules.

Optionally, a "guide RNA" may comprise one or more additional segments that serve one or more accessory functions upon being recognized and bound by cognate polypeptides or enzymes that perform molecular functions alongside the function of the Cas protein associated with the gRNA. For example, a gRNA for prime editing (which is commonly referred to as a "pegRNA") may comprise a primer binding site and a reverse transcriptase template, as described in more detail in this disclosure. In another example, the gRNA may comprise one or more polynucleotide segments that form one or more aptamers that recognize and bind aptamer-binding polypeptides (optionally fused to other polypeptides) that serve accessory functions alongside the Cas protein functions. Optionally, a "guide RNA" may comprise an additional polynucleotide segment (such as a 3'-terminal polyuridine tail) that can increase the stability of the gRNA by impeding its degradation, as can occur for example by nucleases such as endonucleases and/or exonucleases.

The term "guide sequence" refers to a contiguous sequence of nucleotides in a gRNA (or pegRNA) which has partial or complete complementarity to a target sequence in a target polynucleotide and can hybridize to the target sequence by base pairing facilitated by a Cas protein. In some cases, a target sequence is adjacent to a PAM site (the PAM sequence). In some cases, the target sequence may be located immediately upstream of the PAM sequence. A target sequence, which hybridizes to the guide sequence, may be immediately downstream from the complement of the PAM sequence. In other examples such as Cpf1, the location of the target sequence, which hybridizes to the guide sequence, may be upstream from the complement of the PAM sequence.

A guide sequence can be as short as about 14 nucleotides and as long as about 30 nucleotides. Typical guide sequences are 15, 16, 17, 18, 19, 20, 21, 22, 23 and 24 nucleotides long. The length of the guide sequence varies across the two classes and six types of CRISPR-Cas systems mentioned above. Synthetic guide sequences for Cas9 are usually 20 nucleotides long, but can be longer or shorter. When a guide sequence is shorter than 20 nucleotides, it is typically a deletion from the 5'-end compared to a 20-nucleotide guide sequence. By way of example, a guide sequence may consist of 20 nucleotides complementary to a target sequence. In other words, the guide sequence is identical to the 20 nucleotides upstream of the PAM sequence, except the A/U difference between DNA and RNA. If this guide sequence is truncated by 3 nucleotides from the 5'-end, nucleotide 4 of the 20-nucleotide guide sequence now becomes nucleotide 1 in the 17-mer, nucleotide 5 of the 20-nucleotide guide sequence now becomes nucleotide 2 in the 17-mer, etc. The new position is the original position minus 3 for a 17-mer guide sequence.

As used herein, the term “prime editing guide RNA” (or “pegRNA”) refers to a guide RNA (gRNA) that comprises a reverse transcriptase template sequence encoding one or more edits to a target sequence of a nucleic acid, and a primer binding site that can bind to a sequence in the target region (also called a target site). For example, a pegRNA may comprise a reverse transcriptase template sequence comprising one or more nucleotide substitutions, insertions or deletions to a sequence in the target region. A pegRNA has the function of complexing with a Cas protein and hybridizing to a target sequence in a target region, usually in the genome of a cell, to result in editing of a sequence in the target region. In some embodiments, without being limited to a theory, the pegRNA forms an RNP complex with a Cas protein and binds the target sequence in the target region, the Cas protein makes a nick on one strand of the target region to result in a flap, the primer binding site of the pegRNA hybridizes with the flap, the reverse transcriptase uses the flap as a primer on the hybridized reverse transcriptase template of the pegRNA which serves as a template to synthesize a new DNA sequence onto the nicked end of the flap which then contains the desired edits, and ultimately, this new DNA sequence replaces an original sequence in the target region, resulting in editing of the target.

A pegRNA may comprise the reverse transcriptase template and primer binding site near its 5' end or 3' end. The “prime editing end” is one end of the pegRNA, either 5' or 3', that is closer to the reverse transcriptase template and primer binding site than to the guide sequence. The other end of the pegRNA is the “distal end”, which is closer to the guide sequence than to the reverse transcriptase template or primer binding site. Thus, the order of these components is, in either 5' or 3' orientation:

prime editing end-(primer binding site and reverse transcriptase template)-(guide sequence and scaffold)-distal end where the parentheses indicate that the two segments mentioned within could be switched in order with respect to each other, depending on the style of the pegRNA (e.g. Cas9 style or Cpf1 style) as well as the position of the prime editing end (i.e., a 5' end or a 3' end). It should be noted that if the pegRNA is not a single-guide RNA but comprises more than one RNA molecule, the prime editing end refers to the end closer to the primer binding site and reverse transcriptase template in the RNA molecule containing these components, whereas the opposite end of this RNA molecule is the distal end. The guide sequence may be in a different RNA molecule of the pegRNA, distinct from the RNA molecule bearing the prime editing end and the distal end.

Figure 16A:
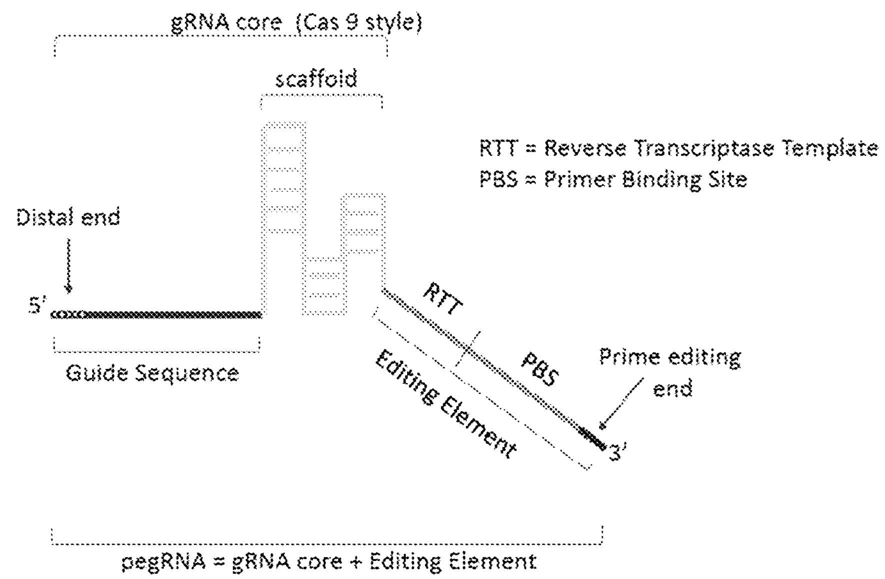
FIGS. 16A-16D illustrates the relative positions of the main components in various configurations.
Figure 16B:
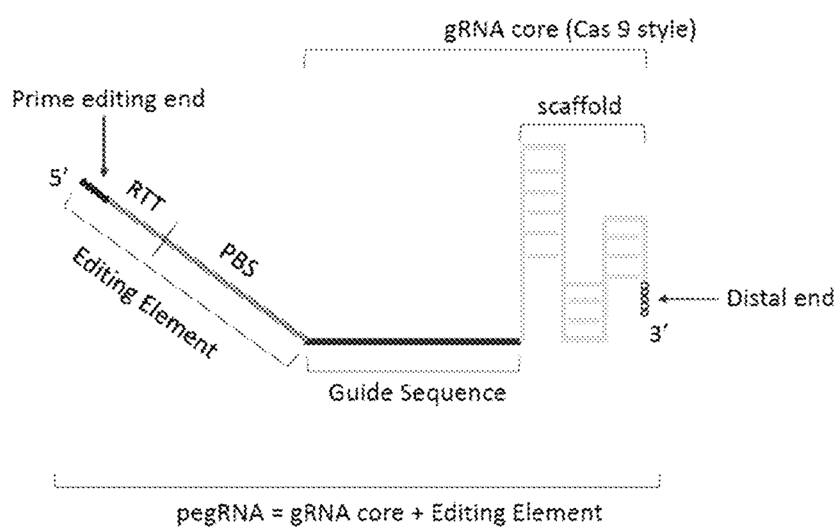
Figure 16C:
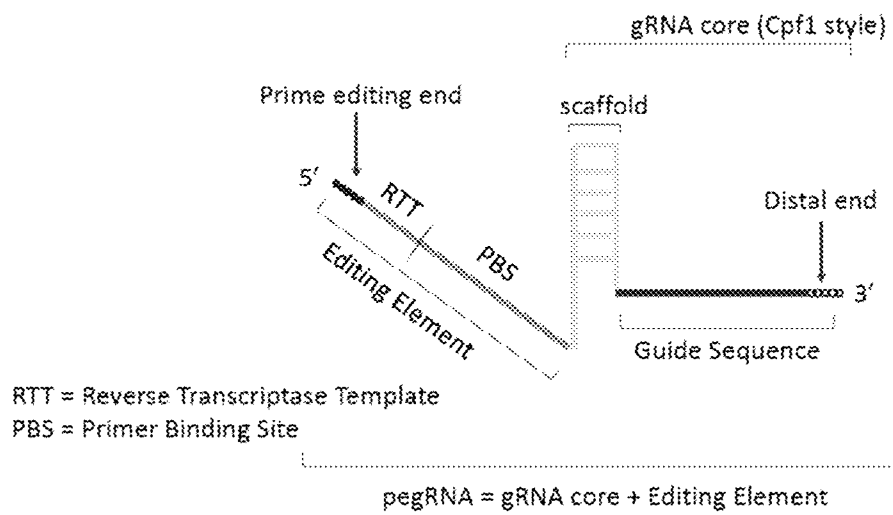
Figure 16D:
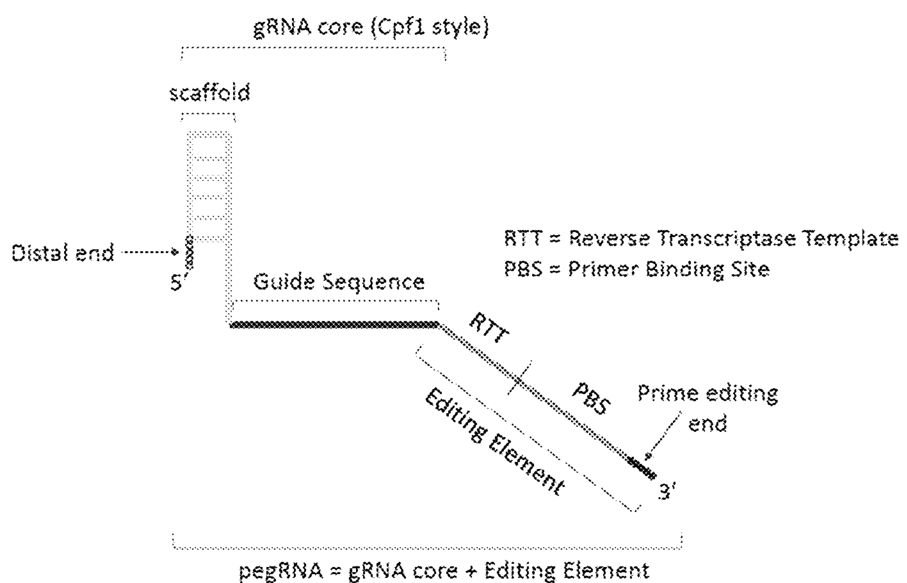

The position of the prime editing end relative to the other main components of pegRNAs is shown in more detail in FIGS. 16A-16D. FIGS. 16A and 16B illustrate the configuration of a Cas9 style pegRNA that has the prime editing end at either the 3' end or 5' end, respectively. FIGS. 16C and 16D illustrate the same for Cpf1 style pegRNAs.

A “prime editor” is a molecule, or a collection of multiple molecules, that has both Cas protein and reverse transcriptase activities. In some embodiments, the Cas protein is a nickase. In some embodiments, the prime editor is a fusion protein comprising both a Cas protein and a reverse transcriptase. As indicated elsewhere in this disclosure, other polymerases can be used in prime editing in lieu of a reverse transcriptase, so a prime editor may comprise a polymerase that is not a reverse transcriptase, in lieu of the RT. Different versions of prime editor have been developed and are referred to as PE1, PE2, PE3, etc. For example “PE2” refers to a PE complex comprising a fusion protein (PE2 protein) comprising a Cas9(H840A) nickase and a variant of MMLV RT having the following structure: [NLS]-[Cas9(H840A)]-[linker]-[MMLV_RT(D200N)(T330P)(L603W)(T306K)(W313F)], and a desired pegRNA. “PE3” refers to PE2 plus a second-strand nicking guide RNA that complexes with the PE2 protein and introduces a nick in the non-edited DNA strand in order to stimulate the cell into repairing the target region, which facilitates incorporation of the edits into the genome (see Anzalone et al. 2019; see Liu WO2020191153).

A “nicking guide RNA” or “nicking gRNA” is a guide RNA (not a pegRNA) that can be optionally added in prime editing to cause nicking of the strand that is not being edited, in or near the target region. Such nicking helps to stimulate the cell in which prime editing is taking place to repair the relevant area, i.e. the target region.

A “fusion protein” is a protein comprising at least two peptide sequences (i.e., amino acid sequences) covalently linked to each other, where the two peptide sequences are not covalently linked in nature. The two peptide sequences can be linked directly (with a bond in between) or indirectly (with a linker in between, wherein the linker may comprise any chemical structure, including but not limited to a third peptide sequence).

An “extension tail” is a stretch of nucleotides of 1, 2, 3, 4, 5, 6, 7, 8, 9, or 10 nucleotides that can be added to either the 5' end or 3' end of a guide RNA, such as a pegRNA. A “poly(N) tail” is a homopolymer extension tail, containing 1-10 nucleotides with the same nucleobase, for example A, U, C or T. A “polyuridine tail” or “polyU tail” is a poly(N) tail containing 1-10 uridines. Similarly, a “polyA tail” contains 1-10 adenosines.

The term “nucleic acid,” “nucleotide,” or “polynucleotide” refers to deoxyribonucleic acids (DNA), ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. In some embodiments, a nucleic acid can comprise a mixture of DNA, RNA and analogs thereof. Unless specifically limited, the term encompasses nucleic acids containing known analogs of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)). The term nucleic acid is used interchangeably with gene, cDNA, and mRNA encoded by a gene.

The term “nucleotide analog” or “modified nucleotide” refers to a nucleotide that contains one or more chemical modifications (e.g., substitutions), in or on the nitrogenous base of the nucleoside (e.g., cytosine (C), thymine (T) or uracil (U), adenine (A) or guanine (G)), in or on the sugar moiety of the nucleoside (e.g., ribose, deoxyribose, modified ribose, modified deoxyribose, six-membered sugar analog, or open-chain sugar analog), or the phosphate.

The term "gene" or "nucleotide sequence encoding a polypeptide" means the segment of DNA involved in producing a polypeptide chain. The DNA segment may include regions preceding and following the coding region (leader and trailer) involved in the transcription/translation of the gene product and the regulation of the transcription/translation, as well as intervening sequences (introns) between individual coding segments (exons).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "nucleic acid", "polynucleotide" or "oligonucleotide" refers to a DNA molecule, an RNA molecule, or analogs thereof. As used herein, the terms "nucleic acid", "polynucleotide" and "oligonucleotide" include, but are not limited to DNA molecules such as cDNA, genomic DNA or synthetic DNA and RNA molecules such as a guide RNA, messenger RNA or synthetic RNA. Moreover, as used herein, the terms include single-stranded and double-stranded forms.

The term "hybridization" or "hybridizing" refers to a process where completely or partially complementary polynucleotide strands come together under suitable hybridization conditions to form a double-stranded structure or a region in which the two constituent strands are joined by hydrogen bonds. As used herein, the term "partial hybridization" includes where the double-stranded structure or region contains one or more bulges or mismatches. Although hydrogen bonds typically form between adenine and thymine or adenine and uracil (A and T, or A and U, respectively) or cytosine and guanine (C and G), other non-canonical base pairs may form (see, e.g., Adams et al., "The Biochemistry of the Nucleic Acids," 11th ed., 1992). It is contemplated that modified nucleotides may form hydrogen bonds that allow or promote hybridization in a non-canonical way.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, the term "portion", "segment", "element", or "fragment" of a sequence refers to any portion of the sequence (e.g., a nucleotide subsequence or an amino acid subsequence) that is smaller than the complete sequence. Portions, segments, elements, or fragments of polynucleotides can be of any length that is more than 1, for example, at least 5, 10, 15, 20, 25, 30, 40, 50, 75, 100, 150, 200, 300 or 500 or more nucleotides in length.

The term "oligonucleotide" as used herein denotes a multimer of nucleotides. For example, an oligonucleotide may have about 2 to about 200 nucleotides, up to about 50 nucleotides, up to about 100 nucleotides, up to about 500 nucleotides in length, or any integer value between 2 and 500 in nucleotide number. In some embodiments, an oligonucleotide may be in the range of 30 to 300 nucleotides in length or 30 to 400 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51-60, 61 to 70, 71 to 80, 80 to 100, 100 to 150, 150 to 200, 200 to 250, 250 to 300, 300 to 350, or 350 to 400 nucleotides in length, for example, and any integer value in between these ranges.

A "recombinant expression vector" is a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators), as well as those that confer certain binding affinity or antigenicity to the recombinant protein produced from the expression vector.

"Recombinant" refers to a genetically modified polynucleotide, polypeptide, cell, tissue, or organism. For example, a recombinant polynucleotide (or a copy or complement of a recombinant polynucleotide) is one that has been manipulated using well known methods. A recombinant expression cassette comprising a promoter operably linked to a second polynucleotide (e.g., a coding sequence) can include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). A recombinant expression cassette (or expression vector) typically comprises polynucleotides in combinations that are not found in nature. For instance, human manipulated restriction sites or plasmid vector sequences can flank or separate the promoter from other sequences. A recombinant protein is one that is expressed from a recombinant polynucleotide, and recombinant cells, tissues, and organisms are those that comprise recombinant sequences (polynucleotide and/or polypeptide).

"Editing" a nucleic acid target means causing a change in the nucleotide sequence of the target. The change may be an insertion, deletion or substitution, each of a single nucleotide or multiple nucleotides. Where multiple nucleotides are inserted, deleted or substituted, the nucleotides may be consecutive or not consecutive. The change may be a combination of any of the above.

The term "single nucleotide polymorphism" or "SNP" refers to a change of a single nucleotide with a polynucleotide, including within an allele. This can include the replacement of one nucleotide by another, as well as deletion or insertion of a single nucleotide. Most typically, SNPs are biallelic markers although tri- and tetra-allelic markers can also exist. By way of non-limiting example, a nucleic acid molecule comprising SNP A\C may include a C or A at the polymorphic position.

The term "primary cell" refers to a cell isolated directly from a multicellular organism. Primary cells typically have undergone very few population doublings and are therefore more representative of the main functional component of the tissue from which they are derived in comparison to continuous (tumor or artificially immortalized) cell lines. In some cases, primary cells are cells that have been isolated and then used immediately. In other cases, primary cells cannot divide indefinitely and thus cannot be cultured for long periods of time in vitro.

The terms "culture," "culturing," "grow," "growing," "maintain," "maintaining," "expand," "expanding," etc., when referring to cell culture itself or the process of culturing, can be used interchangeably to mean that a cell (e.g., primary cell) is maintained outside its normal environment under controlled conditions, e.g., under conditions suitable for survival. Cultured cells are allowed to survive, and culturing can result in cell growth, stasis, differentiation or division. The term does not imply that all cells in the culture survive, grow, or divide, as some may naturally die or senesce. Cells are typically cultured in media, which can be changed during the course of the culture.

The terms "subject," "patient," and "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

As used herein, the term "administering" includes oral administration, topical contact, administration as a suppository, intravenous, intraperitoneal, intramuscular, intralesional, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "treating" refers to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "sufficient amount" refers to the amount of an agent (e.g., Cas protein, modified gRNA/pegRNA, etc.) that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other agents, timing of administration, and the physical delivery system in which it is carried.

As disclosed herein, a number of ranges of values are provided. It is understood that each intervening value between the upper and lower limits of that range is also specifically contemplated. Each smaller range or intervening value encompassed by a stated range is also specifically contemplated. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

Several chemically-modified nucleotides are described herein. Note that each of MS, MP, and MSP can mean the corresponding modification, or a nucleotide comprising the corresponding modification. The following abbreviations shall be used in relevant contexts:

"PACE": phosphonoacetate

"MS": 2'-O-methyl-3'-phosphorothioate

"MP": 2'-O-methyl-3'-phosphonoacetate

"MSP": 2'-O-methyl-3'-thiophosphonoacetate

"2'-MOE": 2'-O-methoxyethyl

Other definitions of terms may appear throughout the specification.

In recent years, CRISPR-based technologies have emerged as a potentially revolutionary therapy (e.g., for correcting genetic defects). However, the use of CRISPR systems has been limited due to practical concerns. In particular, there is a need for methods to stabilize the guide RNA (gRNA) for in vivo delivery of CRISPR-Cas components. Prior research has investigated the use of gRNAs having chemically-modified nucleotides. However, the structure of a traditional guide RNA (gRNA) is markedly different from that of a prime editing gRNA (pegRNA), and it was unclear, prior to the present disclosure, how chemical modifications of a pegRNA would impact its activity. In particular, pegRNAs contain additional sequences in their prime editing end compared to typical gRNAs (i.e., a reverse transcriptase template sequence and a primer binding site sequence) and the prime editing end of pegRNAs perform a different function than the corresponding end of typical gRNAs in other CRISPR-Cas systems. Thus, chemical modifications of nucleotides at the prime editing end of pegRNA have the potential to interfere with the role of the primer binding site sequence (which hybridizes to the nicked strand of the DNA target site, such that the reverse transcriptase recognizes the resulting RNA:DNA duplex as an acceptable substrate for primer extension from the 3' end of the nicked strand at the nicked site) or the reverse transcriptase template sequence (which serves as the template in the primer extension described above).

Based on this understanding, one would expect that chemical modifications, such as MS, MSP and MP, in the RNA segment of the RNA:DNA primer duplex may interfere with, or reduce, the affinity of the reverse transcriptase for this duplex and thus reduce or disable prime editing activity. Moreover, positions and/or combinations of positions of modified nucleotides (such as by MS, MSP or MP) might be expected to interfere with reverse transcriptase function in prime editing and thus reduce prime editing activity. A published co-crystal structure of a complex between an RNA:DNA duplex and a portion of the duplex-complexing polypeptide fragment of the reverse transcriptase from xenotropic murine leukemia virus-related virus, a close relative of the Moloney murine leukemia virus (MMLV) whose reverse transcriptase is usually employed in prime editing, lacks the portion of the reverse transcriptase that interacts with the 3' terminus of the RNA strand in the RNA:DNA duplex (Nowak et al., Nucl. Acids Res. 2013, 3874-3887), leaving the art with a lack of information about the RNA-protein contacts which may be important at the prime editing end of a pegRNA in prime editing.

The present disclosure is based in part on the surprising finding that MS or MP modifications can enhance prime editing activities. As discussed in further detail below, various designs of chemically-synthesized pegRNAs (having the 5'-guide sequence-scaffold-reverse transcriptase template-primer binding site-3' configuration), which typically range from about 120 to 150 nts long (and sometimes longer), were co-transfected with a prime editor mRNA in cultured human cells, and enhanced prime editing activity was observed when MS or MP modifications were added to phosphoriboses at the 3' end of the pegRNA. Notably, prime editing enhancement by MP was found to follow a distinct trend, different from that by MS. In some aspects, MP modifications provided, surprisingly, a higher level of enhancement when incorporated at the 3' end of the primer binding segment and where the pegRNA contains no added 3' extension such as a polyU tail. In contrast, MS modifications resulted in substantial enhancement at the 3' end of either terminal design, i.e., at the 3' end of the primer binding segment at the 3' terminus of the pegRNA, or at the 3' end of a polyU tail added downstream of the primer binding segment at the 3' terminus of the pegRNA (see below).

Exemplary synthetic pegRNAs are shown below in Tables 1 and 2. The 5' and 3' end modifications are indicated in the name of each synthetic pegRNA, which also indicates the target gene. For example, "EMX1-peg-3×MS,3×MP" refers to a pegRNA for the EMX1 gene with three MS modifications at the 5' end and three MP modifications at the 3' end of the pegRNA. The exact locations of the modifications are denoted by underlining in the sequences shown in Table 1. Some of the pegRNA designs have a short polyuridine tract (i.e., a polyU tail) added to the 3' terminus, as indicated by "+3'UU", "+3'UUU", or "+3'UUUU" in the pegRNA name.

TABLE 1

Exemplary synthetic pegRNAs targeting the EMX1 gene.

| SEQ ID NO. | pegRNA Name | 5' → 3' Sequence | Length (nt) |
|---|---|---|---|
| 1 | EMX1-peg-3xMS, 0xMS | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGGAC | 124 |
| 2 | EMX1-peg-3xMS, 3xMS | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUC**GGA**C | 124 |
| 3 | EMX1-peg + 3'UU-3xMS, 3xMS | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGG**ACU**U | 126 |
| 4 | EMX1-peg + 3'UUUU-3xMS, 3xMS | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGGAC**UUU**U | 128 |
| 5 | EMX1-peg-3xMS, 1xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGG**A**C | 124 |
| 6 | EMX1-peg-3xMS, 2xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCG**GA**C | 124 |
| 7 | EMX1-peg-3xMS, 3xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUC**GGA**C | 124 |

TABLE 1-continued

Exemplary synthetic pegRNAs targeting the EMX1 gene.

| SEQ ID NO. | pegRNA Name | 5' → 3' Sequence | Length (nt) |
|---|---|---|---|
| 8 | EMX1-peg + 3'UU-3xMS, 1xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGGACU**U**U | 126 |
| 9 | EMX1-peg + 3'UU-3xMS, 2xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGGA**CU**U | 126 |
| 10 | EMX1-peg + 3'UUU-3xMS, 2xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGGACU**UU**U | 127 |
| 11 | EMX1-peg + 3'UUUU-3xMS, 3xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGGACU**UUU**U | 128 |
| 12 | EMX1-peg + 3'UUUU-3xMS, 2xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGGACUU**UU**U | 128 |
| 13 | EMX1-peg + 3'UUUU-3xMS, 1xMP | **GAG**UCCGAGCAGAAGAAGAAGUUUUAGAGCUAGAAAUAGCAAGUUAAAAUAAGGCUAGUCCGUUAUCAACUUGAAAAAGUGGCACCGAGUCGGUGCAUGGGAGCACUUCUUCUUCUGCUCGGACUUU**U**U | 128 |

TABLE 2

Exemplary synthetic pegRNAs targeting the RUNX1 gene.

| SEQ ID NO. | pegRNA Name | 5' → 3' Sequence | Length (nt) |
|---|---|---|---|
| 14 | RUNX1-peg-3xMS, 0xMS | **GCA**UUUUCAGGAGGAAGCGAGUUUUAGAGCUAGAAAUAGCAAGUUAAAAUAAGGCUAGUCCGUUAUCAACUUGAAAAAGUGGCACCGAGUCGGUGCUGUCUGAAGCCAUCCAUGCUUCCUCCUGAAAAU | 129 |
| 15 | RUNX1-peg-3xMS, 3xMS | **GCA**UUUUCAGGAGGAAGCGAGUUUUAGAGCUAGAAAUAGCAAGUUAAAAUAAGGCUAGUCCGUUAUCAACUUGAAAAAGUGGCACCGAGUCGGUGCUGUCUGAAGCCAUCCAUGCUUCCUCCUGA**AAA**U | 129 |
| 16 | RUNX1-peg + UU-3xMS, 3xMS | **GCA**UUUUCAGGAGGAAGCGAGUUUUAGAGCUAGAAAUAGCAAGUUAAAAUAAGGCUAGUCCGUUAUCAACUUGAAAAAGUGGCACCGAGUCGGUGCUGUCUGAAGCCAUCCAUGCUUCCUCCUGAAA**AUU**U | 131 |
| 16 | RUNX1-peg + UUUU-3xMS, 3xMS | **GCA**UUUUCAGGAGGAAGCGAGUUUUAGAGCUAGAAAUAGCAAGUUAAAAUAAGGCUAGUCCGUUAUCAACUUGAAAAAGUGGCACCGAGUCGGUGCUGUCUGAAGCCAUCCAUGCUUCCUCCUGAAAAU**UUU**U | 133 |
| 18 | RUNX1-peg-3xMS, 1xMP | **GCA**UUUUCAGGAGGAAGCGAGUUUUAGAGCUAGAAAUAGCAAGUUAAAAUAAGGCUAGUCCGUUAUCAACUUGAAAAAGUGGCACCGAGUCGGUGCUGUCUGAAGCCAUCCAUGCUUCCUCCUGAAA**A**U | 129 |
| 19 | RUNX1-peg-3xMS, 2xMP | **GCA**UUUUCAGGAGGAAGCGAGUUUUAGAGCUAGAAAUAGCAAGUUAAAAUAAGGCUAGUCCGUUAUCAACUUGAAAAAGUGGCACCGAGUCGGUGCUGUCUGAAGCCAUCCAUGCUUCCUCCUGAA**AA**U | 129 |
| 20 | RUNX1-peg-3xMS, 3xMP | **GCA**UUUUCAGGAGGAAGCGAGUUUUAGAGCUAGAAAUAGCAAGUUAAAAUAAGGCUAGUCCGUU | 129 |

TABLE 2-continued

Exemplary synthetic pegRNAs targeting the RUNX1 gene.

| SEQ ID NO. | pegRNA Name | 5' → 3' Sequence | Length (nt) |
|---|---|---|---|
| | | AUCAACUUGAAAAAGUGGCACCGAGUCGGUGCU GUCUGAAGCCAUCCAUGCUUCCUCCUGAAAAU | |
| 21 | RUNX1-peg + UU-3xMS, 2xMP | GCAUUUUCAGGAGGAAGCGAGUUUUAGAGCUA GAAAUAGCAAGUUAAAAUAAGGCUAGUCCGUU AUCAACUUGAAAAAGUGGCACCGAGUCGGUGCU GUCUGAAGCCAUCCAUGCUUCCUCCUGAAAAUU U | 131 |
| 22 | RUNX1-peg + UUUU-3xMS, 3xMP | GCAUUUUCAGGAGGAAGCGAGUUUUAGAGCUA GAAAUAGCAAGUUAAAAUAAGGCUAGUCCGUU AUCAACUUGAAAAAGUGGCACCGAGUCGGUGCU GUCUGAAGCCAUCCAUGCUUCCUCCUGAAAAUU UUU | 133 |
| 23 | RUNX1-peg + UUUU-3xMS, 2xMP | GCAUUUUCAGGAGGAAGCGAGUUUUAGAGCUA GAAAUAGCAAGUUAAAAUAAGGCUAGUCCGUU AUCAACUUGAAAAAGUGGCACCGAGUCGGUGCU GUCUGAAGCCAUCCAUGCUUCCUCCUGAAAAUU UUU | 133 |
| 24 | RUNX1-peg + UUUU-3xMS, 1xMP | GCAUUUUCAGGAGGAAGCGAGUUUUAGAGCUA GAAAUAGCAAGUUAAAAUAAGGCUAGUCCGUU AUCAACUUGAAAAAGUGGCACCGAGUCGGUGCU GUCUGAAGCCAUCCAUGCUUCCUCCUGAAAAUU UUU | 133 |

Figure 2:
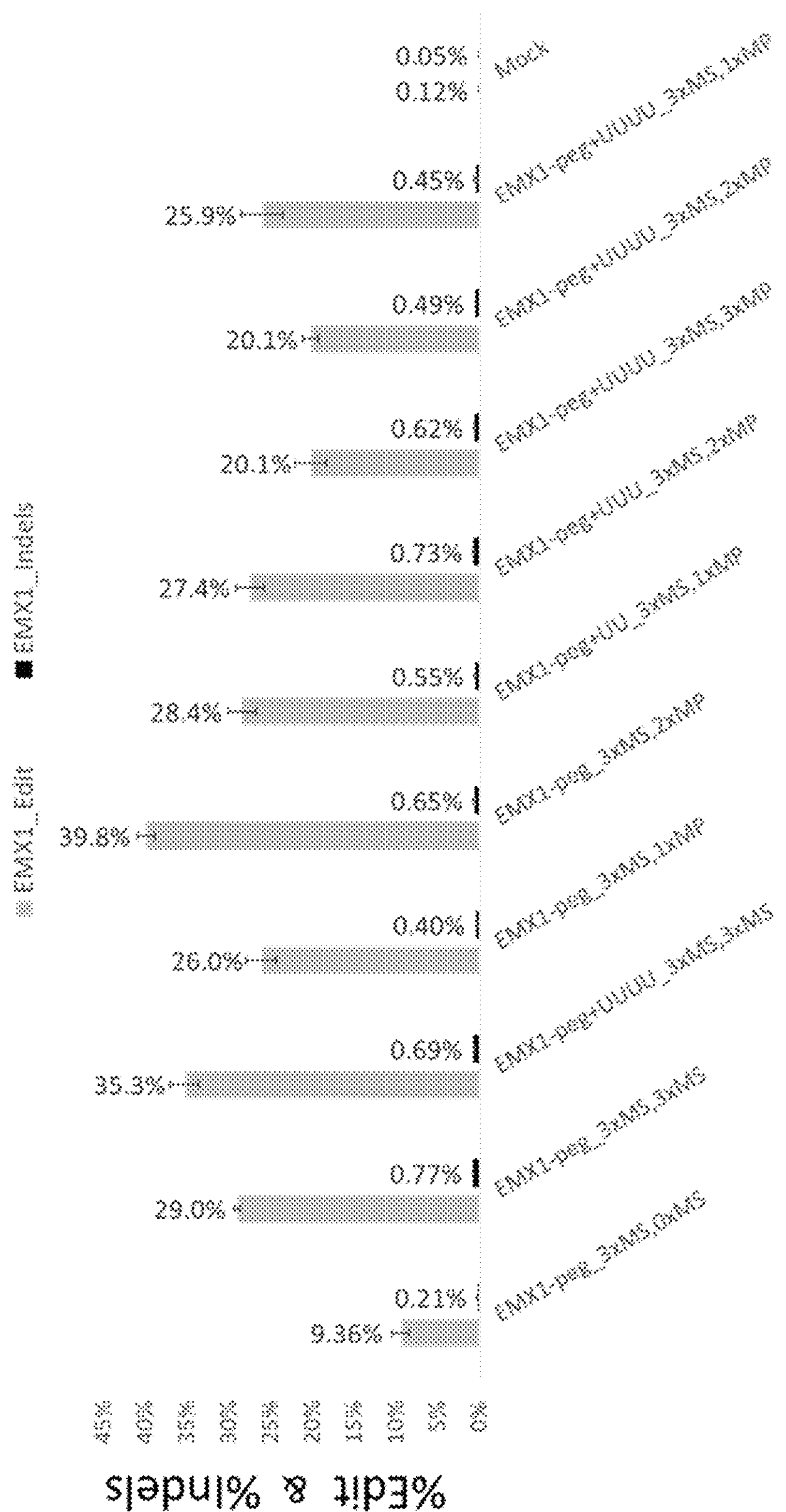
FIG. 2 is a graph showing the effectiveness of prime editing of EMX1 in K562 cells using an initial set of chemically-modified pegRNAs.
Figure 3:
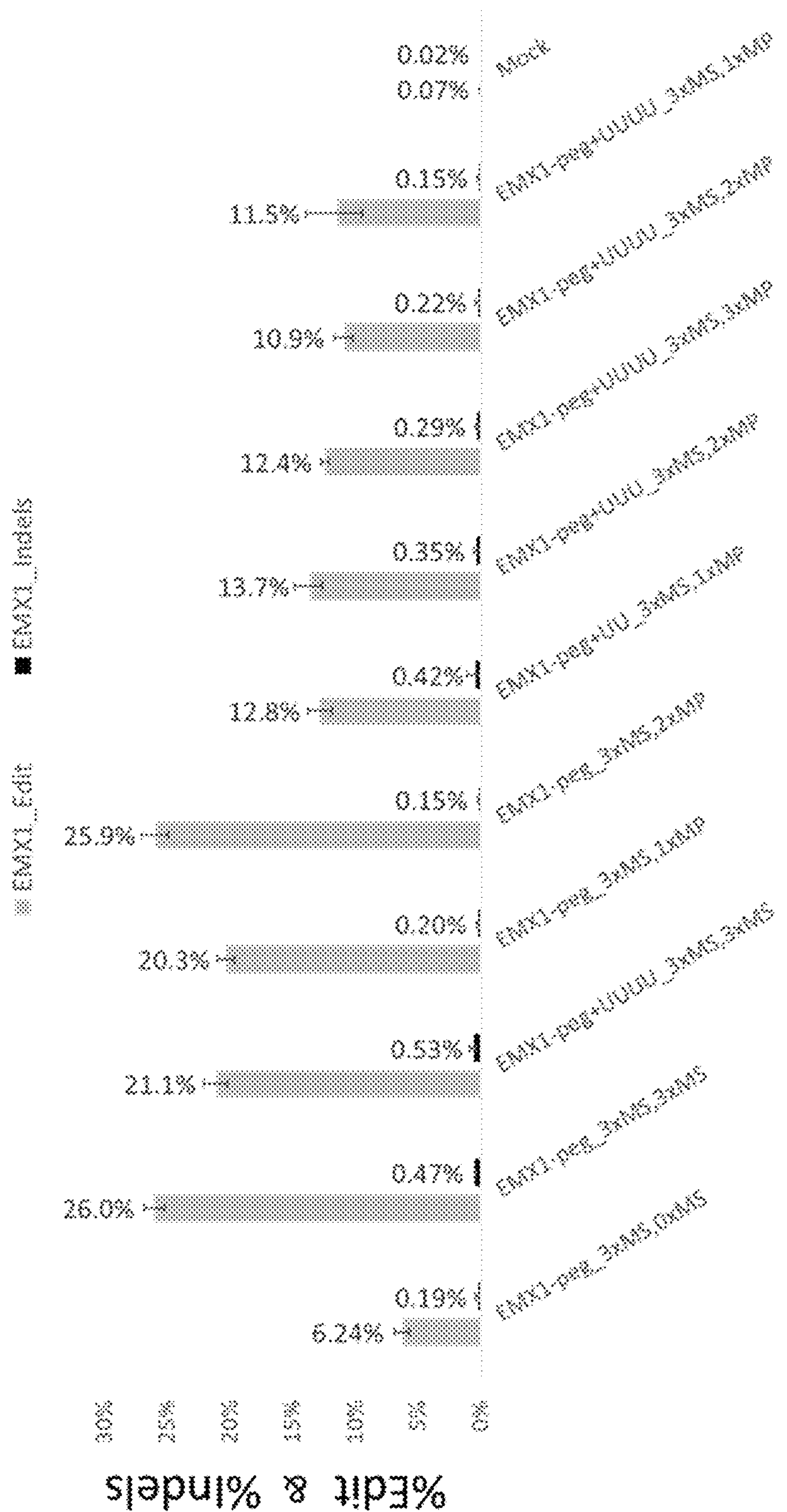
FIG. 3 is a graph showing the effectiveness of prime editing of EMX1 in Jurkat cells using an initial set of chemically-modified pegRNAs.

As demonstrated by FIGS. 2 and 3 and the examples described below, the use of chemical modifications at the 3' end of pegRNAs substantially improves the efficacy of synthetic pegRNAs with prime editors (with respect to pegRNAs that are unmodified at the 3' end). The use of synthetic pegRNAs for prime editing can be preferred when aiming to limit the duration of editing activity, as opposed to a sustained editing activity when pegRNAs and prime editors are constitutively expressed in cells transfected with DNA vectors as originally reported in the literature (see Anzalone et al. 2019). The present disclosure further demonstrates that certain chemical modifications and certain nucleotide positions in a pegRNA sequence can be especially advantageous, such as incorporating at least two MP modifications at the prime editing end of a pegRNA. In particular, MP has significant effects even without adding a polyU tail to the 3' terminus. Long RNA oligonucleotides such as pegRNAs are not easy to chemically synthesize, and any one additional nucleotide—which means one additional synthesis cycle—significantly reduces the yield of the full-length RNA. Therefore, modified pegRNAs that do not need extra nucleotides (such as the polyU tail) at the 3' end or any other places are very useful. Also, oligonucleotides with MP, MS or various other modifications described herein cannot be made by enzymatic transcription.

The significant effect of MP is consistent with our discovery that MP enhanced the half-life of guide RNAs. As described in Example 2 and Ryan et al. "Phosphonoacetate Modifications Enhance the Stability and Editing Yields of Guide RNAs for Cas9 Editors." Biochemistry (2022) doi.org/10.1021/acs.biochem.1c00768, guide RNAs with higher numbers of MP modifications at the 3' end are more stable than those with less MPs, while guide RNAs with MS modifications at the same positions are not as stable as the 1\H-containing counterparts.

In some aspects, the 3' or 5' end modifications described herein may optionally be combined with other modifications in the guide RNA, such as modifications in the guide sequence or scaffold. For instance, U.S. Pat. No. 10,767,175 teaches modifications that enhance target specificity. Thus, as an example, incorporating at least two MP modifications at consecutive 3' terminal phosphoriboses on a pegRNA strand that terminates with a primer binding segment at the 3' terminus (and without adding a downstream polyU tail to the 3' terminus) may be combined with MP or other modifications at position 5 or 11 in the 20-nucleotide guide sequence portion of a pegRNA.

The chemical modifications may be incorporated during chemical synthesis of gRNAs by using chemically-modified phosphoramidites at select cycles of amidite coupling for the desired sequence. Once synthesized, the chemically-modified gRNA is used in the same manner as unmodified gRNA for gene editing. In some aspects, a chemically-modified synthetic gRNA may be co-transfected with a Cas mRNA that expresses the prime editor in transfected cells. As demonstrated by the data provided herein, chemical modifications enhance the activity of the pegRNA in transfected cells, as introduced by electroporation, lipofection or exposure of live cells or tissues to nanoparticles charged with pegRNA, prime editor mRNA, and/or an additional gRNA.

A. Exemplary CRISPR/Cas Systems

The CRISPR/Cas system of genome modification includes a Cas protein (e.g., Cas9 nuclease) or a variant or fragment thereof, a DNA-targeting RNA (e.g., modified gRNA) containing a guide sequence that targets the Cas protein to the target genomic DNA and a scaffold sequence that interacts with the Cas protein (e.g., tracrRNA), and optionally, a donor repair template. In some instances, a variant of a Cas protein such as a Cas9 mutant containing one or more of the following mutations: D10A, H840A, D839A, and H863A, or a Cas9 nickase can be used. In other instances, a fragment of a Cas protein or a variant thereof with desired properties (e.g., capable of generating single- or double-strand breaks) can be used. The donor repair template can include a nucleotide sequence encoding a reporter polypeptide such as a fluorescent protein or an antibiotic resistance marker, and homology arms that are homologous to the target DNA and flank the site of gene modification. Alternatively, the donor repair template can be a single-stranded oligodeoxynucleotide (ssODN). In some aspects, a CRISPR/CAS system may include a Cas protein capable of acting as a prime editor (e.g., a fusion protein comprising a Cas protein which displays nickase activity fused to a reverse transcriptase protein or domain thereof). A prime editor may be used with a pegRNA, which incorporates a reverse transcriptase template containing one or more edits to the sequence of a target nucleic acid, in order to modify the sequence of the target nucleic acid by a process referred to as prime editing.

1. Cas proteins and Variants Thereof

The CRISPR (Clustered Regularly Interspaced Short Palindromic Repeats)/Cas (CRISPR-associated protein) nuclease system was discovered in bacteria but has been used in eukaryotic cells (e.g. mammalian) for genome editing. It is based on part of the adaptive immune response of many microbial bacteria and archaea. When a virus or plasmid invades a microbe, segments of the invader's DNA are incorporated into a CRISPR locus (or "CRISPR array") in the microbial genome. Expression of the CRISPR locus produces non-coding CRISPR RNAs (crRNA). In Type II CRISPR systems, the crRNA then associates, through a region of partial complementarity, with another type of RNA called tracrRNA to guide the Cas (e.g., Cas9) protein to a region homologous to the crRNA in the target DNA called a "protospacer." The Cas (e.g., Cas9) protein cleaves the DNA to generate blunt ends at the double-strand break at sites specified by a 20-nucleotide guide sequence contained within the crRNA transcript. The Cas (e.g., Cas9) protein requires both the crRNA and the tracrRNA for site-specific DNA recognition and cleavage. This system has been engineered such that the crRNA and tracrRNA can be combined into one molecule (a single guide RNA or "sgRNA") (see, e.g., Jinek et al. (2012) *Science,* 337:816-821; Jinek et al. (2013) *eLife,* 2:e00471; Segal (2013) *eLife,* 2:e00563). Thus, the CRISPR/Cas system can be engineered to create a double-strand break at a desired target in a genome of a cell, and harness the cell's endogenous mechanisms to repair the induced break by homology-directed repair (HDR) or non-homologous end-joining (NHEJ).

In some embodiments, the Cas protein has DNA cleavage activity. The Cas protein can direct cleavage of one or both strands at a location in a target DNA sequence. For example, the Cas protein can be a nickase having one or more inactivated catalytic domains that cleaves a single strand of a target DNA sequence (e.g., as in the case of a prime editor Cas protein).

Non-limiting examples of Cas proteins include Cas1, Cas1B, Cas2, Cas3, Cas4, Cas5, Cash, Cas7, Cas8, Cas9 (also known as Csn1 and Csx12), Cas10, Cash 1, Cas12, Cas13, Cas14, CasΦ, CasX, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Cpf1, Csb1, Csb2, Csb3, Csx17, Csx14, Csx10, Csx16, CsaX, Csx3, Csx1, Csx15, Csf1, Csf2, Csf3, Csf4, homologs thereof, variants thereof, fragments thereof, mutants thereof, and derivatives thereof. There are at least six types of Cas protein (Types I-VI), and at least 33 subtypes (see, e.g., Makarova et al., *Nat. Rev. Microbiol.,* 2020, 18:2, 67-83). Type II Cas proteins include Cas1, Cas2, Csn2, and Cas9. Cas proteins are known to those skilled in the art. For example, the amino acid sequence of the *Streptococcus pyogenes* wild-type Cas9 polypeptide is set forth, e.g., in NBCI Ref. Seq. No. NP 269215, and the amino acid sequence of *Streptococcus thermophilus* wild-type Cas9 polypeptide is set forth, e.g., in NBCI Ref. Seq. No. WP_011681470. CRISPR-related endonucleases that are useful in aspects of the present disclosure are disclosed, e.g., in U.S. Pat. Nos. 9,267,135; 9,745,610; and 10,266,850.

Cas proteins, e.g., Cas9 polypeptides, can be derived from a variety of bacterial species including, but not limited to, *Veillonella atypical, Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus coryniformis* subsp. *Torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *Succinogenes, Bacteroides Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes*, and *Francisella novicida.*

"Cas9" refers to an RNA-guided double-stranded DNA-binding nuclease protein or nickase protein. Wild-type Cas9 nuclease has two functional domains, e.g., RuvC and HNH, that cut different DNA strands. Cas9 can induce double-strand breaks in genomic DNA (target DNA) when both functional domains are active. The Cas9 enzyme can comprise one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor*, and *Campylobacter*. In some embodiments, the two catalytic domains are derived from different bacterial species.

Useful variants of the Cas9 protein can include a single inactive catalytic domain, such as a RuvC$^-$ or HNH$^-$ enzymes, both of which are nickases. Such Cas proteins are useful, e.g., in the context of prime editing. A Cas9 nickase has only one active functional domain and can cut only one strand of the target DNA, thereby creating a single-strand break or nick. In some embodiments, the Cas protein is a mutant Cas9 nuclease having at least a D10A mutation, and is a Cas9 nickase. In other embodiments, the Cas protein is a mutant Cas9 nuclease having at least a H840A mutation, and is a Cas9 nickase. Other examples of mutations present in a Cas9 nickase include, without limitation, N854A and N863A. A double-strand break can be introduced using a Cas9 nickase if at least two DNA-targeting RNAs that target opposite DNA strands are used. A staggered double-nick-induced double-strand break can be repaired by NHEJ or HDR (Ran et al., 2013, Cell, 154:1380-1389; Anzalone et al. *Nature* 576:7785, 2019, 149-15). This gene editing strategy favors HDR and decreases the frequency of indel mutations as byproducts. Non-limiting examples of Cas9 nucleases or nickases are described in, for example, U.S. Pat. Nos. 8,895,308; 8,889,418; 8,865,406; 9,267,135; and 9,738,908; and in U.S. Patent Application Pub. No. 2014/0186919. The Cas9 nuclease or nickase can be codon-optimized for the target cell or target organism.

In some embodiments, the Cas protein can be a Cas9 polypeptide that contains two silencing mutations of the RuvC1 and HNH nuclease domains (D10A and H840A), which is referred to as dCas9 (Jinek et al., *Science,* 2012, 337:816-821; Qi et al., *Cell,* 152(5):1173-1183). In one embodiment, the dCas9 polypeptide from *Streptococcus pyogenes* comprises at least one mutation at position D10, G12, G17, E762, H840, N854, N863, H982, H983, A984, D986, A987 or any combination thereof. Descriptions of such dCas9 polypeptides and variants thereof are provided in, for example, International Patent Pub. No. WO 2013/176772. The dCas9 enzyme can contain a mutation at D10, E762, H983 or D986, as well as a mutation at H840 or N863. In some instances, the dCas9 enzyme contains a D10A or D10N mutation. Also, the dCas9 enzyme can include a H840A, H840Y, or H840N. In some embodiments, the dCas9 enzyme used in aspects of the present disclosure comprises D10A and H840A; D10A and H840Y; D10A and H840N; D10N and H840A; D10N and H840Y; or D10N and H840N substitutions. The substitutions can be conservative or non-conservative substitutions to render the Cas9 polypeptide catalytically inactive and able to bind to target DNA.

The dCas9 polypeptide is catalytically inactive and lacks nuclease activity. In some instances, the dCas9 enzyme or a variant or fragment thereof can block transcription of a target sequence, and in some cases, block RNA polymerase. In other instances, the dCas9 enzyme or a variant or fragment thereof can activate transcription of a target sequence, for example, when fused to a transcriptional activator polypeptide. In some embodiments, the Cas protein or protein variants comprise one or more NLS sequences.

In some embodiments, a nucleotide sequence encoding the Cas protein is present in a recombinant expression vector. In certain instances, the recombinant expression vector is a viral construct, e.g., a recombinant adeno-associated virus construct, a recombinant adenoviral construct, a recombinant lentiviral construct, etc. For example, viral vectors can be based on vaccinia virus, poliovirus, adenovirus, adeno-associated virus, SV40, herpes simplex virus, human immunodeficiency virus, and the like. A retroviral vector can be based on Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, mammary tumor virus, and the like. Useful expression vectors are known to those of skill in the art, and many are commercially available. The following vectors are provided by way of example for eukaryotic host cells: pXT1, pSG5, pSVK3, pBPV, pMSG, and pSVLSV40. However, any other vector may be used if it is compatible with the host cell.

Any of the embodiments pertaining to a polypeptide, such as the Cas protein, the reverse transcriptase, or the fusion protein comprising the Cas protein and the reverse transcriptase, may include one or more Nuclear Localization Signal (NLS) sequence(s) in the polypeptide.

Depending on the target cell/expression system used, any of a number of transcription and translation control elements, including promoter, transcription enhancers, transcription terminators, and the like, may be used in the expression vector. Useful promoters can be derived from viruses, or any organism, e.g., prokaryotic or eukaryotic organisms. Suitable promoters include, but are not limited to, the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human H1 promoter (H1), etc.

The Cas protein and variants or fragments thereof can be introduced into a cell (e.g., an in vitro cell such as a primary cell for ex vivo therapy, or an in vivo cell such as in a patient) as a Cas polypeptide or a variant or fragment thereof, an mRNA encoding a Cas polypeptide or a variant or fragment thereof, or a recombinant expression vector comprising a nucleotide sequence encoding a Cas polypeptide or a variant or fragment thereof.

2. Chemically-Modified Guide RNA (gRNA) and Prime Editing Guide RNA (pegRNA)

The modified gRNAs for use in the CRISPR/Cas system of genome modification typically include a guide sequence that is complementary to a target nucleic acid sequence and a scaffold sequence that interacts with a Cas protein. The present disclosure provides modified pegRNAs with increased activity, stability, specificity, and/or decreased toxicity (e.g. immunogenicity) compared to corresponding unmodified pegRNAs. The advantages of the modified pegRNAs over the prior art can include, but are not limited to, greater ease of delivery into target cells such as primary cells, as well as increased stability, increased duration of activity, and/or reduced toxicity in the target cells. In some cases, the use of modified pegRNAs as part of the CRISPR/Cas system provide higher frequencies of on-target gene editing compared to other systems. In other cases, the modified pegRNAs provide improved activity and/or specificity compared to their unmodified sequence equivalents.

In certain instances, the modified pegRNA is complexed with a Cas protein (e.g., Cas9 polypeptide) or a variant or fragment thereof to form a ribonucleoprotein (RNP)-based delivery system before introduction into a cell (e.g., an in vitro cell such as a primary cell for ex vivo therapy, or an in vivo cell such as in a patient). In other instances, the modified gRNA is introduced into a cell (e.g., an in vitro cell such as a primary cell for ex vivo therapy, or an in vivo cell such as in a patient) with an mRNA encoding a Cas protein (e.g., Cas9 polypeptide) or a variant or fragment thereof. In yet other instances, the modified gRNA is introduced into a cell (e.g., an in vitro cell such as a primary cell for ex vivo therapy, or an in vivo cell such as in a patient) with a recombinant expression vector comprising a nucleotide sequence encoding a Cas protein (e.g., Cas9 polypeptide) or a variant or fragment thereof.

The guide sequence of the modified pegRNA can be any polynucleotide sequence having sufficient complementarity with a target polynucleotide sequence (e.g., target DNA sequence) to hybridize with the target sequence and direct sequence-specific binding of a CRISPR complex to the target sequence. In some embodiments, the degree of complementarity between a guide sequence of the modified pegRNA and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about 10, 11, 12, 13, 14, 15, 16, 17, 18, 19, 20, 21, 22, 23, 24, 25, 26, 27, 28, 29, 30, or more nucleotides in length. In some instances, a guide sequence is about 20 nucleotides in length. In other instances, a guide sequence is about 15 nucleotides in length. In other instances, a guide sequence is about 25 nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage or editing within the target sequence. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

The nucleotide sequence of a modified pegRNA can be selected using any of the web-based software described above. Considerations for selecting a DNA-targeting RNA include the PAM sequence for the Cas protein (e.g., Cas9 polypeptide) to be used, and strategies for minimizing off-target modifications. Tools, such as the CRISPR Design Tool, can provide sequences for preparing the modified gRNA, for assessing target modification efficiency, and/or assessing cleavage at off-target sites. Another consideration for selecting the sequence of a modified pegRNA includes reducing the degree of secondary structure within the guide sequence. Secondary structure may be determined by any suitable polynucleotide folding algorithm. Some programs are based on calculating the minimal Gibbs free energy. Examples of suitable algorithms include mFold (Zuker and Stiegler, *Nucleic Acids Res,* 9 (1981), 133-148), UNAFold package (Markham et al., Methods Mol Biol, 2008, 453:3-31) and RNAfold form the ViennaRNA Package.

One or more nucleotides of the guide sequence and/or one or more nucleotides of the scaffold sequence of the modified pegRNA can be a modified nucleotide. For instance, a guide sequence that is about 20 nucleotides in length may have 1 or more, e.g., 1, 2, 3, 4, 5, 6, 7, 8, 9, 10, 11, 12, 13, 14, 15, 16, 17, 18, 19, 20, or more modified nucleotides. In some cases, the guide sequence includes at least 2, 3, 4, 5, 6, 7, 8, 9, 10, or more modified nucleotides. In other cases, the guide sequence includes at least 2, 3, 4, 5, 6, 7, 8, 9, 10, 11, 12, 13, 14, 15, 16, 17, 19, 20, or more modified nucleotides. The modified nucleotides can be located at any nucleic acid position of the guide sequence. In other words, the modified nucleotides can be at or near the first and/or last nucleotide of the guide sequence, and/or at any position in between. For example, for a guide sequence that is 20 nucleotides in length, the one or more modified nucleotides can be located at nucleic acid position 1, position 2, position 3, position 4, position 5, position 6, position 7, position 8, position 9, position 10, position 11, position 12, position 13, position 14, position 15, position 16, position 17, position 18, position 19, and/or position 20 of the guide sequence. In certain instances, from about 10% to about 30%, e.g., about 10% to about 25%, about 10% to about 20%, about 10% to about 15%, about 15% to about 30%, about 20% to about 30%, or about 25% to about 30% of the guide sequence can comprise modified nucleotides. In other instances, from about 10% to about 30%, e.g., about 10%, about 11%, about 12%, about 13%, about 14%, about 15%, about 16%, about 17%, about 18%, about 19%, about 20%, about 21%, about 22%, about 23%, about 24%, about 25%, about 26%, about 2'7%, about 28%, about 29%, or about 30% of the guide sequence can comprise modified nucleotides.

In some embodiments, the scaffold sequence of the modified pegRNA contains one or more modified nucleotides. For example, a scaffold sequence that is about 80 nucleotides in length may have 1 or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 76, 77, 78, 79, 80, or more modified nucleotides. In some instances, the scaffold sequence includes at least 2, 3, 4, 5, 6, 7, 8, 9, 10, or more modified nucleotides. In other instances, the scaffold sequence includes at least 2, 3, 4, 5, 6, 7, 8, 9, 10, 11, 12, 13, 14, 15, 16, 17, 19, 20, or more modified nucleotides. The modified nucleotides can be located at any nucleic acid position of the scaffold sequence. For example, the modified nucleotides can be at or near the first and/or last nucleotide of the scaffold sequence, and/or at any position in between. For example, for a scaffold sequence that is about 80 nucleotides in length, the one or more modified nucleotides can be located at nucleic acid position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28, position 29, position 30, position 31, position 32, position 33, position 34, position 35, position 36, position 37, position 38, position 39, position 40, position 41, position 42, position 43, position 44, position 45, position 46, position 47, position 48, position 49, position 50, position 51, position 52, position 53, position 54, position 55, position 56, position 57, position 58, position 59, position 60, position 61, position 62, position 63, position 64, position 65, position 66, position 67, position 68, position 69, position 70, position 71, position 72, position 73, position 74, position 75, position 76, position 77, position 78, position 79, and/or position 80 of the sequence. In some instances, from about 1% to about 10%, e.g., about 1% to about 8%, about 1% to about 5%, about 5% to about 10%, or about 3% to about 7% of the scaffold sequence can comprise modified nucleotides. In other instances, from about 1% to about 10%, e.g., about 1%, about 2%, about 3%, about 4%, about 5%, about 6%, about 7%, about 8%, about 9%, or about 10% of the scaffold sequence can comprise modified nucleotides.

The modified nucleotides of the pegRNA can include a modification in the ribose (e.g., sugar) group, phosphate group, nucleobase, or any combination thereof. In some embodiments, the modification in the ribose group comprises a modification at the 2' position of the ribose.

In some embodiments, the modified nucleotide includes a 2' fluoro-arabino nucleic acid, tricycle-DNA (tc-DNA), peptide nucleic acid, cyclohexene nucleic acid (CeNA), locked nucleic acid (LNA), ethylene-bridged nucleic acid (ENA), xeno nucleic acid (XNA), a phosphodiamidate morpholino, or a combination thereof.

Modified nucleotides or nucleotide analogues can include sugar- and/or backbone-modified ribonucleotides (i.e., include modifications to the phosphate-sugar backbone). For example, the phosphodiester linkages of a native or natural RNA may be modified to include at least one of a nitrogen or sulfur heteroatom. In some backbone-modified ribonucleotides the phosphoester group connecting to adjacent ribonucleotides may be replaced by a modified group, e.g., of phosphorothioate group. In preferred sugar-modified ribonucleotides, the 2' moiety is a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In some embodiments, the modified nucleotide contains a sugar modification. Non-limiting examples of sugar modifications include 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), azidotriphosphate (2'-azido-2'-deoxycytidine-5'-triphosphate, 2'-azido-2'-deoxyuridine-5'-triphosphate), and combinations thereof.

In some embodiments, the modified pegRNA contains one or more 2'-fluro, 2'-amino and/or 2'-thio modifications. In some instances, the modification is a 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, 5-amino-allyl-uridine, 5-bromo-uridine, 5-iodo-uridine, 5-methyl-cytidine, ribo-thymidine, 2-aminopurine, 2'-amino-butyryl-pyrene-uridine, 5-fluoro-cytidine, and/or 5-fluoro-uridine.

There are more than 96 naturally occurring nucleoside modifications found on mammalian RNA. See, e.g., Limbach et al., *Nucleic Acids Research,* 22(12):2183-2196 (1994). The preparation of nucleotides and modified nucleotides and nucleosides are well-known in the art and described in, e.g., U.S. Pat. Nos. 4,373,071, 4,458,066, 4,500,707, 4,668,777, 4,973,679, 5,047,524, 5,132,418, 5,153,319, 5,262,530, and 5,700,642. Numerous modified nucleosides and modified nucleotides that are suitable for use as described herein are commercially available. The nucleoside can be an analogue of a naturally occurring nucleoside. In some cases, the analogue is dihydrouridine, methyl adenosine, methylcytidine, methyluridine, methylpseudouridine, thiouridine, deoxycytodine, and deoxyuridine.

In some cases, the modified pegRNA described herein includes a nucleobase-modified ribonucleotide, i.e., a ribonucleotide containing at least one non-naturally occurring nucleobase instead of a naturally occurring nucleobase. Non-limiting examples of modified nucleobases which can be incorporated into modified nucleosides and modified nucleotides include m5C (5-methylcytidine), m5U (5-methyluridine), m6A (N6-methyladenosine), s2U (2-thiouridine), Um (2'-O-methyluridine), m1A (1-methyl adenosine), m2A (2-methyladenosine), Am (2-1-O-methyladenosine), ms2m6A (2-methylthio-N6-methyladenosine), i6A (N6-isopentenyl adenosine), ms2i6A (2-methylthio-N6-isopentenyladenosine), io6A (N6-(cis-hydroxyisopentenyl) adenosine), ms2io6A (2-methylthio-N6-(cis-hydroxyisopentenyl)adenosine), g6A (N6-glycinylcarbamoyladenosine), t6A (N6-threonyl carbamoyladenosine), ms2t6A (2-methylthio-N6-threonyl carbamoyladenosine), m6t6A (N6-methyl-N6-threonylcarbamoyladenosine), hn6A(N6-hydroxynorvalylcarbamoyl adenosine), ms2hn6A (2-methylthio-N6-hydroxynorvalyl carbamoyladenosine), Ar(p) (2-O-ribosyladenosine(phosphate)), I (inosine), m11 (1-methylinosine), m'Im (1,2'-O-dimethylinosine), m3C (3-methylcytidine), Cm (2T methylcytidine), s2C (2-thiocytidine), ac4C (N4-acetylcytidine), f5C (5-fonnylcytidine), m5Cm (5,2-O-dimethylcytidine), ac4Cm (N4acetyl2TOmethylcytidine), k2C (lysidine), m1G (1-methylguanosine), m2G (N2-methylguanosine), m7G (7-methylguanosine), Gm (2'-O-methylguanosine), m22G (N2,N2-dimethylguanosine), m2Gm (N2,2'-O-dimethylguanosine), m22Gm (N2,N2,2'-O-trimethylguanosine), Gr(p) (2'-O-ribosylguanosine(phosphate)), yW (wybutosine), o2yW (peroxywybutosine), OHyW (hydroxywybutosine), OHyW* (undermodified hydroxywybutosine), imG (wyosine), mimG (methylguanosine), Q (queuosine), oQ (epoxyqueuosine), galQ (galtactosyl-queuosine), manQ (mannosyl-queuosine), preQo (7-cyano-7-deazaguanosine), preQi (7-aminomethyl-7-deazaguanosine), G (archaeosine), D (dihydrouridine), m5Um (5,2'-O-dimethyluridine), s4U (4-thiouridine), m5s2U (5-methyl-2-thiouridine), s2Um (2-thio-2'-O-methyluridine), acp3U (3-(3-amino-3-carboxypropyl)uridine), ho5U (5-hydroxyuridine), mo5U (5-methoxyuridine), cmo5U (uridine 5-oxyacetic acid), mcmo5U (uridine 5-oxyacetic acid methyl ester), chm5U (5-(carboxyhydroxymethyl)uridine)), mchm5U (5-(carboxyhydroxymethyl)uridine methyl ester), mcm5U (5-methoxycarbonyl methyluridine), mcm5Um (S-methoxycarbonylmethyl-2-O-methyluridine), mcm5 s2U (5-methoxycarbonylmethyl-2-thiouridine), nm5 s2U (5-aminomethyl-2-thiouridine), mnm5U (5-methylaminomethyluridine), mnm5s2U (5-methylaminomethyl-2-thiouridine), mnm5se2U (5-methylaminomethyl-2-selenouridine), ncm5U (5-carbamoylmethyl uridine), ncm5Um (5-carbamoylmethyl-2'-O-methyluridine), cmnm5U (5-carboxymethylaminomethyluridine), cnmm5Um (5-carboxymethylaminomethyl-2-L-Omethyluridine), cmnm5s2U (5-carboxymethylaminomethyl-2-thiouridine), m62A (N6, N6-dimethyladenosine), Tm (2'-O-methylinosine), m4C (N4-methylcytidine), m4Cm (N4,2-O-dimethylcytidine), hm5C (5-hydroxymethylcytidine), m3U (3-methyluridine), cm5U (5-carboxymethyluridine), m6Am (N6,T-O-dimethyladenosine), m62Am (N6,N6,O-2-trimethyladenosine), m2'7G (N2,7-dimethylguanosine), m2'2'7G (N2,N2,7-trimethylguanosine), m3Um (3,2T-O-dimethyluridine), m5D (5-methyldihydrouridine), f5Cm (5-formyl-2'-O-methylcytidine), m1Gm (1,2'-O-dimethylguanosine), m'Am (1,2-O-dimethyl adenosine)irinomethyluridine), tm5s2U (S-taurinomethyl-2-thiouridine)), imG-14 (4-demethyl guanosine), imG2 (isoguanosine), or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxy cytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza substituted guanine, 7-deaza-7-(C2-C6)

alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, and combinations thereof.

In some embodiments, the phosphate backbone of the modified pegRNA is altered. The modified gRNA can include one or more phosphorothioate, phosphoramidate (e.g., N3'-P5'-phosphoramidate (NP)), 2'-O-methoxy-ethyl (2'MOE), 2'-O-methyl-ethyl (2'ME), and/or methylphosphonate linkages.

In particular embodiments, one or more of the modified nucleotides of the guide sequence and/or one or more of the modified nucleotides of the scaffold sequence of the modified pegRNA include a 2'-O-methyl (M) nucleotide, a 2'-O-methyl-3'-phosphorothioate (MS) nucleotide, a 2'-O-methyl-3'-phosphonoacetate (MP) nucleotide, a 2'-O-methyl-3'thioPACE (MSP) nucleotide, or a combination thereof. In some instances, the modified pegRNA includes one or more MS nucleotides. In other instances, the modified pegRNA includes one or more MP nucleotides. In yet other instances, the modified pegRNA includes one or more MS nucleotides and one or more MP or MSP nucleotides. In certain instances, the modified pegRNA includes one or more MS nucleotides and/or one or more MSP nucleotides, and further includes one or more M nucleotides. In certain other instances, MS nucleotides and/or MP nucleotides are the only modified nucleotides present in the modified pegRNA.

In some aspects, the one or more modified nucleotides within 5 nucleotides of the 3' and/or 5' end of the modified pegRNA comprise: 1) 0, 1, 2, 3, 4, or 5 MS nucleotides; 2) 0, 1, 2, 3, 4, or 5 MP or MSP nucleotides; or 3) or any combination of up to 5 MS and MP/MSP nucleotides (e.g., 0×MS, 5×MP; 1×MS, 4×MP; 2×MS, 3×MP; 3×MS, 2×MP; 4×MS, 1×MP; or 5×MS, 0×MP). In some aspects, the one or more modified nucleotides within 5 nucleotides of the 3' or 5' end of the modified pegRNA comprise: at least 1, 2, 3, 4, or 5 MS nucleotides, and/or at least 1, 2, 3, 4, or 5 MP/MSP nucleotides. The one or more modified nucleotides within 5 nucleotides of the 3' or 5' end of the pegRNA may comprise MS and MP/MSP nucleotides arranged in any order (e.g., MS, MS, MP, MS, MS; MP, MP, MP, MS, MS; MS, MS, MS; or MP, MP). The one or more modified nucleotides within 5 nucleotides of the 3' or 5' end of the pegRNA may be independently selected (e.g., the sequence of modified nucleotides may be different on the 5' and the 3' end of the modified pegRNA). In some aspects, the modified pegRNA comprises one or more modified nucleotides within 5 nucleotides of the 3' end (and/or within 5 nucleotides of the 5' end), wherein each modified nucleotide is a nucleotide comprising a 2' modification selected from 2'-O-methoxy-ethyl (2'-MOE), 2'-fluoro, 2'-O-methyl and 2'-deoxy, and an internucleotide linkage modification selected from 3'-phosphorothioate, 3'-phosphonocarboxylate, and 3'-thiophosphoncarboxylate.

It should be noted that any of the modifications described herein may be combined and incorporated in the guide sequence and/or the scaffold sequence of the modified pegRNA.

In some cases, the modified pegRNA also includes a structural modification such as a stem loop, e.g., MS2 stem loop or tetraloop.

The modified pegRNA can be synthesized by any method known to one of ordinary skill in the art. Modified gRNAs can be synthesized using 2'-O-thionocarbamate-protected nucleoside phosphoramidites. Methods are described in, e.g., Dellinger et al., *J. American Chemical Society* 133, 11540-11556 (2011); Threlfall et al., *Organic & Biomolecular Chemistry* 10, 746-754 (2012); and Dellinger et al., *J. American Chemical Society* 125, 940-950 (2003).

3. Reverse Transcriptase Template and Primer Binding Site

The reverse transcriptase template and the primer binding site are important editing components of a pegRNA. The primer binding site can hybridize by complementarity to a sequence of the nicked target strand (the nick made by the Cas protein during prime editing) in the target region. In some embodiments, a Cas protein-reverse transcriptase fusion protein or related system (e.g., comprising a polymerase or a terminal nucleotidyltransferase instead of a reverse transcriptase) is brought to the target region by the guide sequence of a pegRNA, and generates a single-strand nick in the Cas9-bound target region, then uses the nicked DNA as a primer for reverse transcription encoded by the RT template in the pegRNA.

Thus, the pegRNA contains new genetic information in the reverse transcriptase template that encodes a replacement strand of DNA containing a desired genetic alteration, which is used to replace a corresponding endogenous DNA strand in the target region. To transfer information from the pegRNA to the target DNA, the mechanism of prime editing involves nicking one strand of the DNA target site to expose a 3'-hydroxyl group. In some embodiments, the exposed 3'-hydroxyl group is used to prime DNA polymerization on the reverse transcription template in the pegRNA. In various embodiments, the template for polymerization of the replacement strand containing the edit can be RNA or DNA, or a mixed sequence of both RNA and DNA nucleotides. With respect to pegRNA structure and segments (such as reverse transcriptase template, primer binding site, guide sequence, scaffold, optional linkers, etc.), the other components for prime editing (such as the Cas protein, reverse transcriptase, fusion protein of a Cas protein and a reverse transcriptase, optional linkers in the fusion protein, etc.), prime editing mechanism and operations, as well as variations thereof, PCT Publication Number WO2020191153 by David Liu et al. is hereby specifically incorporated by reference in its entirety.

In some embodiments, the primer binding site hybridizes to a sequence that begins next to the nick site and extends away from the nick site. In some other embodiments, the primer binding site hybridizes to a sequence that begins 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides apart from the nick site, and extends away from the nick site. In some embodiments, the primer binding site comprises 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides that are complementary to the target region. In some embodiments, the primer binding site is at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 30 nucleotides, or at least 40 nucleotides in length.

The reverse transcriptase template contains a sequence (the "edit region") that is the same as a sequence (the sequence of interest) in the target region, except that the reverse transcriptase template comprises at least one desired edit, i.e., a substitution, insertion or deletion of at least one nucleotide. The reverse transcriptase template may further comprise a homology region that is substantially identical to another sequence in the target region that is next to the sequence of interest. The edit region and the homology region may independently be at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 200 nucleotides, at least 300 nucleotides, at least 400 nucleotides, or at least 500 nucleotides in length. In some embodiments, the edit region and the homology region are, independently, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides in length.

The pegRNA comprises three main component elements with respect to their functions: (1) guide sequence, (2) scaffold (Cas protein interacting element), and (3) editing element (primer binding site and the reverse transcriptase template). These three main elements of the pegRNA can be ordered in two main configurations. The first configuration would position the editing element at the 3' end of the pegRNA, and for a Cas9 style pegRNA, the components are in the following order: 5'-guide sequence-scaffold-reverse transcriptase template-primer binding site-3'. For a Cpf1 style pegRNA, the order would be 5'-scaffold-guide sequence-reverse transcriptase template-primer binding site-3'.

The second configuration positions the editing element at the 5'-end of the pegRNA. For a Cas9 style pegRNA, the components would be in the following order: 5'-reverse transcriptase template-primer binding site-guide sequence-scaffold-3'. For a Cpf1 style pegRNA, the order would be 5'-reverse transcriptase template-primer binding site-scaffold-guide sequence-3'.

In all configurations, the editing element may be linked to the other part (comprising the guide sequence and scaffold), either directly through a phosphate internucleotide linkage or through a chemical linker such as (but not limited to) a polyethylene glycol (PEG) linker, a squaramide linker, a triazolo linker, an oligonucleotide linker or any other linker known in the art.

Furthermore, the reverse transcriptase template (including the homology region) and/or the primer binding site may be DNA or RNA, or may comprise a mixture of ribonucleotides and 2'-deoxyribonucleotides. Still further, the reverse transcriptase template may comprise nucleotide analogs such as 2'-MOE nucleotide(s) or other analogs known to stop/block the reverse transcription.

4. Reverse Transcriptase (RT)

The reverse transcriptase for the present invention can be any protein with reverse transcriptase activities (RNA-dependent DNA polymerization activities). Thus, any reverse transcriptase, or fragments and variants thereof as long as the fragments and variants have reverse transcriptase activities, can be employed. A "reverse transcriptase" of the present invention, therefore, includes reverse transcriptases from retroviruses, other viruses, as well as a DNA polymerase exhibiting reverse transcriptase activity, such as Tth DNA polymerase, Taq DNA polymerase, Tne DNA polymerase, Tma DNA polymerase, etc. RT from retroviruses include, but are not limited to, Moloney Murine Leukemia Virus (MMLV) RT, Human Immunodeficiency Virus (HIV) RT, Avian Sarcoma-Leukosis Virus (ASLV) RT, Rous Sarcoma Virus (RSV) RT, Avian Myeloblastosis Virus (AMV) RT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2Helper Virus UR2AV RT, Avian Sarcoma Virus Y73 Helper Virus YAV RT, Rous Associated Virus (RAV) RT, and Myeloblastosis Associated Virus (MAV) RT.

Avian myoblastosis virus (AMV) reverse transcriptase was the first widely used RNA-dependent DNA polymerase (Verma, Biochim. Biophys. Acta 473: 1 (1977)). The enzyme has 5'-3'RNA-directed DNA polymerase activity, 5-3'DNA-directed DNA polymerase activity, and RNase H activity. RNase H is a processive 5' and 3' ribonuclease specific for the RNA strand for RNA-DNA hybrids (Perbal, A Practical Guide to Molecular Cloning, N.Y.: Wiley & Sons (1984)). Errors in transcription cannot be corrected by reverse transcriptase because known viral reverse transcriptases lack the 3'-5' exonuclease activity necessary for proof-reading (Saunders and Saunders, Microbial Genetics Applied to Biotechnology, London: Croom Helm (1987)). A detailed study of the activity of AMV reverse transcriptase and its associated RNase H activity has been presented by Berger et al, Biochemistry 22:2365-2372 (1983). Another reverse transcriptase which is used extensively in molecular biology is reverse transcriptase originating from Moloney murine leukemia virus (MMLV). See, e.g., Gerard, G. R., DNA 5:271-279 (1986) and Kotewicz, M. L, et al, Gene 35:249-258 (1985). MMLV reverse transcriptase substantially lacking in RNase H activity has also been described. See, e.g., U.S. Pat. No. 5,244,797. Any such reverse transcriptases, or variants or mutants thereof, can be used in the present invention.

In some embodiments, reverse transcriptases that are error-prone are used, usually for random mutagenesis. These enzymes may be referred to as error-prone reverse transcriptases or reverse transcriptases which do not support high fidelity incorporation of nucleotides during polymerization. During primer extension based on the RT template in the pegRNA, an error-prone reverse transcriptase can introduce one or more nucleotides which are mismatched with the RT template sequence, thereby introducing changes to the nucleotide sequence through erroneous polymerization. These errors introduced during synthesis then become integrated into the double strand molecule through hybridization to the corresponding endogenous target strand, removal of the endogenous displaced strand, ligation, and then through one more rounds of endogenous DNA repair and/or replication. In other embodiments of the present invention, reverse transcriptases that are not error-prone, which have higher fidelity, are used. With such less error-prone enzyme, edits in the RT template are introduced into the target with higher fidelity.

Although reverse transcriptases are discussed throughout this disclosure, it is possible to use other polymerases for prime editing. For example, a DNA-dependent DNA polymerase may be used in lieu of a reverse transcriptase (e.g., a prokaryotic polymerase, including Pol I, Pol II, or Pol III, or a eukaryotic polymerase, including Pol a, Pol b, Pol g, Pol d, Pol e, or Pol z). When a DNA-dependent DNA polymerase is employed, the primer extension template component (in this case it should be referred to as a polymerase template rather than a reverse transcriptase template) of the pegRNA will preferably be DNA or partially DNA. Other aspects of the present invention, including the position and types of modified nucleotides, configuration of pegRNAs, and the manner of practicing prime editing, remain substantially the same. It would be apparent to people of skills in the art how to prepare chemically modified pegRNAs according to the present invention for prime editing, and practice prime editing, using DNA-dependent DNA polymerase rather than reverse transcriptase.

5. Target DNA

In the CRISPR/Cas system, the target DNA sequence can be immediately followed by a protospacer adjacent motif (PAM) sequence. The target DNA site may lie immediately 5' of a PAM sequence, which is specific to the bacterial species of the Cas proteinCas9 used. For instance, the PAM sequence of *Streptococcus pyogenes*-derived Cas9 is NGG; the PAM sequence of *Neisseria meningitidis*-derived Cas9 is NNNNGATT; the PAM sequence of *Streptococcus thermophilus*-derived Cas9 is NNAGAA; and the PAM sequence of *Treponema denticola*-derived Cas9 is NAAAAC. In some embodiments, the PAM sequence can be 5'-NGG, wherein N is any nucleotide; 5'-NRG, wherein N is any nucleotide and R is a purine; or 5'-NNGRR, wherein N is any nucleotide and R is a purine. For the *S. pyogenes* system, the selected target DNA sequence should immediately precede (e.g., be located 5') a 5'NGG PAM, wherein N is any nucleotide, such that the guide sequence of the DNA-targeting RNA (e.g., modified gRNA) base pairs with the opposite strand to mediate cleavage at about 3 base pairs upstream of the PAM sequence.

In some embodiments, the degree of complementarity between a guide sequence of the DNA-targeting RNA (e.g., modified pegRNA) and its corresponding target DNA sequence, when optimally aligned using a suitable alignment algorithm, is about or more than about 50%, 55%, 60%, 65%, 70%, 75%, 80%, 85%, 90%, 91%, 92%, 93%, 94%, 95%, 96%, 97%, 98%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, Selangor, Malaysia), and ELAND (Illumina, San Diego, Calif.).

The target DNA site can be selected in a predefined genomic sequence (gene) using web-based software such as ZiFiT Targeter software (Sander et al., 2007, Nucleic Acids Res, 35:599-605; Sander et al., 2010, Nucleic Acids Res, 38:462-468), E-CRISP (Heigwer et al., 2014, Nat Methods, 11:122-123), RGEN Tools (Bae et al., 2014, Bioinformatics, 30(10):1473-1475), CasFinder (Aach et al., 2014, bioRxiv), DNA2.0 gNRA Design Tool (DNA2.0, Menlo Park, Calif.), and the CRISPick Design Tool (Broad Institute, Cambridge, Mass.). Such tools analyze a genomic sequence (e.g., gene or locus of interest) and identify suitable target site for gene editing. To assess off-target gene modifications for each DNA-targeting RNA (e.g., modified gRNA), computationally predictions of off-target sites are made based on quantitative specificity analysis of base-pairing mismatch identity, position and distribution.

B. Primary Cells

The presently disclosed compositions and methods can be used to edit a target nucleic acid in any primary cell of interest. The primary cell can be a cell isolated from any multicellular organism, e.g., a plant cell (e.g., a rice cell, a wheat cell, a tomato cell, an *Arabidopsis thaliana* cell, a *Zea mays* cell, and the like), a cell from a multicellular protist, a cell from a multicellular fungus, an animal cell such as a cell from an invertebrate animal (e.g., fruit fly, cnidarian, echinoderm, nematode, etc.) or a cell from a vertebrate animal (e.g., fish, amphibian, reptile, bird, mammal, etc.), a cell from a human, a cell from a healthy human, a cell from a human patient, a cell from a cancer patient, etc. In some cases, the primary cell with an edited gene can be transplanted to a subject (e.g., patient). For instance, the primary cell can be derived from the subject (e.g., patient) to be treated.

Any type of primary cell may be of interest, such as a stem cell, e.g., embryonic stem cell, induced pluripotent stem cell, adult stem cell (e.g., mesenchymal stem cell, neural stem cell, hematopoietic stem cell, organ stem cell), a progenitor cell, a somatic cell (e.g., fibroblast, hepatocyte, heart cell, liver cell, pancreatic cell, muscle cell, skin cell, blood cell, neural cell, immune cell), and any other cell of the body, e.g., human body. Primary cells are typically derived from a subject, e.g., an animal subject or a human subject, and allowed to grow in vitro for a limited number of passages. In some embodiments, the cells are disease cells or derived from a subject with a disease. For instance, the cells can be cancer or tumor cells.

Primary cells can be harvested from a subject by any standard method. For instance, cells from tissues, such as skin, muscle, bone marrow, spleen, liver, kidney, pancreas, lung, intestine, stomach, etc., can be harvested by a tissue biopsy or a fine needle aspirate. Blood cells and/or immune cells can be isolated from whole blood, plasma or serum. In some cases, suitable primary cells include peripheral blood mononuclear cells (PBMC), peripheral blood lymphocytes (PBL), and other blood cell subsets such as, but not limited to, T cell, a natural killer cell, a monocyte, a natural killer T cell, a monocyte-precursor cell, a hematopoietic stem and progenitor cell (HSPC) such as CD34+ HSPCs, or a non-pluripotent stem cell. In some cases, the cell can be any immune cell including, but not limited to, any T cell such as tumor infiltrating cells (TILs), CD3+ T cells, CD4+ T cells, CD8+ T cells, or any other type of T cell. The T cell can also include memory T cells, memory stem T cells, or effector T cells. The T cells can also be skewed towards particular populations and phenotypes. For example, the T cells can be skewed to phenotypically comprise CD45RO(−), CCR7(+), CD45RA(+), CD62L(+), CD27(+), CD28(+) and/or IL-7Ra (+). Suitable cells can be selected that comprise one of more markers selected from a list comprising CD45RO(−), CCR7 (+), CD45RA(+), CD62L(+), CD27(+), CD28(+) and/or IL-7Ra(+). Induced pluripotent stem cells can be generated from differentiated cells according to standard protocols described in, for example, U.S. Pat. Nos. 7,682,828, 8,058,065, 8,530,238, 8,871,504, 8,900,871 and 8,791,248.

C. Ex Vivo Therapy

The methods described herein can be used in ex vivo therapy. Ex vivo therapy can comprise administering a composition (e.g., a cell) generated or modified outside of an organism to a subject (e.g., patient). In some embodiments, the composition (e.g., a cell) can be generated or modified by the methods disclosed herein. For example, ex vivo therapy can comprise administering a primary cell generated or modified outside of an organism to a subject (e.g., patient), wherein the primary cell has been cultured and edited in vitro in accordance with the methods of the present disclosure that includes contacting the target nucleic acid in the primary cell with one or more modified pegRNAs described herein and a Cas protein (e.g., Cas9 polypeptide) or variant or fragment thereof, an mRNA encoding a Cas protein (e.g., Cas9 polypeptide) or variant or fragment thereof, or a recombinant expression vector comprising a nucleotide sequence encoding a Cas protein (e.g., Cas9 polypeptide) or variant or fragment thereof.

In some embodiments, the composition (e.g., a cell) can be derived from the subject (e.g., patient) to be treated by ex vivo therapy. In some embodiments, ex vivo therapy can include cell-based therapy, such as adoptive immunotherapy.

In some embodiments, the composition used in ex vivo therapy can be a cell. The cell can be a primary cell, including but not limited to, peripheral blood mononuclear cells (PBMCs), peripheral blood lymphocytes (PBLs), and other blood cell subsets. The primary cell can be an immune cell. The primary cell can be a T cell (e.g., CD3+ T cells, CD4+ T cells, and/or CD8+ T cells), a natural killer cell, a monocyte, a natural killer T cell, a monocyte-precursor cell, a hematopoietic stem cell or a non-pluripotent stem cell, a stem cell, or a progenitor cell. The primary cell can be a hematopoietic stem or progenitor cell (HSPC) such as CD34+ HSPCs. The primary cell can be a human cell. The primary cell can be isolated, selected, and/or cultured. The primary cell can be expanded ex vivo. The primary cell can be expanded in vivo. The primary cell can be CD45RO(−), CCR7(+), CD45RA(+), CD62L(+), CD27(+), CD28(+), and/or IL-7Ra(+). The primary cell can be autologous to a subject in need thereof. The primary cell can be non-autologous to a subject in need thereof. The primary cell can be a good manufacturing practices (GMP) compatible reagent. The primary cell can be a part of a combination therapy to treat diseases, including cancer, infections, autoimmune disorders, or graft-versus-host disease (GVHD), in a subject in need thereof.

As a non-limiting example of ex vivo therapy, a primary cell can be isolated from a multicellular organism (e.g., a plant, multicellular protist, multicellular fungus, invertebrate animal, vertebrate animal, etc.) prior to contacting a target nucleic acid within the primary cell with a prime editor and a modified pegRNA. After contacting the target nucleic acid with the prime editor and the modified pegRNA, the edited primary cell or its progeny (e.g., a cell derived from the primary cell) can be returned to the multicellular organism.

D. Methods for Introducing Nucleic Acids and/or Polypeptides into Target Cells Methods for introducing polypeptides and nucleic acids into a target cell (host cell) are known in the art, and any known method can be used to introduce a polypeptide component for prime editing (e.g. a Cas protein, a reverse transcriptase or polymerase, a fusion protein of a Cas protein and a reverse transcriptase, etc.), a nucleic acid component for prime editing (e.g., a pegRNA or a polynucleotide encoding the polypeptide components described above), or an RNP component for prime editing (e.g. of a Cas protein and a pegRNA) into a cell, e.g., a primary cell such as a stem cell, a progenitor cell, or a differentiated cell. Non-limiting examples of suitable methods include electroporation, viral or bacteriophage infection, transfection, conjugation, protoplast fusion, lipofection, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated delivery, e.g. lipid nanoparticle-mediated delivery, polymer nanoparticle-mediated delivery, hybrid lipid-polymer nanoparticle mediated delivery, and the like.

In some embodiments, the components of the CRISPR system can be introduced into a cell using a delivery system. In certain instances, the delivery system comprises a nanoparticle, a microparticle (e.g., a polymer micropolymer), a liposome, a micelle, a virosome, a viral particle, a virus-like particle (VLP), a nucleic acid complex, a transfection agent, an electroporation agent (e.g., using a NEON transfection system), a nucleofection agent, a lipofection agent, and/or a buffer system that includes the polypeptide, nucleic acid, and/or RNP components for prime editing. For instance, the components can be mixed with a lipofection agent such that they are encapsulated or packaged into cationic submicron oil-in-water emulsions. Alternatively, the components can be delivered without a delivery system, e.g., as an aqueous solution.

Methods of preparing liposomes and encapsulating polypeptides and nucleic acids in liposomes are described in, e.g., Methods and Protocols, Volume 1: Pharmaceutical Nanocarriers: Methods and Protocols. (ed. Weissig). Humana Press, 2009 and Heyes et al. (2005) *J Controlled Release* 107:276-87. Methods of preparing microparticles and encapsulating polypeptides and nucleic acids are described in, e.g., Functional Polymer Colloids and Microparticles volume 4 (Microspheres, microcapsules & liposomes). (eds. Arshady & Guyot). Citus Books, 2002 and *Microparticulate Systems for the Delivery of Proteins and Vaccines*. (eds. Cohen & Bernstein). CRC Press, 1996. See *Advanced Drug Delivery Reviews* 2021, Volume 168, for reviews on preparation of nanoparticles such as lipid, polymer or hybrid lipid-polymer nanoparticles.

E. Methods for Assessing the Efficiency of Genome Editing

To functionally test the presence of the correct genomic editing modification, the target DNA can be analyzed by standard methods known to those in the art. For example, indel mutations can be identified by sequencing using the SURVEYOR® mutation detection kit (Integrated DNA Technologies, Coralville, Iowa) or the Guide-it™ Indel Identification Kit (Clontech, Mountain View, Calif.). Homology-directed repair (HDR) or prime editing-mediated edits can be detected by PCR-based methods, and in combination with sequencing or RFLP analysis. Non-limiting examples of PCR-based kits include the Guide-it Mutation Detection Kit (Clontech) and the GeneArt® Genomic Cleavage Detection Kit (Life Technologies, Carlsbad, Calif.). Deep sequencing can also be used, particularly for a large number of samples or potential target/off-target sites.

In certain embodiments, the efficiency (e.g., specificity) of genome editing corresponds to the number or percentage of on-target genome editing events relative to the number or percentage of all genome editing events, including on-target and off-target events.

In some embodiments, the modified pegRNAs described herein are capable of enhancing genome editing of a target DNA sequence in a cell such as a primary cell relative to the corresponding unmodified pegRNAs. The genome editing can comprise one or more nucleotide substitutions, insertions and/or deletions.

In certain embodiments, the nuclease-mediated genome editing efficiency of a target DNA sequence in a cell is enhanced by at least about 0.5-fold, 0.6-fold, 0.7-fold, 0.8-fold, 0.9-fold, 1-fold, 1.1-fold, 1.2-fold, 1.3-fold, 1.4- fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 15-fold, 20-fold, 25-fold, 30-fold, 35-fold, 40-fold, 45-fold, 50-fold, or greater in the presence of a modified pegRNA described herein compared to the corresponding unmodified pegRNA sequence.

F. Methods for Preventing or Treating a Genetic Disease in a Subject

The modified pegRNAs can be applied to targeted genome-editing therapeutics of genetic diseases. Current approaches for precisely correcting genetic mutations in the genome of primary patient cells have been very inefficient (sometimes less than 1% of cells can be precisely edited). The modified pegRNAs described herein can enhance the activity of genome editing and increase the efficacy of genome editing-based therapies. In particular embodiments, modified pegRNAs may be used for in vivo gene editing of genes in subjects with a genetic disease. The modified pegRNAs can be administered to a subject via any suitable route of administration and at doses or amounts sufficient to enhance the effect (e.g., improve the genome editing efficiency) of the genome-editing therapy.

Provided herein is a method for preventing or treating a genetic disease in a subject in need thereof by correcting a genetic mutation associated with the disease. The method comprises administering to the subject a modified pegRNA described herein in an amount that is sufficient to correct the mutation, and a prime editor. Also provided herein is the use of a modified pegRNA described herein in the manufacture of a medicament for preventing or treating a genetic disease in a subject in need thereof by correcting a genetic mutation associated with the disease. The modified pegRNA can be contained in a composition that also includes a Cas protein for prime editing (e.g., Cas9 nickase), an mRNA encoding a Cas protein (e.g., Cas9 nickase), or a recombinant expression vector comprising a nucleotide sequence encoding a Cas protein (e.g., Cas9 nickase). Similarly, the modified pegRNA can be contained in a composition with other components for prime editing, such as a nicking gRNA, a reverse transcriptase or a fusion protein of a Cas protein and a reverse transcriptase. The polypeptide and nucleic acid components for prime editing are described above, and any combination with a modified pegRNA is contemplated herein. In some instances, the modified pegRNA is included in a delivery system described above.

The genetic diseases that may be corrected by the method include, but are not limited to, X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disease or disorders, inflammation, immune-related diseases or disorders, metabolic diseases, liver diseases and disorders, kidney diseases and disorders, muscular/skeletal diseases and disorders (e.g., muscular dystrophy, Duchenne muscular dystrophy), neurological and neuronal diseases and disorders, cardiovascular diseases and disorders, pulmonary diseases and disorders, ocular diseases and disorders, viral infections (e.g., HIV infection), and the like.

EXAMPLES

Aspects of the present teachings can be further understood in light of the following examples, which should not be construed as limiting the scope of the present teachings in any way.

Figure 4:
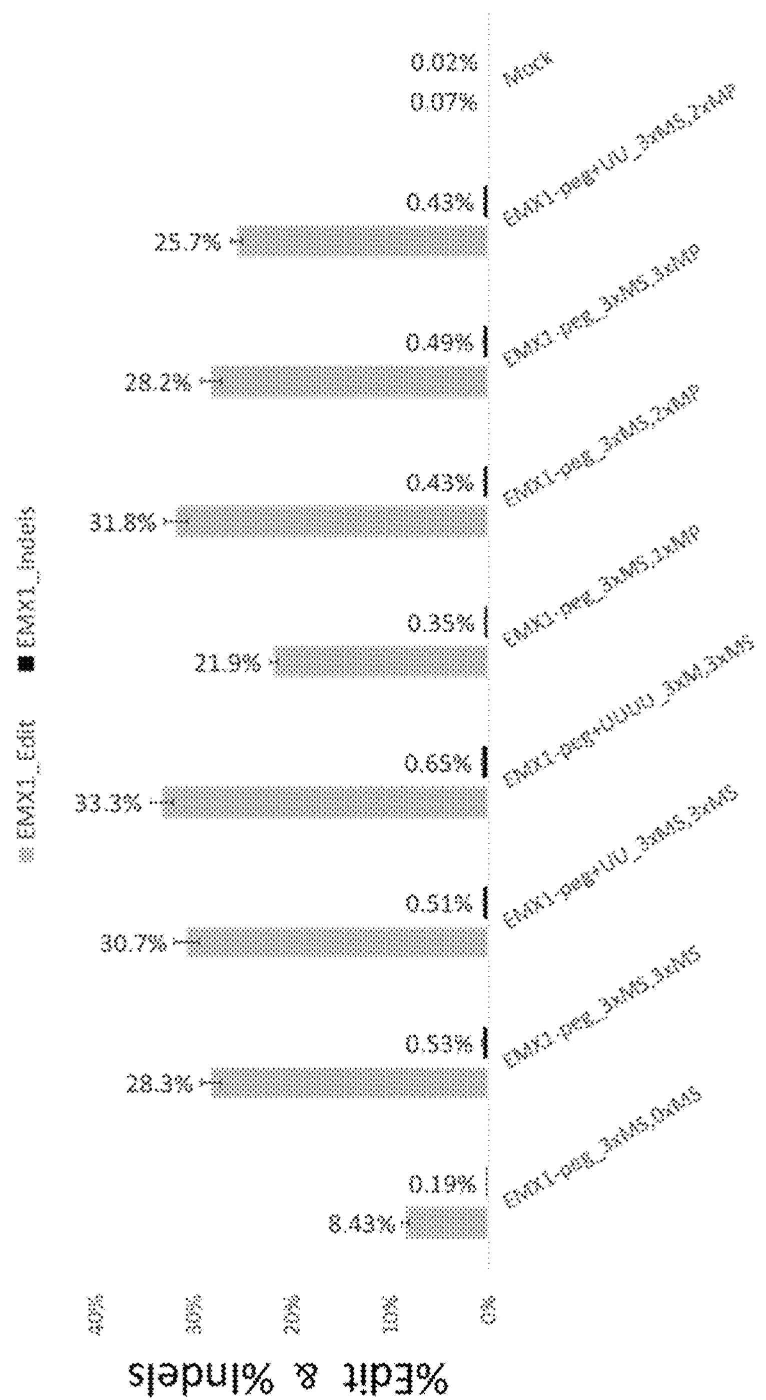
FIG. 4 is a graph showing the effectiveness of prime editing of EMX1 in K562 cells using a second set of chemically-modified pegRNAs.
Figure 5:
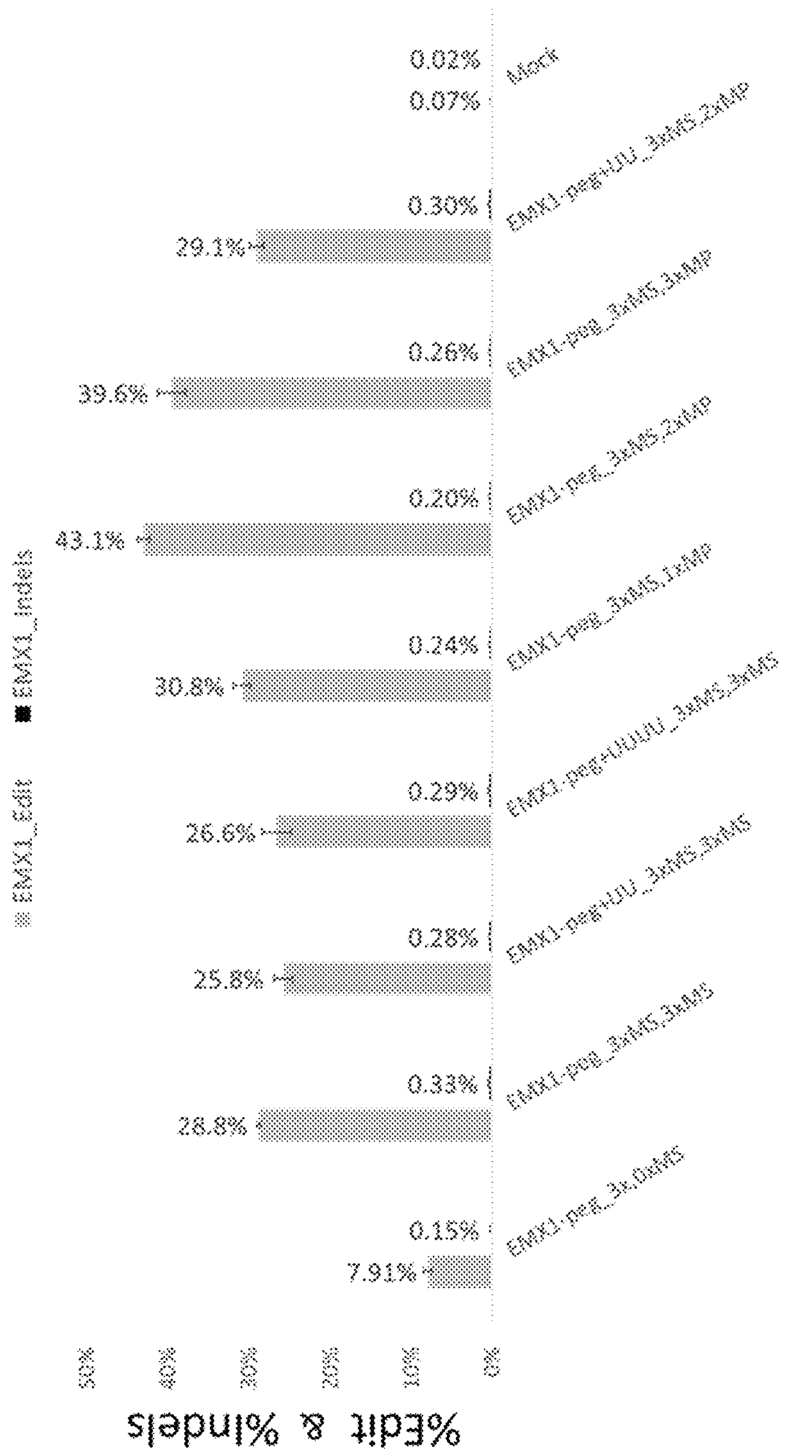
FIG. 5 is a graph showing the effectiveness of prime editing of EMX1 in Jurkat cells using a second set of chemically-modified pegRNAs.
Figure 6:
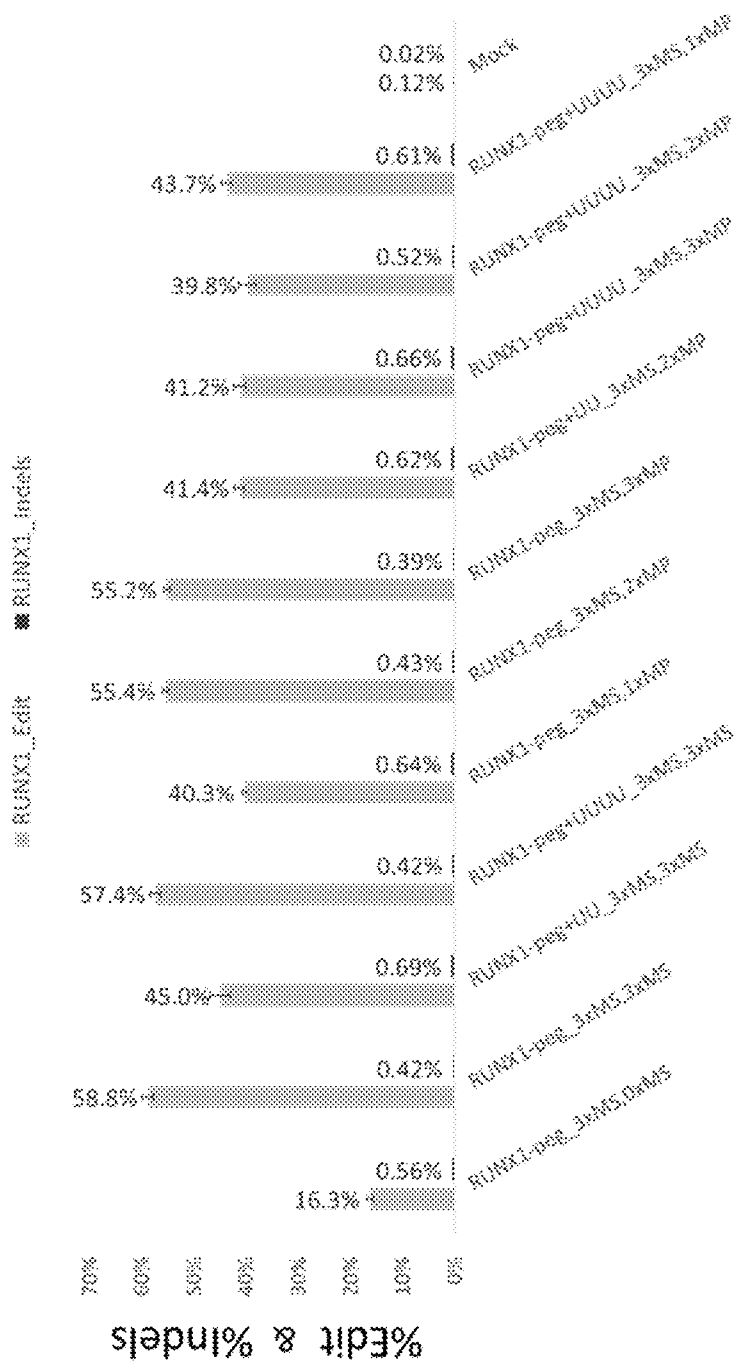
FIG. 6 is a graph showing the effectiveness of prime editing of RUNX1 in K562 cells using an initial set of chemically-modified pegRNAs.
Figure 7:
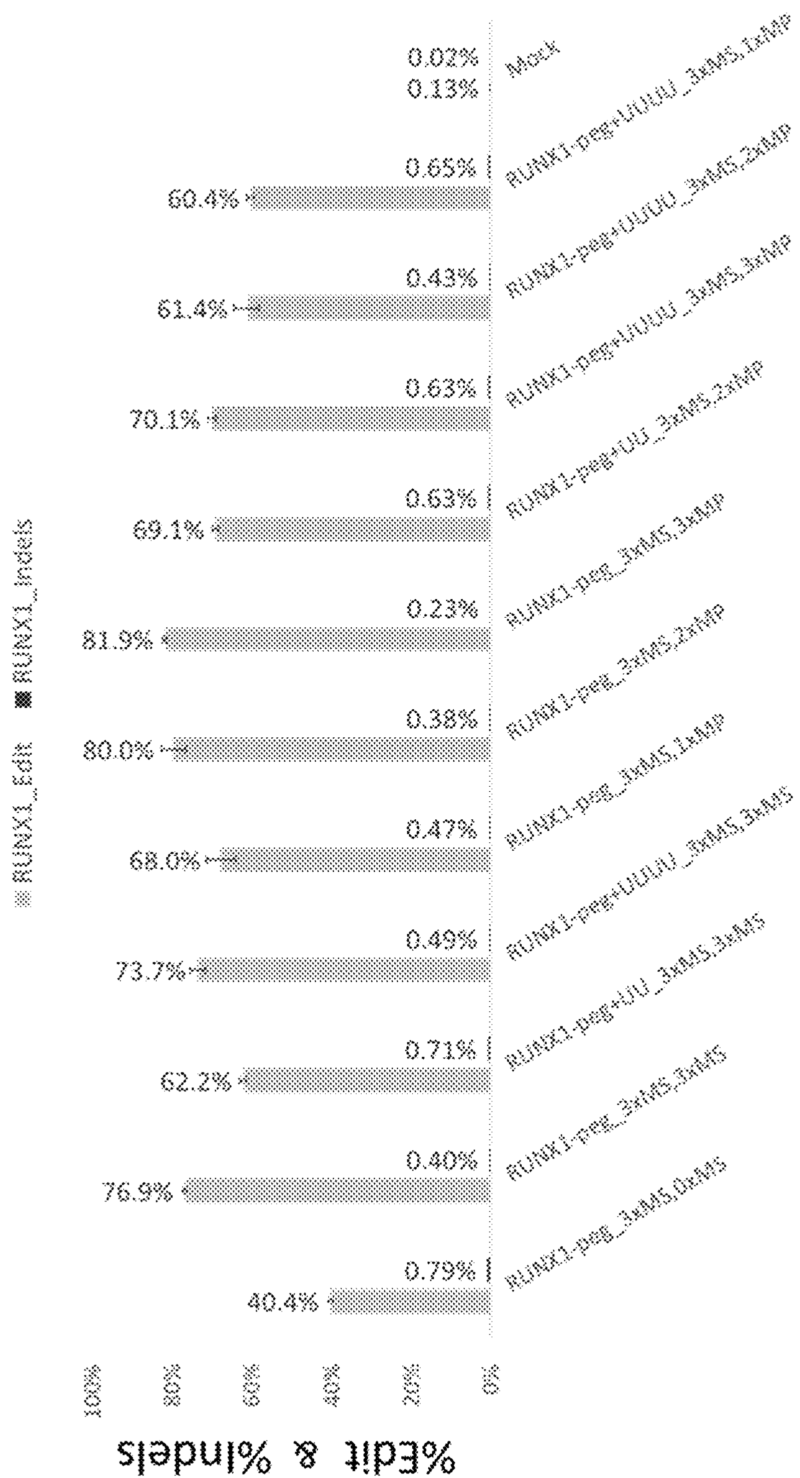
FIG. 7 is a graph showing the effectiveness of prime editing of RUNX1 in Jurkat cells using an initial set of chemically-modified pegRNAs.
Figure 8:
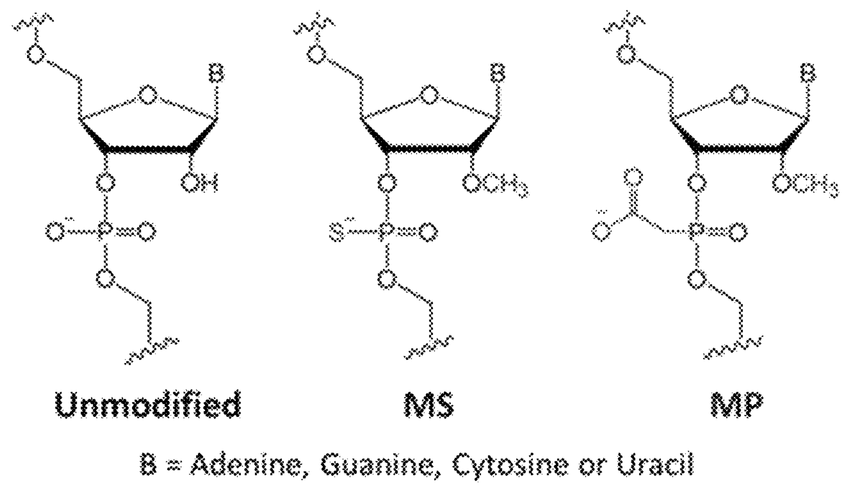
FIG. 8 illustrates the chemical structure of 2'-O-methyl-3'-phosphorothioate (MS) and 2'-O-methyl-3'-phosphonoacetate (MP), two examples of chemically-modified nucleotides that may be incorporated into the pegRNAs disclosed herein.
Figure 9:
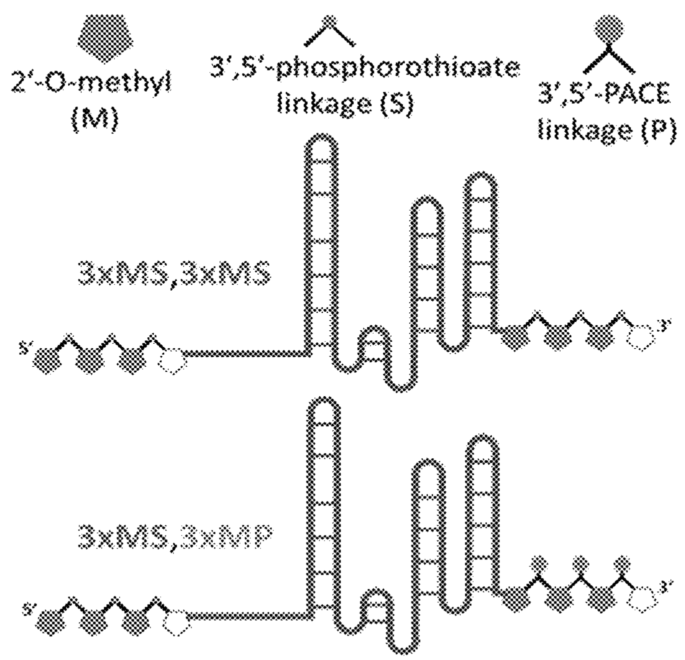
FIG. 9 illustrates two exemplary gRNAs that incorporate 3×MS at the 5' and 3' end (top), or 3×MS at the 5' end and 3×MP at the 3' end (bottom).

Example 1: Evaluation of the Use of 2'-O-methyl-3'-phosphonoacetate (MP) and 2'-O-methyl-3'-phosphorothioate (MS) Modifications at the 3' End of Chemically Synthesized pegRNAs Methods An experiment was designed to test the effectiveness of chemically-modified pegRNAs using EMX1 as the target gene. An mRNA encoding a prime editor (in this case, a fusion protein comprising a Cas9 nickase and an MMLV-derived reverse transcriptase) was introduced into K562 or Jurkat cells with a guide RNA targeting the EMX1 gene. Each transfection was performed in triplicate samples of cells that were cultured separately. Genomic DNA was harvested, the EMX1 target sequence was amplified using primers specific for EMX1 to produce amplicons that were sequenced, and the extent of prime editing ("% Edit") was determined from the sequencing results. Also determined from the sequencing results was the extent of undesired indel formation ("% Indels") at the nickase site in the EMX1 target sequence. Such indels are known byproducts of prime editing and are generally considered undesirable (see Anzalone et al. 2019). Prime editing yields and indel byproduct yields per pegRNA are plotted as bar graphs in FIGS. 2-7. The sequences used in these assays were selected from sequences shown in Table 1. Data in FIGS. 2-3 were obtained using a first batch synthesis of pegRNAs targeting EMX1, whereas data in FIGS. 4-5 were obtained using a second batch synthesis of pegRNAs targeting EMX1. Note that some of the same sequences were synthesized again in the second batch synthesis. Conversely data in FIGS. 6-7 were obtained using pegRNAs targeting RUNX1 (i.e., using sequences described in Table 2).

Results

As illustrated by the results shown in FIGS. 2-7, the inclusion of MS and/or MP nucleotides as chemical modifications at the 3' and/or 5' end of pegRNAs increases prime editing activity. The enhanced activity of constructs having modified nucleotides at the 3' end of the pegRNA is particularly surprising, given the fact that the prime editing end (here the 3' end) of a pegRNA contains additional functional sites (e.g., the primer binding site and a reverse transcriptase template sequence). As noted above, prior to the present disclosure it would have been expected that the inclusion of chemically-modified nucleotides (e.g., MS and/or MP) at this site could interfere with the functionality provided by these additional components of a pegRNA.

Example 2: Effects on gRNA Stability by MP and MS Modifications at the 3' End of Chemically Synthesized gRNAs The level of gRNAs containing different numbers of consecutive 2'-O-methyl-3'-phosphonoacetate (2'-O-methyl-3'-PACE, or "MP") modifications at the 3' end was evaluated in comparison to guide RNAs with 2'-O-methyl-3'-phosphorothioate (or "MS") modifications after various time periods after transfection into cells. The results of this study are further described in Ryan et al. "Phosphonoacetate Modifications Enhance the Stability and Editing Yields of Guide RNAs for Cas9 Editors." *Biochemistry* (2022) doi.org/10.1021/acs.biochem.1c00768.

Methods

Preparation of gRNAs and mRNAs. RNA oligomers were synthesized on Dr. Oligo 48 and 96 synthesizers (Biolytic Lab Performance Inc.) using 2'-O-thionocarbamate-protected nucleoside phosphoramidites (Sigma-Aldrich and Hongene) on controlled pore glass (LGC) according to previously described procedures. The 2'-O-methyl-3'-O-(diisopropylamino)-phosphinoacetic acid-1,1-dimethylcyanoethyl ester-5'-O-dimethoxytrityl nucleosides used for synthesis of MP-modified RNAs were purchased from Glen Research and Hongene. For phosphorothioate containing oligomers, the iodine oxidation step after the coupling reaction was replaced by a sulfurization step using a 0.05 M solution of 3-((N,N-dimethylaminomethylidene)amino)-3H-1,2,4-dithiazole-5-thione in a pyridine-acetonitrile (3:2) mixture for 6 min. Unless otherwise noted, reagents for solid-phase RNA synthesis were purchased from Glen Research and Honeywell. The phosphonoacetate modifications incorporated in the MP-modified gRNAs were synthesized using protocols adapted from previous publications by using the commercially available protected nucleoside phosphinoamidite monomers above. See Dellinger et al. "Solid-phase chemical synthesis of phosphonoacetate and thiophosphonoacetate oligodeoxynucleotides," *Journal of the American Chemical Society* 125.4 (2003): 940-950; Threlfall et al. "Synthesis and biological activity of phosphonoacetate- and thiophosphonoacetate-modified 2'-O-methyl oligoribonucleotides." *Organic & Biomolecular Chemistry* 10.4 (2012): 746-754. All oligonucleotides were purified using reversed-phase high-performance liquid chromatography (RP-HPLC) and analyzed by liquid chromatography—mass spectrometry (LC-MS) using an Agilent 1290 Infinity series LC system coupled to an Agilent 6545 Q-TOF (time-of-flight) mass spectrometer. In all cases, the mass determined by deconvolution of the series of peaks comprising multiple charge states in a mass spectrum of purified gRNA matched the expected mass within error of the calibrated instrument (the specification for quality assurance used in this assay is that the observed mass of purified gRNA is within 0.01% of the calculated mass), thus confirming the composition of each synthetic gRNA.

PE2 mRNA, which encodes the PE2 protein, was purchased from TriLink as a custom order by providing the coding sequences to which TriLink added their own proprietary 5' and 3' UTRs. The custom mRNA was fully substituted with 5-methylcytidine and pseudouridine, capped with CleanCap AG, and polyA tailed.

Cell culture and nucleofections. Human K562 cells were obtained from ATCC and cultured in RPMI 1640+ GlutaMax media (gibco) supplemented with 10% fetal bovine serum (gibco). K562 cells (within passage number 4 to 14) were nucleofected using a Lonza 4D-Nucleofector (96-well shuttle device, program FF-120) per manufacturer's instructions utilizing a Lonza SF Cell Line kit (V4SC-2960) with 0.2 million cells per transfection in 20 μL of SF buffer combined with 8 μL of 125 pmoles of pegRNA with 100 pmoles of nicking gRNA and 1.35 pmoles of PE2 mRNA in PBS buffer for prime editing. Cells were cultured at 37° C. in ambient oxygen and 5% carbon dioxide and were harvested at 48 hr post-transfection.

Human Jurkat Clone E6-1 cells were obtained from ATCC and were cultured in RPMI 1640+ GlutaMax media supplemented with 10% fetal bovine serum. Jurkat cells (within passage number 7 to 20) were nucleofected (program CL-120) utilizing a Lonza SE Cell Line kit (V4SC-1960) with 0.2 million cells in 20 μL of SE buffer combined with 8 μL of 125 pmoles of pegRNA, 100 pmoles of nicking gRNA and 1.35 pmoles of PE2 mRNA in PBS buffer. Cultured cells were harvested at 72 hr post-transfection.

qRT-PCR assays. Human K562 cells were cultured as above, and 0.2 million cells per replicate were nucleofected with 125 pmoles of gRNA (without Cas9 mRNA or protein) as described. For each timepoint, cells were collected in 1.7-mL Eppendorf tubes, rinsed with PBS, then resuspended in 750 μL of Qiazol and kept at room temperature for 5 min before transferring to a −20° C. freezer. Total RNA in PBS was isolated from Qiazol plus chloroform extracts using a miRNeasy kit (Qiagen) on a QiaCube HT and then immediately reverse transcribed using a Protoscript II first-strand cDNA synthesis kit (NEB). qRT-PCR was performed on an Applied Biosystems QuantStudio 6 Flex instrument using TaqPath ProAmp master mix with two TaqMan MGB probes, one for gRNA labeled with FAM and the other for U6 snRNA labeled with VIC (Thermo Fisher) for normalization to the amount of total RNA isolated, calculated as ΔCt. The ΔCt values for triplicate samples were averaged and normalized to the lowest observed mean ΔCt value to calculate ΔΔCt values. Relative gRNA levels were calculated as $2^{-\Delta\Delta Ct}$.

Results

Figure 10:
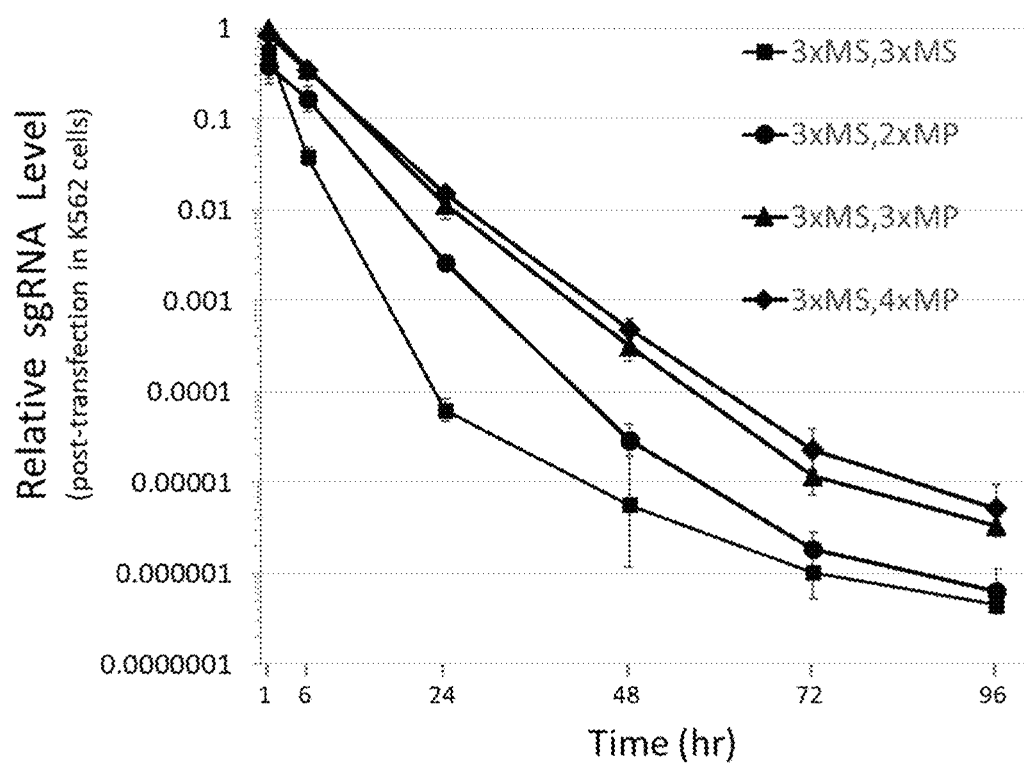
FIG. 10 is a graph showing the results of an experiment that evaluated the relative level of chemically-modified gRNA in K562 cells over time.
Figure 12:
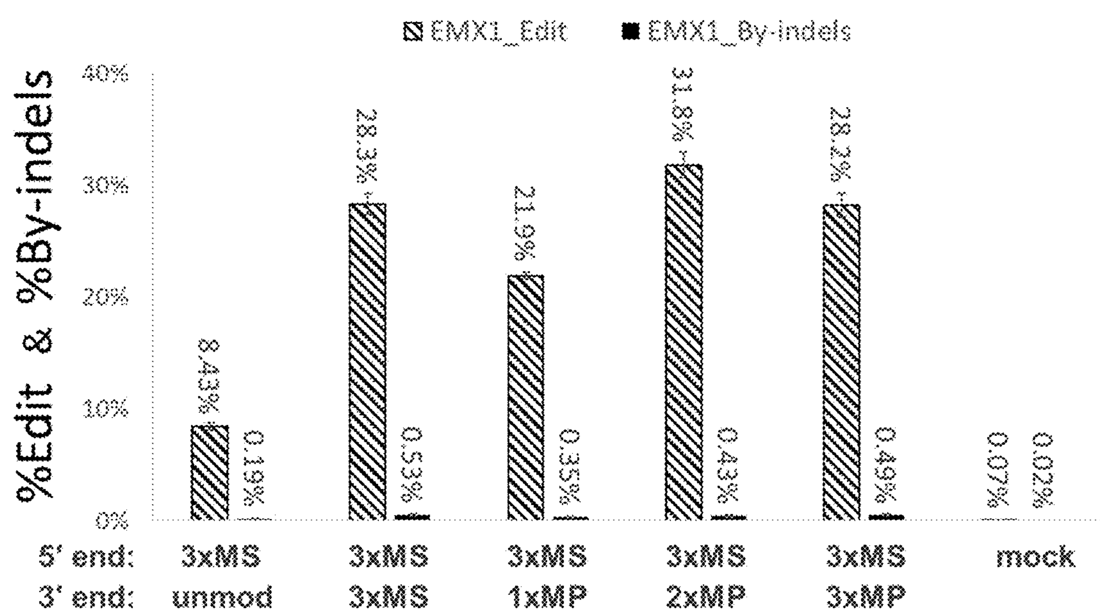
FIG. 12 is a graph showing the results of an experiment that assessed prime editing of EMX1 in K562 cells. In this case, the prime editing was used to knockout the PAM in EMX1.
Figure 13:
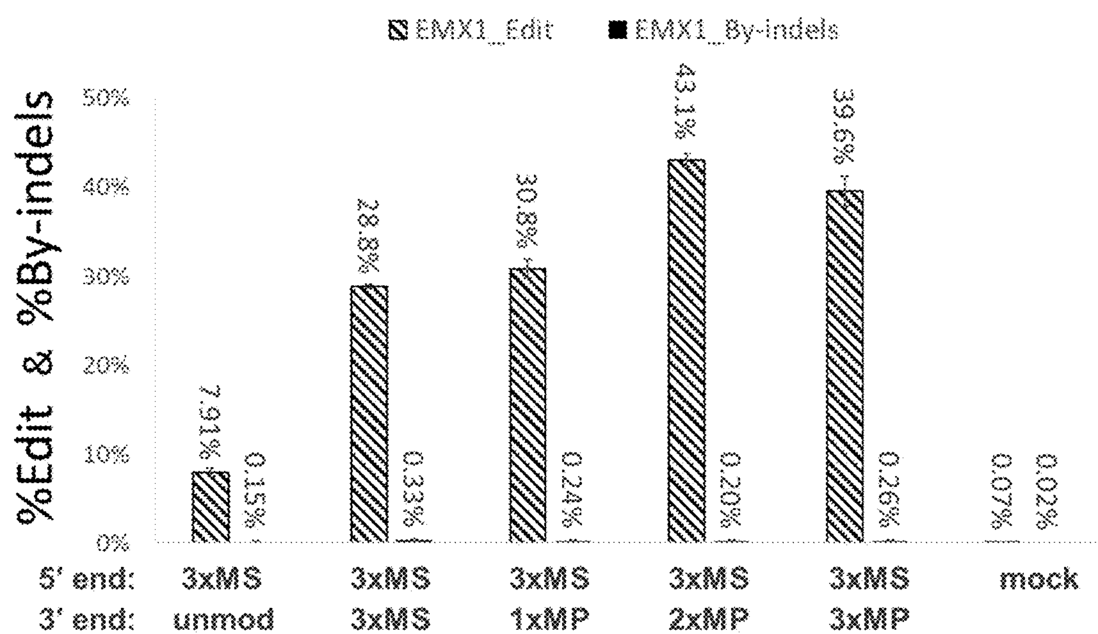
FIG. 13 is a graph showing the results of an experiment that assessed prime editing of EMX1 in Jurkat cells. In this case, the prime editing was used to knockout the PAM in EMX1.
Figure 14:
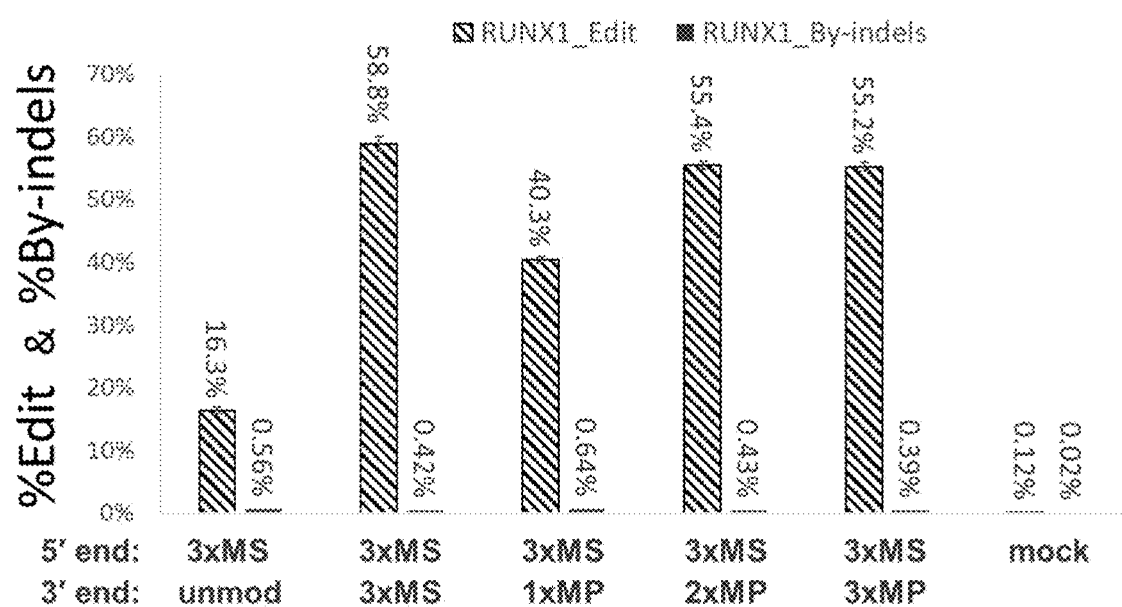
FIG. 14 is a graph showing the results of an experiment that assessed prime editing of RUNX1 in K562 cells. In this case, the prime editing was used to introduce a three-base insertion in RUNX1.
Figure 15:
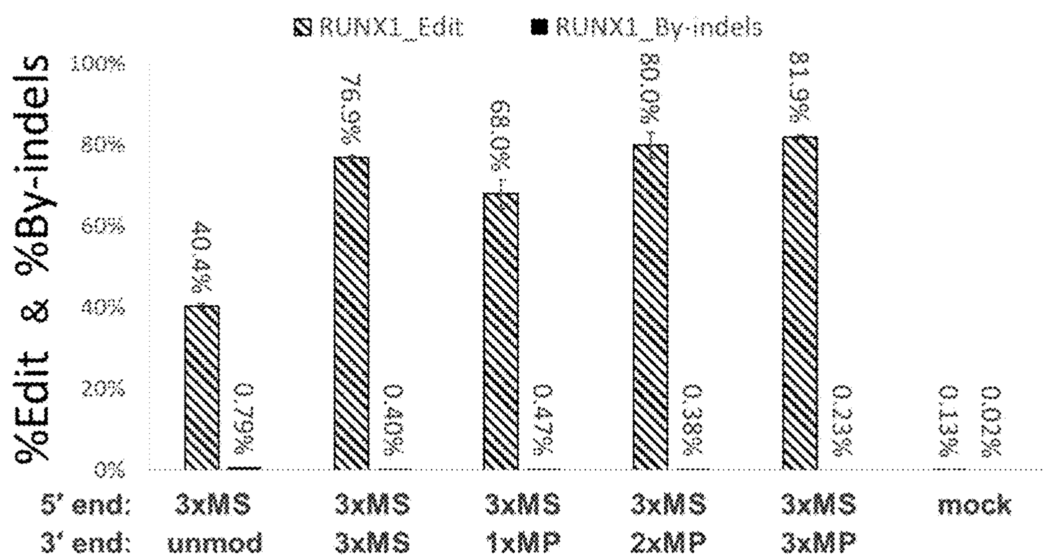
FIG. 15 is a graph showing the results of an experiment that assessed prime editing of RUNX1 in Jurkat cells. In this case, the prime editing was used to introduce a three-base insertion in RUNX1.

As shown by FIG. 10, a much steeper decline in the relative level of the 3×MS,3×MS gRNA detected across 1, 6, and 24 h post-transfection was observed, in comparison to that for any of the gRNAs modified with MPs at the 3' end (either two, three, or four consecutive MPs). Specifically, at 1 h post-transfection, the relative amounts of transfected gRNA differed by only 2.6-fold with largely overlapping error bars among all four variations of 3' end protection, whereas much larger differences were observed at 6 h post-transfection, when the remaining amount of 3×MS,3×MS-protected gRNA had dropped to a relative level of about 1/10 (0.039) that of the 3×MS,3×MP- and 3×MS,4×MP-protected gRNAs (0.341-0.351). The differences became even larger at the 24 h time point where they varied according to the level of 3' end protection in a logical progression from having 3×MS to 2×MP to 3×MP to 4×MP at the 3' end, resulting in residual gRNA levels that spanned ca. 250-fold, consistent with the level of 3' end protection. Thus, it was found that incorporating MP modifications at the 3' end of uncomplexed gRNAs can significantly enhance their stability in transfected cells relative to MS modifications, specifically by 1-2 orders of magnitude for three different MP-modified gRNAs tested in parallel with an MS-only modified gRNA. The designs with three or four consecutive MPs at the 3' end can prolong the lifetimes of the free gRNAs across even longer time points (72 and 96 h post-transfection).

Example 3: Evaluation of the Incorporation of MP or MS Modifications at the 3' End of Chemically Synthesized PegRNAs An experiment was conducted to explore two approaches for prime editing adopted from the literature that knock out the PAM in EMX1 or introduce a 3-base insertion in RUNX1, both of which utilize pegRNAs with a primer binding sequence comprising 15 nucleotides. The particular sequence edits that were evaluated in this experiment are shown in FIG. 11.

Methods

The methods are generally the same as described in Example 2. In short, prime editing approaches were adopted to knockout the PAM in EMX10r to introduce a 3-base insertion in RUNX1. K562 cells were co-transfected with prime editor mRNA (in this case, a fusion protein comprising a Cas9 nickase and an MMLV-derived reverse transcriptase) and synthetic pegRNA modified by 3×MS at the 5' end and various modification schemes at the 3' end (as indicated) for editing EMX1 or RUNX1. Jurkat cells were likewise transfected using the same pegRNAs for editing EMX1 or RUNX1. Editing yields were measured by deep sequencing of PCR amplicons of the target loci for both the desired edit (% Edit) and any contaminating indel byproducts (% By-indels). Bars in the associated figures represent means with std. dev. (n=3).

PCR-targeted deep sequencing and quantification of targeted genomic modifications. Genomic DNA purification and construction of PCR-targeted deep sequencing libraries were performed as previously described. Library concentration was determined using a Qubit dsDNA BR assay kit (Thermo Fisher). Paired-end 2×220-bp reads were sequenced on a MiSeq (Illumina) at 0.8 ng/μL of PCR-amplified library along with 20.5% PhiX.

Paired-end reads were merged using FLASH version 1.2.11 software and then mapped to the human genome using BWA-MEM software (bwa-0.7.10) set to default parameters. Reads were scored as having an indel or not according to whether an insertion or a deletion was found within 10 bp's of the Cas9 cleavage site. For prime editing analysis, reads were scored as having an edit if the desired edit was identified in the read. For cytidine base editing analysis, reads were scored as base edited if cytidines were edited within a window of 10-20 bp upstream of the PAM site. For each replicate in each experiment, mapped reads were segregated according to mapped amplicon locus and were binned by the presence or absence of an indel or edit. The tally of reads per bin was used to calculate % indels or % edits produced at each locus. Indel or edit yields and standard deviations for plots were calculated by logit transformation of % indels or % edits, transformed as $\ln(r/(1-r))$ where r is % indels or % edits per specific locus, to closely approximate a normal distribution. Triplicate mock transfections provided a mean mock control (or negative control), and triplicate samples showing a mean indel yield or mean edit yield significantly higher (t-test $p<0.05$) than the corresponding negative control were considered above background.

Results

As shown by FIGS. 12-15, this experiment compared pegRNAs having 3×MS at the 3' end for both targets with alternative designs having one, two or three consecutive MPs at the 3' end, each co-transfected with PE2 mRNA in K562 or Jurkat cells. The results show that pegRNAs with MP modifications at the 3' end performed well and can achieve comparable, or in some cases somewhat higher, editing yields than 3×MS. For the two pegRNA sequences tested here, designs with 2×MP and/or 3×MP at the 3' end performed consistently better than designs with 1×MP at the 3' end (specifically 1.2-1.4-fold better).

Exemplary Embodiments

Product Embodiments (P Embodiments)

P1. A prime-editing guide RNA (pegRNA), comprising:
- a guide sequence that is complementary to a target sequence in a target region of a nucleic acid;
- a sequence capable of interacting with a CRISPR-associated (Cas) protein;
- a reverse transcriptase template comprising one or more edits to a sequence of the nucleic acid;
- a primer-binding site capable of hybridizing to the target region; and
- wherein the pegRNA comprises (a) a 5' end and a 3' end, one of which is a prime editing end and the other is a distal end; and (b) one or more modified nucleotides within 5 nucleotides of the prime editing end, wherein each modified nucleotide is a nucleotide comprising a 2' modification selected from 2'-O-methoxyethyl (2'-MOE), 2'-fluoro, 2'-O-methyl, and 2'-deoxy, and an internucleotide linkage modification selected from 3'-phosphorothioate, 3'-phosphonocarboxylate, and 3'-thiophosphoncarboxylate.

P2. The pegRNA of embodiment P1, wherein the one or more edits to the sequence of the nucleic acid comprise the incorporation of one or more nucleotide changes and/or targeted mutagenesis to the sequence of the nucleic acid.

P3. The pegRNA of embodiment P1 or P2, wherein the one or more edits to the sequence of the nucleic acid comprise one or more single-nucleotide changes, an insertion of one or more nucleotides, and/or a deletion of one or more nucleotides.

P4. The pegRNA of any one of embodiments P1-P3, wherein the pegRNA is a single guide RNA.

P5. The pegRNA of any one of embodiments P1-P4, wherein the 3'-phosphonocarboxylate is 3'-phosphonoacetate.

P6. The pegRNA of any one of embodiments P1-P5, wherein the 3'-thiophosphoncarboxylate is 3'-thiophosphonoacetate.

P7. The pegRNA of any one of embodiments P1-P6, wherein the one or more modified nucleotides within 5 nucleotides of the prime editing end comprise 2'-O-methyl-3'-phosphorothioate ("MS"), 2'-O-methyl-3'-phosphonoacetate ("MP") or 2'-O-methyl-3'-thiophosphonoacetate ("MSP").

P8. The pegRNA of any one of embodiments P1-P7, wherein the 3' end of the pegRNA is part of the primer-binding site sequence.

P9. The pegRNA of any one of embodiments P1-P8, wherein the pegRNA further comprises one or more modified nucleotides within 5 nucleotides of the distal end.

P10. The pegRNA of embodiment P9, wherein the one or more modified nucleotides within 5 nucleotides of the distal end comprise a nucleotide comprising a 2' modification selected from 2'-MOE, 2'-fluoro, 2'-O-methyl and 2'-deoxy, and an internucleotide linkage modification selected from 3'-phosphorothioate, 3'-phosphonocarboxylate, and 3'-thiophosphoncarboxylate.

P11. The pegRNA of embodiment P10, wherein the 3'-phosphonocarboxylate is 3'-phosphonoacetate.

P12. The pegRNA of embodiments P10 or P11, wherein the 3'-thiophosphoncarboxylate is 3'-thiophosphonoacetate.

P13. The pegRNA of any one of embodiments P10-P12, wherein the one or more modified nucleotides within 5 nucleotides of the prime editing end and the distal end both comprise MS, MP and/or MSP.

P14. The pegRNA of any one of embodiments P1-P13, wherein the 3' end of the pegRNA comprises an extension tail.

P15. The pegRNA of embodiment P14, wherein the extension tail comprises at least 1, 2, 3, 4, 5, 6, 7, 8, 9, or 10 uridine bases.

P16. The pegRNA of any one of embodiments P1-P13, which does not comprise an extension tail at the prime editing end.

P17. The pegRNA of any one of embodiments P1-P13, which does not comprise a poly(N) tail at the prime editing end.

P18. The pegRNA of any one of embodiments P1-P13, which does not comprise a polyuridine tail at the prime editing end.

P19. The pegRNA of any one of embodiments P1-P18, wherein the one or more modified nucleotides within 5 nucleotides of the prime editing end comprises MS.

P20. The pegRNA of any one of embodiments P1-P19, wherein the one or more modified nucleotides within 5 nucleotides of the prime editing end comprises a 3'-phosphonocarboxylate internucleotide linkage.

P21. The pegRNA of any one of embodiments P1-P20, wherein the one or more modified nucleotides within 5 nucleotides of the prime editing end comprises MP.

P22. The pegRNA of any one of embodiments P1-P21, wherein the one or more modified nucleotides within 5 nucleotides of the prime editing end comprises a 3'-thiophosphonocarboxylate internucleotide linkage.

P23. The pegRNA of any one of embodiments P1-P22, wherein the one or more modified nucleotides within 5 nucleotides of the prime editing end comprises MSP.

P24. The pegRNA of any one of embodiments P1-P22, comprising two consecutive MS, two consecutive 2'-O-methyl-3'-phosphonocarboxylate modified nucleotides or two consecutive 2'-O-methyl-3'-thiophosphonocarboxylate modified nucleotides within 5 nucleotides of the prime editing end.

P25. The pegRNA of any one of embodiments P1-P23, comprising three consecutive MS, three consecutive 2'-O-methyl-3'-phosphonocarboxylate modified nucleotides or three consecutive 2'-O-methyl-3'-thiophosphonocarboxylate modified nucleotides within 5 nucleotides of the prime editing end.

P26. The pegRNA of embodiment P24 or P25, wherein the 3'-phosphonocarboxylate is 3'-phosphonoacetate, and the 3'-thiophosphonocarboxylate is 3'-thiophosphonoacetate.

P27. The pegRNA of any of the preceding embodiments, wherein the one or more modified nucleotides at the prime editing end comprises a nucleotide that does not comprise MS, MP or MSP, but comprises (1) a 2'-modification selected from 2'-O-methoxyethyl (2'-MOE), 2'-fluoro, 2'-O-methyl and 2'-deoxy, and (2) an internucleotide linkage modification selected from phosphorothioate, phosphonocarboxylate, and thiophosphonocarboxylate.

P28. The pegRNA of any one of the preceding embodiments, wherein the one or more modified nucleotides at the distal end comprises a nucleotide that does not comprise MS, MP or MSP, but comprises (1) a 2'-modification selected from 2'-O-methoxyethyl (2'-MOE), 2'-fluoro, 2'-O-methyl and 2'-deoxy, and (2) an internucleotide linkage modification selected from phosphorothioate, phosphonocarboxylate, and thiophosphonocarboxylate.

P29. The pegRNA of any one of the preceding embodiments, further comprising at least one modified nucleotide that is not within 5 nucleotides of the prime editing end or the distal end.

P30. The pegRNA of any one of the preceding embodiments wherein the primer binding site comprises 2'-deoxy modifications.

P31. The pegRNA of any one of the preceding embodiments wherein every nucleotide in the primer binding site comprises a 2'-deoxy modification.

P32. The pegRNA of any one of the preceding embodiments wherein every nucleotide in the reverse transcriptase template comprises a 2'-deoxy modification.

P33. The pegRNA of any one of the preceding embodiments, wherein the first nucleotide at the 3' end of the pegRNA comprises a 2'-O-methyl modification.

P34. The pegRNA of any one of embodiments P1-P33, which is a Cas9 style guide RNA.

P35. The pegRNA of any one of embodiments P1-P33, which is a Cpf1 style guide RNA.

P36. The pegRNA of any one of embodiments P1-P35, wherein the prime editing end is the 3' end.

P37. The pegRNA of any one of embodiments P1-P35, wherein the prime editing end is the 5' end.

P38. The pegRNA of any one of embodiments P1-P33, wherein the pegRNA comprises, from the 5'end to the 3'end:

the guide sequence, a Cas9 scaffold, the reverse transcriptase template and the primer binding site.

P39. The pegRNA of any one of embodiments P1-P33, wherein the pegRNA comprises, from the 5'end to the 3'end:

the reverse transcriptase template, the primer binding site, the guide sequence and a scaffold.

P40. The pegRNA of any one of embodiments P1-P33, wherein the pegRNA comprises, from the 5'end to the 3'end:

the reverse transcriptase template, the primer binding site, a scaffold and the guide sequence.

P41. The pegRNA of any one of embodiments P1-P33, wherein the pegRNA comprises, from the 5'end to the 3'end:

a scaffold, the guide sequence, the reverse transcriptase template and the primer binding site.

P42. The pegRNA of any one of the preceding embodiments, with the proviso that the pegRNA does not comprise an extension tail at the prime editing end if the pegRNA comprises an MS within 5 nucleotides of prime editing end.

P43. The pegRNA of any one of the preceding embodiments, wherein the one or more modification within 5 nucleotides of the prime editing end comprises MS.

P44. A ribonucleoprotein (RNP) comprising the pegRNA of any one of the preceding embodiments and the Cas protein.

P45. The RNP of embodiment P44 wherein the Cas protein is in a fusion protein that also comprises a reverse transcriptase.

P46. A kit comprising one or more pegRNA independently of any one of the preceding embodiments, the Cas protein and/or the reverse transcriptase (or nucleic acid(s) encoding the Cas protein and/or the reverse transcriptase), and optionally one or more buffers.

P47. The kit of embodiment P46, comprising a fusion protein that comprises the Cas protein and the reverse transcriptase, or a nucleic acid encoding the fusion protein.

Method Embodiments (M Embodiments)

M1. A method of editing a target region in a nucleic acid, the method comprising: contacting the nucleic acid with a Cas protein capable of nicking a single strand of the nucleic acid;

a reverse transcriptase; and a pegRNA of any one of the P embodiments; and wherein the contacting results in editing of the target region.

M2. The method of embodiment M1, wherein the Cas protein and the reverse transcriptase are covalently linked, directly or indirectly, as a fusion protein.

M3. The method of embodiments M1 or M2, wherein the reverse transcriptase is an MMLV reverse transcriptase, wherein the MMLV reverse transcriptase is a wild type or a mutant version that comprises reverse transcriptase activities.

M4. The method of any one embodiments M1-M3, wherein the Cas protein and/or the reverse transcriptase are provided as mRNA(s) encoding the Cas protein and/or the reverse transcriptase.

M5. The method of any one of embodiments M1-M4, wherein the Cas protein and/or the reverse transcriptase are provided as DNA(s) encoding the Cas protein and/or the reverse transcriptase.

M6. The method of any one of embodiments M1-M4, wherein the Cas protein and/or the reverse transcriptase, and the pegRNA, are provided as a ribonucleoprotein (RNP).

M7. The method of any one of embodiments M1-M6, wherein the contacting takes place in a cell.

M8. The method of embodiment M7, wherein the cell exists ex vivo.

M9. The method of embodiment M8, wherein the cell exists in vivo.

M10. The method of embodiment M8, wherein the cell is a primary cell.

M11. The method of any one of embodiments M7-M10, wherein the cell is a T-cell.

M12. A method of editing at least two nucleic acid target regions, the method comprising:

contacting a first nucleic acid target region and a second nucleic acid target region with:

a Cas protein capable of nicking a single strand of the nucleic acid target regions;

a reverse transcriptase;

a first pegRNA of any one of the P embodiments having a guide sequence specific for the first nucleic acid target region; and a second pegRNA of any one of the P embodiments having a guide sequence specific for the second nucleic acid target region;

and wherein the contacting results in editing of the first and second nucleic acid target regions.

M13. The method of embodiment M12, wherein the two target regions are located in the same gene.

M14. The method of embodiment M12, wherein the two target regions are located in different genes.

M15. The method of any one of embodiments M12-M14, wherein the method further comprises any of the elements, limitations or steps described in Embodiments M2-M11.

M16. A cell edited by the method of any one of the preceding M embodiments.

The foregoing description of exemplary or preferred embodiments should be taken as illustrating, rather than as limiting, the present disclosure as defined by the claims. As will be readily appreciated, numerous variations and combinations of the features set forth above can be utilized without departing from the present disclosure as set forth in the claims. Such variations are not regarded as a departure from the scope of the disclosure, and all such variations are intended to be included within the scope of the following claims. All references cited herein are incorporated by reference in their entireties.

All publications, patents, and patent applications mentioned in this specification are herein incorporated by reference to the same extent as if each individual publication, patent, or patent application was specifically and individually indicated to be incorporated by reference.

We claim:

1. A prime-editing guide RNA (pegRNA) comprising:

a guide sequence that is capable of hybridizing to a target sequence in a target region of a nucleic acid;

a segment that interacts with a Cas protein;

a primer-binding site segment that can bind to the target region;

and a reverse transcriptase template segment including a sequence with desired edit(s) to the target region;

wherein the pegRNA comprises a 5' end and a 3' end, one of which is a prime-editing end and the other is referred to as a distal end, and the pegRNA comprises at least two modified nucleotides within 5 nucleotides of the prime-editing end, said at least two modified nucleotides comprising 2'-O-methyl-3'-phosphonoacetate (“MP”).

2. The pegRNA of claim 1, which does not contain an extension tail at the prime-editing end.

3. The pegRNA of claim 1, which comprises an extension tail at the 3' end or the 5' end.

4. The pegRNA of claim 1, comprising two consecutive MP modified nucleotides within 5 nucleotides of the prime-editing end.

5. The pegRNA of claim 1, comprising three consecutive MP modified nucleotides within 5 nucleotides of the prime-editing end.

6. The pegRNA of claim 1, comprising two consecutive MP modified nucleotides within 5 nucleotides of the prime-editing end and at least one 2'-O-methyl-3'-phosphorothioate (“MS”) or 2'-O-methyl-3'-thiophosphonoacetate (“MSP”) modified nucleotide within 5 nucleotides of the distal end.

7. The pegRNA of claim 1, comprising three consecutive MP modified nucleotides within 5 nucleotides of the prime-editing end and at least one MS or MSP modified nucleotide within 5 nucleotides of the distal end.

8. The pegRNA of claim 1, further comprising one or more modified nucleotides within 5 nucleotides of the distal end.

9. The pegRNA of claim 8, wherein said one or more modified nucleotides within 5 nucleotides of the distal end comprises a nucleotide comprising (1) a 2' modification selected from 2'-MOE, 2'-fluoro, 2'-O-methyl and 2'-deoxy; and (2) an internucleotide linkage modification selected from phosphorothioate, phosphonocarboxylate, and thiophosphonocarboxylate.

10. The pegRNA of claim 9, wherein said one or more modified nucleotides within 5 nucleotides of the distal end comprises MS, MP or MSP.

11. The pegRNA of claim 10, wherein the pegRNA comprises two or three consecutive MS, MP, or MSP modified nucleotides within 5 nucleotides of the distal end.

12. The pegRNA of claim 1, which is a single guide RNA.

13. A method of editing a target region comprising a target sequence in a nucleic acid, the method comprising:

contacting the target region with:

a nickase Cas protein to nick one strand of the target region;

a reverse transcriptase; and the pegRNA of claim 1;

wherein the contacting results in editing of the target region.

14. The method of claim 13, wherein the Cas protein and the reverse transcriptase are covalently linked, directly or through a linker, in a fusion protein.

15. The method of claim 13, wherein the reverse transcriptase is an MMLV reverse transcriptase or a mutated MMLV reverse transcriptase.

16. The method of claim 13, wherein the Cas protein and/or the reverse transcriptase are provided as mRNA(s) encoding the Cas protein and/or the reverse transcriptase.

17. The method of claim 13, wherein the Cas protein and the reverse transcriptase are provided as an mRNA encoding a fusion protein comprising the Cas protein and the reverse transcriptase.

18. The method of claim 13, wherein the Cas protein and/or the reverse transcriptase are provided as DNA(s) encoding the Cas protein and/or the reverse transcriptase.

19. The method of claim 13, wherein the Cas protein and the pegRNA are provided as a ribonucleoprotein (RNP), and optionally encapsulated in nanoparticles.

20. The method of claim 13, wherein the contacting takes place in a cell.

21. The method of claim 20, wherein the cell exists ex vivo.

22. The method of claim 20, wherein the cell is a primary cell.

23. A method of editing at least two nucleic acid target regions, the method comprising:

contacting a first nucleic acid and a second nucleic acid target regions with:

a Cas protein capable of nicking a single strand of the nucleic acid target regions;

a reverse transcriptase;

a first pegRNA of claim 1 having a guide sequence specific for the first nucleic acid target region; and a second pegRNA of claim 1 having a guide sequence specific for the second nucleic acid target region;

wherein the contacting results in editing of the first and second nucleic acid target regions.

* * * * *